(12) United States Patent
Wiegand et al.

(10) Patent No.: US 9,265,827 B2
(45) Date of Patent: Feb. 23, 2016

(54) ANTI-PDGFR-BETA ANTIBODIES AND USES THEREOF

(71) Applicant: REGENERON PHARMACEUTICALS, INC., Tarrytown, NY (US)

(72) Inventors: Stanley J. Wiegand, Hopewell Junction, NY (US); Ivan B. Lobov, New York, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 0 days.

(21) Appl. No.: 14/148,753

(22) Filed: Jan. 7, 2014

(65) Prior Publication Data

US 2014/0193402 A1    Jul. 10, 2014

Related U.S. Application Data

(60) Provisional application No. 61/750,437, filed on Jan. 9, 2013, provisional application No. 61/863,452, filed on Aug. 8, 2013, provisional application No. 61/909,421, filed on Nov. 27, 2013.

(51) Int. Cl.
*A61K 39/395* (2006.01)
*A61K 39/00* (2006.01)
*C07K 16/28* (2006.01)

(52) U.S. Cl.
CPC ....... *A61K 39/3955* (2013.01); *A61K 39/39541* (2013.01); *C07K 16/2863* (2013.01); *A61K 2039/505* (2013.01); *C07K 2317/21* (2013.01); *C07K 2317/24* (2013.01); *C07K 2317/76* (2013.01); *C07K 2317/77* (2013.01); *C07K 2317/92* (2013.01); *C07K 2319/30* (2013.01); *C07K 2319/32* (2013.01)

(58) Field of Classification Search
None
See application file for complete search history.

(56) References Cited

U.S. PATENT DOCUMENTS

| | | | |
|---|---|---|---|
| 5,620,687 A | 4/1997 | Hart et al. | |
| 5,817,310 A | 10/1998 | Ramakrishnan et al. | |
| 5,872,218 A | 2/1999 | Wolf et al. | |
| 5,882,644 A | 3/1999 | Chang et al. | |
| 7,060,271 B2 | 6/2006 | Ramakrishnan et al. | |
| 7,740,850 B2 | 6/2010 | Zhu et al. | |
| 7,759,472 B2 | 7/2010 | Shima et al. | |
| 8,206,707 B2 | 6/2012 | Shima et al. | |
| 2002/0009443 A1 | 1/2002 | Ramakrishman et al. | |
| 2011/0021424 A1 | 1/2011 | Lindborg et al. | |
| 2012/0100136 A1 | 4/2012 | Patel et al. | |

FOREIGN PATENT DOCUMENTS

WO    2008/130704    10/2008
WO    2009/120922    10/2009

OTHER PUBLICATIONS

Lokker et al., "Functional Importance of platelet-derived growth factor (PDGH) receptor extracellular immunoglobulin-like domains. Identification of PDGF binding site and neutralizing monoclonal antibodies" Journal of Biological Chemistry and Molecular Biology (Dec. 26, 1997) 272(52):33037-33044.
Andrae et aL, "Role of platelet-derived growth factors in physiology and medicine" Genes & Development (2008) 22:1276-1312.
Armulik et al., "Pericytes: Developmental, Physiological, and Pathological Perspectives, Problems and Promises" Developmental Cell Review (Aug. 16, 2011) 21:193-215.
Jo et al., "Inhibition of Platelet-Derived Growth Factor B Signaling Enhances the Efficacy of Anti-Vascular Endothelial Growth Factor Therapy in Multiple Models of Ocular Neovascularization" American Journal of Pathology (Jun. 2006) 168(6):2036-2053.
Kuhnert et al., "Soluble receptor-mediated selective inhibition of VEGFR and PDGFR beta signaling during physiologic and tumor angiogenesis" Proc. Nat Acad. Sci. USA (Jul. 22, 2008) 105(29):10185-10190.
Shen et al., "An antibody directed against PDGF receptor beta enhances the antitumor and the anti-angiogenic activities of an anti-VEGF receptor 2 antibody" Biochemical and Biophysical Research Communications (2007) 357:1142-1147.
Uemura et al., "Recombinant angiopoietin-1 restores higher-order architeture of growing blood vessels in mice and the absence of mural cells" The Journal of Clinical Investigation (Dec. 2002) 110(11):1619-1628.

*Primary Examiner* — Ruixiang Li
(74) *Attorney, Agent, or Firm* — Anna D. DiGabriele Petti; Frank Cottingham; Karl Bozicevic

(57) ABSTRACT

The present invention provides antibodies that bind to platelet derived growth factor receptor beta (PDGFR-beta) and methods of using the same. According to certain embodiments of the invention, the antibodies are fully human antibodies that bind to human PDGFR-beta with high affinity. The antibodies of the invention are useful for the treatment of diseases and disorders associated with PDGFR-beta signaling and/or PDGFR-beta cellular expression, such as ocular diseases, fibrotic diseases, vascular diseases and cancer.

6 Claims, 2 Drawing Sheets

FIG. 2

| anti-PDGFRβ mAb # | anti-PDGFRβ mAbs | Amount of hPDGFRβ.mmh Captured ±Std Dev (nm) | Amount of mAb-1 Binding ±Std Dev (nm) | Response of mAb-2 Binding to hPDGFRβ.mmh Pre-Complexed with mAb-1 (nm) | | | | | | | | |
|---|---|---|---|---|---|---|---|---|---|---|---|---|
| | | | | 1 | 2 | 3 | 4 | 5 | 6 | 7 | 8 | 9 |
| 1 | Control | 0.23 ± 0.01 | 0.32 ± 0.01 | 0.05 | -0.02 | -0.02 | -0.01 | -0.01 | 0.28 | 0.28 | 0.22 | 0.20 |
| 2 | H4H3365N | 0.23 ± 0.01 | 0.25 ± 0.01 | 0.08 | 0.01 | 0.01 | 0.02 | 0.03 | 0.33 | 0.32 | 0.26 | 0.24 |
| 3 | H4H3374N | 0.23 ± 0.01 | 0.25 ± 0.01 | 0.06 | 0.01 | 0.00 | 0.01 | 0.02 | 0.31 | 0.31 | 0.24 | 0.23 |
| 4 | H4H3103S | 0.25 ± 0.01 | 0.27 ± 0.01 | 0.08 | 0.01 | 0.02 | 0.01 | 0.02 | 0.34 | 0.33 | 0.25 | 0.24 |
| 5 | H4H3094P | 0.23 ± 0.01 | 0.25 ± 0.01 | 0.05 | 0.00 | 0.00 | 0.00 | 0.00 | 0.35 | 0.36 | 0.27 | 0.27 |
| 6 | H4H3099S | 0.25 ± 0.01 | 0.35 ± 0.01 | 0.34 | 0.29 | 0.27 | 0.26 | 0.25 | 0.02 | 0.01 | 0.00 | -0.01 |
| 7 | H4H3107S | 0.24 ± 0.01 | 0.34 ± 0.01 | 0.32 | 0.26 | 0.24 | 0.24 | 0.23 | 0.05 | 0.01 | 0.00 | -0.01 |
| 8 | H4H3305N | 0.24 ± 0.01 | 0.25 ± 0.01 | 0.34 | 0.28 | 0.27 | 0.26 | 0.25 | 0.04 | 0.02 | 0.01 | 0.01 |
| 9 | H4H3310N | 0.24 ± 0.01 | 0.24 ± 0.01 | 0.33 | 0.28 | 0.26 | 0.25 | 0.25 | 0.12 | 0.02 | 0.01 | 0.01 |

ANTI-PDGFR-BETA ANTIBODIES AND USES THEREOF

CROSS-REFERENCE TO RELATED APPLICATIONS

This application claims the benefit under 35 U.S.C. §119 (e) of U.S. provisional application Nos. 61/750,437, filed on Jan. 9, 2013; 61/863,452, filed on Aug. 8, 2013; and 61/909, 421, filed on Nov. 27, 2013, the disclosures of which are herein incorporated by reference in their entireties.

FIELD OF THE INVENTION

The present invention relates to antibodies, and antigen-binding fragments thereof, which are specific for human PDGFR-beta, and methods of use thereof.

BACKGROUND

Platelet-derived growth factors (PDGFs) are potent mitogens that exist as five different dimeric configurations composed of four different isoform subunits: A, B, C and D. The five dimeric forms of the PDGFs are AA, BB, AB, CC and DD, which are formed by disulfide linkage of the corresponding individual PDGF monomers. PDGF ligands exert their biological effects through their interactions with PDGF receptors (PDGFRs). PDGFRs are single-pass, transmembrane, tyrosine kinase receptors composed of heterodimeric or homodimeric associations of an alpha (α) receptor chain (PDGFR-alpha) and/or a beta (β) receptor chain (PDGFR-beta). Thus, active PDGFRs may consist of αα, ββ or αβ receptor chain pairings. PDGFRs share a common domain structure, including five extracellular immunoglobulin (Ig) loops, a transmembrane domain, and a split intracellular tyrosine kinase (TK) domain. The interaction between dimeric PDGF ligands and PDGFRs leads to receptor chain dimerization, receptor autophosphorylation and intracellular signal transduction. It has been demonstrated in vitro that ββ receptors are activated by PDGF-BB and -DD, while αβ receptors are activated by PDGF-BB, -CC, -DD and -AB, and αα receptors are activated by PDGF-AA, -BB, -CC and -AB (see Andrae et al. (2008) Genes Dev 22(10):1276-1312).

PDGF signaling has been implicated in various human diseases including diseases associated with pathological neovascularization, vascular and fibrotic diseases, tumor growth and eye diseases. Accordingly, inhibitors of PDGF signaling have been suggested for use in a variety of therapeutic settings. For example, inhibitors of PDGFR-beta have been proposed for use in treating various diseases and disorders. (Andrae et al. (2008) Genes Dev 22(10):1276-1312). PDGFR-beta inhibitors include non-specific small molecule tyrosine kinase inhibitors such as imatinib mesylate, sunitinib malate and CP-673451, as well as anti-PDGFR-beta antibodies (see, e.g., U.S. Pat. Nos. 7,060,271; 5,882,644; 7,740,850; and U.S. Patent Appl. Publ. No. 2011/0177074). Anti-ligand aptamers (e.g., anti-PDGF-B) have also been proposed for therapeutic applications. Nonetheless, a need exists in the art for new, highly specific and potent inhibitors of PDGF signaling.

BRIEF SUMMARY OF THE INVENTION

The present invention provides antibodies that bind human platelet-derived growth factor receptor beta ("PDGFR-beta"). The antibodies of the invention are useful, inter alia, for inhibiting PDGFR-beta-mediated signaling and for treating diseases and disorders caused by or related to PDGFR-beta activity and/or signaling. The antibodies of the invention are also useful for inducing cell death in cells that express high levels of PDGFR-beta on their surfaces.

The antibodies of the invention can be full-length (for example, an IgG1 or IgG4 antibody) or may comprise only an antigen-binding portion (for example, a Fab, F(ab')$_2$ or scFv fragment), and may be modified to affect functionality, e.g., to eliminate residual effector functions (Reddy et al., 2000, J. Immunol. 164:1925-1933).

The present invention provides antibodies, or antigen-binding fragments thereof comprising a heavy chain variable region (HCVR) having an amino acid sequence selected from the group consisting of SEQ ID NO: 2, 18, 34, 50, 66, 82, 98, 114, 130, 146, 162, 178, 194, 210, 226, 242, 258, 274, 290, 306, and 322, or a substantially similar sequence thereof having at least 90%, at least 95%, at least 98% or at least 99% sequence identity.

The present invention also provides an antibody or antigen-binding fragment of an antibody comprising a light chain variable region (LCVR) having an amino acid sequence selected from the group consisting of SEQ ID NO: 10, 26, 42, 58, 74, 90, 106, 122, 138, 154, 170, 186, 202, 218, 234, 250, 266, 282, 298, 314, and 330, or a substantially similar sequence thereof having at least 90%, at least 95%, at least 98% or at least 99% sequence identity.

The present invention also provides an antibody or antigen-binding fragment thereof comprising a HCVR and LCVR (HCVR/LCVR) sequence pair selected from the group consisting of SEQ ID NO: 2/10, 18/26, 34/42, 50/58, 66/74, 82/90, 98/106, 114/122, 130/138, 146/154, 162/170, 178/186, 194/202, 210/218, 226/234, 242/250, 258/266, 274/282, 290/298, 306/314, and 322/330.

The present invention also provides an antibody or antigen-binding fragment of an antibody comprising a heavy chain CDR3 (HCDR3) domain having an amino acid sequence selected from the group consisting of SEQ ID NO: 8, 24, 40, 56, 72, 88, 104, 120, 136, 152, 168, 184, 200, 216, 232, 248, 264, 280, 296, 312, and 328, or a substantially similar sequence thereof having at least 90%, at least 95%, at least 98% or at least 99% sequence identity; and a light chain CDR3 (LCDR3) domain having an amino acid sequence selected from the group consisting of SEQ ID NO: 16, 32, 48, 64, 80, 96, 112, 128, 144, 160, 176, 192, 208, 224, 240, 256, 272, 288, 304, 320, and 336, or a substantially similar sequence thereof having at least 90%, at least 95%, at least 98% or at least 99% sequence identity.

In certain embodiments, the antibody or antigen-binding portion of an antibody comprises a HCDR3/LCDR3 amino acid sequence pair selected from the group consisting of SEQ ID NO: 8/16, 24/32, 40/48, 56/64, 72/80, 88/96, 104/112, 120/128, 136/144, 152/160, 168/176, 184/192, 200/208, 216/224, 232/240, 248/256, 264/272, 280/288, 296/304, 312/320, and 328/336.

The present invention also provides an antibody or fragment thereof further comprising a heavy chain CDR1 (HCDR1) domain having an amino acid sequence selected from the group consisting of SEQ ID NO: 4, 20, 36, 52, 68, 84, 100, 116, 132, 148, 164, 180, 196, 212, 228, 244, 260, 276, 292, 308, and 324, or a substantially similar sequence thereof having at least 90%, at least 95%, at least 98% or at least 99% sequence identity; a heavy chain CDR2 (HCDR2) domain having an amino acid sequence selected from the group consisting of SEQ ID NO: 6, 22, 38, 54, 70, 86, 102, 118, 134, 150, 166, 182, 198, 214, 230, 246, 262, 278, 294, 310, and 326, or a substantially similar sequence thereof having at least 90%, at least 95%, at least 98% or at least 99% sequence identity; a light chain CDR1 (LCDR1) domain having an amino acid sequence selected from the group consisting of SEQ ID NO: 12, 28, 44, 60, 76, 92, 108, 124, 140, 156, 172, 188, 204, 220, 236, 252, 268, 284, 300, 316, and 332, or a substantially similar sequence thereof having at least 90%, at least 95%, at least 98% or at least 99% sequence identity; and a light chain CDR2 (LCDR2) domain having an amino acid sequence selected from the group consisting of SEQ ID NO: 14, 30, 46, 62, 78, 94, 110, 126, 142, 158, 174, 190, 206, 222, 238, 254, 270, 286, 302, 318, and 334, or a substantially similar sequence thereof having at least 90%, at least 95%, at least 98% or at least 99% sequence identity.

Certain non-limiting, exemplary antibodies and antigen-binding fragments of the invention comprise HCDR1-HCDR2-HCDR3-LCDR1-LCDR2-LCDR3 domains, respectively, having the amino acid sequences selected from the group consisting of: SEQ ID NOs: 4-6-8-12-14-16 (e.g. H1M3299N); 20-22-24-28-30-32 (e.g. H1M3305N); 36-38-40-44-46-48 (e.g. H1M3310N); 52-54-56-60-62-64 (e.g. H1M3361N); 68-70-72-76-78-80 (e.g. H2M3363N); 84-86-88-92-94-96 (e.g. H2M3365N); 100-102-104-108-110-112 (e.g. H2M3368N); 116-118-120-124-126-128 (e.g. H2M3373N); 132-134-136-140-142-144 (e.g. H2M3374N); 148-150-152-156-158-160 (e.g., H4H3094P); 164-166-168-172-174-176 (e.g. H4H3095S); 180-182-184-188-190-192 (e.g., H4H3096S); 196-198-200-204-206-208 (e.g. H4H3097S); 212-214-216-220-222-224 (e.g. H4H3098S); 228-230-232-236-238-240 (e.g. H4H3099S); 244-246-248-252-254-256 (e.g. H4H3102S); 260-262-264-268-270-272 (e.g. H4H3103S); 276-278-280-284-286-288 (e.g. H4H3104S); 292-294-296-300-302-304 (e.g. H4H3105S); 308-310-312-316-318-320 (e.g. H4H3106S); and 324-326-328-332-334-336 (e.g. H4H3107S).

In a related embodiment, the invention includes an antibody or antigen-binding fragment of an antibody which specifically binds PDGFR-beta, wherein the antibody or fragment comprises the heavy and light chain CDR domains contained within heavy and light chain variable region (HCVR/LCVR) sequences selected from the group consisting of SEQ ID NO: 2/10, 18/26, 34/42, 50/58, 66/74, 82/90, 98/106, 114/122, 130/138, 146/154, 162/170, 178/186, 194/202, 210/218, 226/234, 242/250, 258/266, 274/282, 290/298, 306/314, and 322/330. Methods and techniques for identifying CDRs within HCVR and LCVR amino acid sequences are well known in the art and can be used to identify CDRs within the specified HCVR and/or LCVR amino acid sequences disclosed herein. Exemplary conventions that can be used to identify the boundaries of CDRs include, e.g., the Kabat definition, the Chothia definition, and the AbM definition. In general terms, the Kabat definition is based on sequence variability, the Chothia definition is based on the location of the structural loop regions, and the AbM definition is a compromise between the Kabat and Chothia approaches. See, e.g., Kabat, "Sequences of Proteins of Immunological Interest," National Institutes of Health, Bethesda, Md. (1991); Al-Lazikani et al., *J. Mol. Biol.* 273:927-948 (1997); and Martin et al., *Proc. Natl. Acad. Sci. USA* 86:9268-9272 (1989). Public databases are also available for identifying CDR sequences within an antibody.

In another aspect, the invention provides nucleic acid molecules encoding anti-PDGFR-beta antibodies or antigen-binding fragments thereof. Recombinant expression vectors carrying the nucleic acids of the invention, and host cells into which such vectors have been introduced, are also encompassed by the invention, as are methods of producing the antibodies by culturing the host cells under conditions permitting production of the antibodies, and recovering the antibodies produced.

In one embodiment, the invention provides an antibody or fragment thereof comprising a HCVR encoded by a nucleic acid sequence selected from the group consisting of SEQ ID NO: 1, 17, 33, 49, 65, 81, 97, 113, 129, 145, 161, 177, 193, 209, 225, 241, 257, 273, 289, 305, and 321, or a substantially identical sequence having at least 90%, at least 95%, at least 98%, or at least 99% homology thereof.

The present invention also provides an antibody or fragment thereof comprising a LCVR encoded by a nucleic acid sequence selected from the group consisting of SEQ ID NO: 9, 25, 41, 57, 73, 89, 105, 121, 137, 153, 169, 185, 201, 217, 233, 249, 265, 281, 297, 313, and 329, or a substantially identical sequence having at least 90%, at least 95%, at least 98%, or at least 99% homology thereof.

The present invention also provides an antibody or antigen-binding fragment of an antibody comprising a HCDR3 domain encoded by a nucleotide sequence selected from the group consisting of SEQ ID NO: 7, 23, 39, 55, 71, 87, 103, 119, 135, 151, 167, 183, 199, 215, 231, 247, 263, 279, 295, 311, and 327, or a substantially identical sequence having at least 90%, at least 95%, at least 98%, or at least 99% homology thereof; and a LCDR3 domain encoded by a nucleotide sequence selected from the group consisting of SEQ ID NO: 15, 31, 47, 63, 79, 95, 111, 127, 143, 159, 175, 191, 207, 223, 239, 255, 271, 287, 303, 319, and 335, or a substantially identical sequence having at least 90%, at least 95%, at least 98%, or at least 99% homology thereof.

The present invention also provides an antibody or fragment thereof which further comprises a HCDR1 domain encoded by a nucleotide sequence selected from the group consisting of SEQ ID NO: 3, 19, 35, 51, 67, 83, 99, 115, 131, 147, 163, 179, 195, 211, 227, 243, 259, 275, 291, 307, and 323, or a substantially identical sequence having at least 90%, at least 95%, at least 98%, or at least 99% homology thereof; a HCDR2 domain encoded by a nucleotide sequence selected from the group consisting of SEQ ID NO: 5, 21, 37, 53, 69, 85, 101, 117, 133, 149, 165, 181, 197, 213, 229, 245, 261, 277, 293, 309, and 325, or a substantially identical sequence having at least 90%, at least 95%, at least 98%, or at least 99% homology thereof; a LCDR1 domain encoded by a nucleotide sequence selected from the group consisting of SEQ ID NO: 11, 27, 43, 59, 75, 91, 107, 123, 139, 155, 171, 187, 203, 219, 235, 251, 267, 283, 299, 315, and 331, or a substantially identical sequence having at least 90%, at least 95%, at least 98%, or at least 99% homology thereof; and a LCDR2 domain encoded by a nucleotide sequence selected from the group consisting of SEQ ID NO: 13, 29, 45, 61, 77, 93, 109, 125, 141, 157, 173, 189, 205, 221, 237, 253, 269, 285, 301, 317, and 333, or a substantially identical sequence having at least 90%, at least 95%, at least 98%, or at least 99% homology thereof.

According to certain embodiments, the antibody or fragment thereof comprises the heavy and light chain CDR sequences encoded by the nucleic acid sequences of SEQ ID NOs: 1 and 9 (e.g. H1M3299N), 17 and 25 (e.g. H1M3305N), 33 and 41 (e.g. H1M3310N), 49 and 57 (e.g. H1M3361N), 65 and 73 (e.g. H2M3363N), 81 and 89 (e.g. H2M3365N), 97 and 105 (e.g. H2M3368N), 113 and 121 (e.g. H2M3373N), 129 and 137 (e.g. H2M3374N), 145 and 153 (e.g. H4H3094P), 161 and 169 (e.g. H4H3095S), 177 and 185 (e.g. H4H3096S), 193 and 201 (e.g. H4H3097S), 209 and 217 (e.g. H4H3098S), 225 and 233 (e.g. H4H3099S), 241 and 249 (e.g. H4H3102S), 257 and 265 (e.g. H4H3103S), 273 and 281 (e.g.

H4H3104S), 289 and 297 (e.g. H4H3105S), 305 and 313 (e.g. H4H3106S), or 321 and 329 (e.g. H4H3107S).

The present invention includes anti-PDGFR-beta antibodies having a modified glycosylation pattern. In some applications, modification to remove undesirable glycosylation sites may be useful, or an antibody lacking a fucose moiety present on the oligosaccharide chain, for example, to increase antibody dependent cellular cytotoxicity (ADCC) function (see Shield et al. (2002) JBC 277:26733). In other applications, modification of galactosylation can be made in order to modify complement dependent cytotoxicity (CDC).

In another aspect, the invention provides a pharmaceutical composition comprising a recombinant human antibody or fragment thereof which specifically binds PDGFR-beta and a pharmaceutically acceptable carrier. In a related aspect, the invention features a composition which is a combination of an anti-PDGFR-beta antibody and a second therapeutic agent. In one embodiment, the second therapeutic agent is any agent that is advantageously combined with an anti-PDGFR-beta antibody. Exemplary agents that may be advantageously combined with an anti-PDGFR-beta antibody include, without limitation, other agents that inhibit PDGFR-beta activity (including other antibodies or antigen-binding fragments thereof, peptide inhibitors, small molecule antagonists, etc.) and/or agents which do not directly bind PDGFR-beta but nonetheless interfere with, block or attenuate PDGFR-beta-mediated signaling. Additional combination therapies and co-formulations involving the anti-PDGFR-beta antibodies of the present invention are disclosed elsewhere herein.

In yet another aspect, the invention provides therapeutic methods for inhibiting PDGFR-beta activity using an anti-PDGFR-beta antibody or antigen-binding portion of an antibody of the invention, wherein the therapeutic methods comprise administering a therapeutically effective amount of a pharmaceutical composition comprising an antibody or antigen-binding fragment of an antibody of the invention. The disorder treated is any disease or condition which is improved, ameliorated, inhibited or prevented by removal, inhibition or reduction of PDGFR-beta activity or signaling. The anti-PDGFR-beta antibodies or antibody fragments of the invention may function to block the interaction between PDGFR-beta and a PDGFR-beta binding partner (e.g., a PDGF ligand), or otherwise inhibit the signaling activity of PDGFR-beta.

The present invention also includes the use of an anti-PDGFR-beta antibody or antigen binding portion of an antibody of the invention in the manufacture of a medicament for the treatment of a disease or disorder related to or caused by PDGFR-beta activity in a patient.

Other embodiments will become apparent from a review of the ensuing detailed description.

BRIEF DESCRIPTION OF THE FIGURES

FIG. 2 is a matrix showing the results of an antibody cross-competition assay in which a first anti-PDGFR-beta antibody (mAb#1) was applied to a PDGFR-beta-coated sensor tip, followed by treatment with a second anti-PDGFR-beta antibody (mAb#2). Binding responses (numerical values −0.01 to 0.36) for each antibody combination tested are depicted. Light grey boxes with black font represent binding response for self-competition. Antibodies competing in both directions, independent of the order of antigen binding, are highlighted in black boxes with white font. No competition, suggesting distinct binding regions, is represented as white boxes with black font.

DETAILED DESCRIPTION

Figure 1:
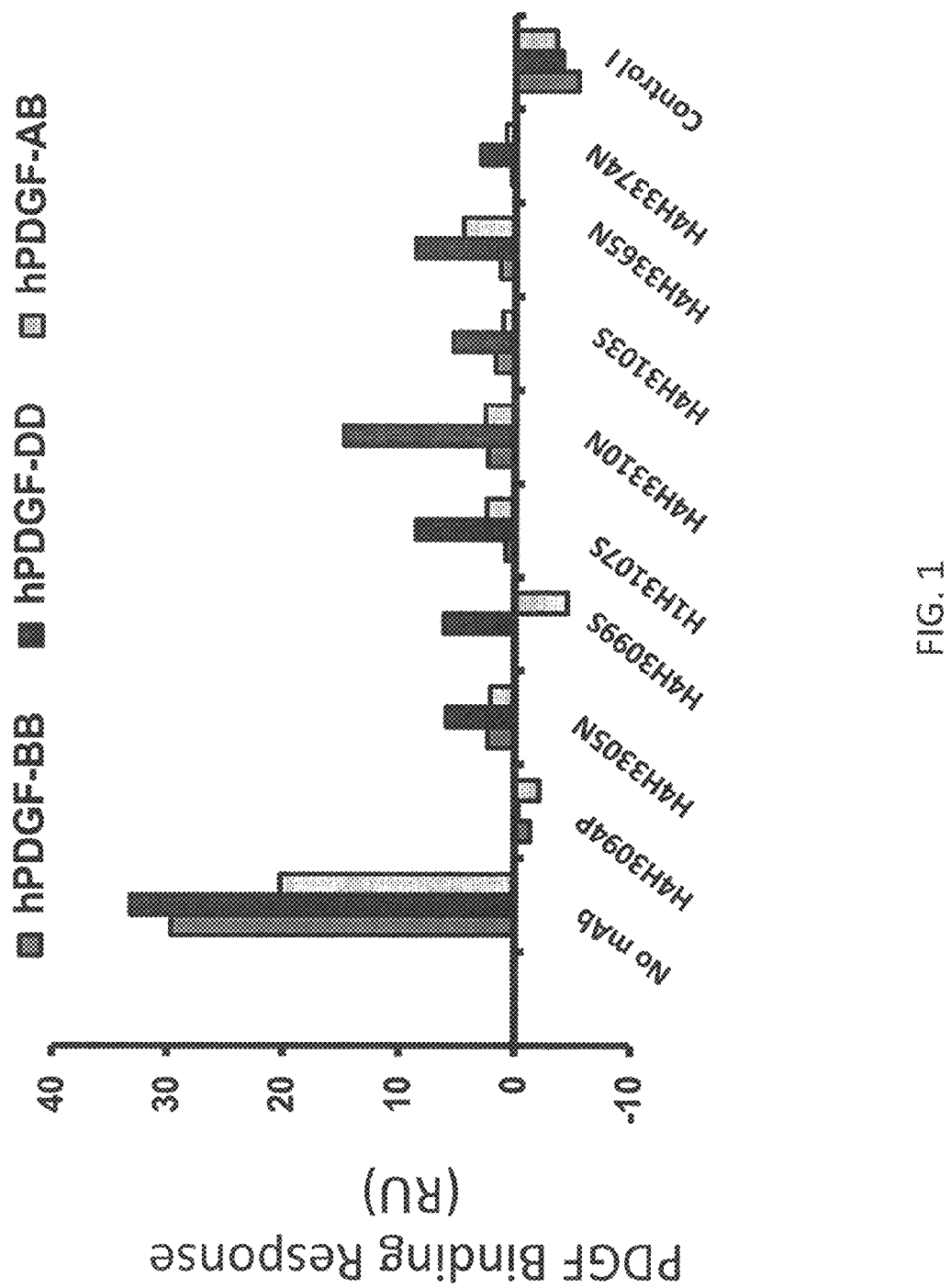
FIG. 1 is a histogram showing the results of a PDGF ligand blocking assay in which PDGFR-beta was captured on a biosensor surface and PDGF ligand (BB, DD or AB) was applied to the surface following treatment with various anti-PDGFR-beta antibodies of the invention or control antibody. Results are shown as RUs.

Before the present invention is described, it is to be understood that this invention is not limited to particular methods and experimental conditions described, as such methods and conditions may vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. As used herein, the term "about," when used in reference to a particular recited numerical value, means that the value may vary from the recited value by no more than 1%. For example, as used herein, the expression "about 100" includes 99 and 101 and all values in between (e.g., 99.1, 99.2, 99.3, 99.4, etc.).

Although any methods and materials similar or equivalent to those described herein can be used in the practice or testing of the present invention, the preferred methods and materials are now described. All patents, applications and non-patent publications mentioned in this specification are incorporated herein by reference in their entireties.

DEFINITIONS

The expressions "platelet-derived growth factor receptor beta," "PDGFRβ," "PDGFR-beta," "PDGFRb" and the like, as used herein, refer to the human PDGFR-beta protein having the amino acid sequence of SEQ ID NO:341 (see also UniProt accession No. P09619). All references to proteins, polypeptides and protein fragments herein are intended to refer to the human version of the respective protein, polypeptide or protein fragment unless explicitly specified as being from a non-human species (e.g., "mouse PDGFR-beta," "monkey PDGFR-beta," etc.).

As used herein, "an antibody that binds PDGFR-beta" or an "anti-PDGFR-beta antibody" includes antibodies, and antigen-binding fragments thereof, that bind a soluble fragment of an PDGFR-beta protein (e.g., all or a portion of the extracellular domain of PDGFR-beta) and/or cell surface-expressed PDGFR-beta. The expression "cell surface-expressed PDGFR-beta" means a PDGFR-beta protein or portion thereof that is expressed on the surface of a cell in vitro or in vivo, such that at least a portion of the PDGFR-beta protein (e.g., amino acids 33 to 532 of SEQ ID NO:341) is exposed to the extracellular side of the cell membrane and is accessible to an antigen-binding portion of an antibody. "Cell surface-expressed PDGFR-beta" includes PDGFR-beta molecules in the context of ββ receptor homodimers as well as PDGFR-beta molecules in the context of αβ heterodimers. Soluble PDGFR-beta molecules include, e.g., monomeric and dimeric PDGFR-beta constructs as described in Example 3 herein (e.g., "PDGFRb.mmh", SEQ ID NO:337 [monomeric], "PDGFRb.mFc", SEQ ID NO:338 [dimeric] and "PDGFRb.hFc", SEQ ID NO:339 [dimeric]), or constructs substantially similar thereto.

The term "antibody", as used herein, means any antigen-binding molecule or molecular complex comprising at least one complementarity determining region (CDR) that specifically binds to or interacts with a particular antigen (e.g., PDGFR-beta). The term "antibody" includes immunoglobulin molecules comprising four polypeptide chains, two heavy (H) chains and two light (L) chains inter-connected by disulfide bonds, as well as multimers thereof (e.g., IgM). Each heavy chain comprises a heavy chain variable region (abbreviated herein as HCVR or $V_H$) and a heavy chain constant region. The heavy chain constant region comprises three domains, $C_H1$, $C_H2$ and $C_H3$. Each light chain comprises a light chain variable region (abbreviated herein as LCVR or $V_L$) and a light chain constant region. The light chain constant region comprises one domain ($C_L1$). The $V_H$ and $V_L$ regions can be further subdivided into regions of hypervariability, termed complementarity determining regions (CDRs), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In different embodiments of the invention, the FRs of the anti-PDGFR-beta antibody (or antigen-binding portion thereof) may be identical to the human germline sequences, or may be naturally or artificially modified. An amino acid consensus sequence may be defined based on a side-by-side analysis of two or more CDRs.

The term "antibody", as used herein, also includes antigen-binding fragments of full antibody molecules. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g. monovalent nanobodies, bivalent nanobodies, etc.), small modular immunopharmaceuticals (SMIPs), and shark variable IgNAR domains, are also encompassed within the expression "antigen-binding fragment," as used herein.

An antigen-binding fragment of an antibody will typically comprise at least one variable domain. The variable domain may be of any size or amino acid composition and will generally comprise at least one CDR which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers. Alternatively, the antigen-binding fragment of an antibody may contain a monomeric $V_H$ or $V_L$ domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present invention include: (i) $V_H$-$C_H1$; (ii) $V_H$-$C_H2$; (iii) $V_H$-$C_H3$; (iv) $V_H$-$C_H1$-$C_H2$; (v) $V_H$-$C_H1$-$C_H2$-$C_H3$; (vi) $V_H$-$C_H2$-$C_H3$; (vii) $V_H$-$C_L$; (viii) $V_L$-$C_H1$; (ix) $V_L$-$C_H2$; (x) $V_L$-$C_H3$; (xi) $V_L$-$C_H1$-$C_H2$; (xii) $V_L$-$C_H1$-$C_H2$-$C_H3$; (xiii) $V_L$-$C_H2$-$C_H3$; and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids which result in a flexible or semi-flexible linkage between adjacent variable and/or constant domains in a single polypeptide molecule. Moreover, an antigen-binding fragment of an antibody of the present invention may comprise a homo-dimer or hetero-dimer (or other multimer) of any of the variable and constant domain configurations listed above in non-covalent association with one another and/or with one or more monomeric $V_H$ or $V_L$ domain (e.g., by disulfide bond(s)).

As with full antibody molecules, antigen-binding fragments may be monospecific or multispecific (e.g., bispecific). A multispecific antigen-binding fragment of an antibody will typically comprise at least two different variable domains, wherein each variable domain is capable of specifically binding to a separate antigen or to a different epitope on the same antigen. Any multispecific antibody format, including the exemplary bispecific antibody formats disclosed herein, may be adapted for use in the context of an antigen-binding fragment of an antibody of the present invention using routine techniques available in the art.

The antibodies of the present invention may function through complement-dependent cytotoxicity (CDC) or antibody-dependent cell-mediated cytotoxicity (ADCC). "Complement-dependent cytotoxicity" (CDC) refers to lysis of antigen-expressing cells by an antibody of the invention in the presence of complement. "Antibody-dependent cell-mediated cytotoxicity" (ADCC) refers to a cell-mediated reaction in which nonspecific cytotoxic cells that express Fc receptors (FcRs) (e.g., Natural Killer (NK) cells, neutrophils, and macrophages) recognize bound antibody on a target cell and thereby lead to lysis of the target cell. CDC and ADCC can be measured using assays that are well known and available in the art. (See, e.g., U.S. Pat. Nos. 5,500,362 and 5,821,337, and Clynes et al. (1998) Proc. Natl. Acad. Sci. (USA) 95:652-656). The constant region of an antibody is important in the ability of an antibody to fix complement and mediate cell-dependent cytotoxicity. Thus, the isotype of an antibody may be selected on the basis of whether it is desirable for the antibody to mediate cytotoxicity.

In certain embodiments of the invention, the anti-PDGFR-beta antibodies of the invention are human antibodies. The term "human antibody", as used herein, is intended to include antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include antibodies in which CDR sequences derived from the germline of another mammalian species, such as a mouse, have been grafted onto human framework sequences.

The antibodies of the invention may, in some embodiments, be recombinant human antibodies. The term "recombinant human antibody", as used herein, is intended to include all human antibodies that are prepared, expressed, created or isolated by recombinant means, such as antibodies expressed using a recombinant expression vector transfected into a host cell (described further below), antibodies isolated from a recombinant, combinatorial human antibody library (described further below), antibodies isolated from an animal (e.g., a mouse) that is transgenic for human immunoglobulin genes (see e.g., Taylor et al. (1992) Nucl. Acids Res. 20:6287-6295) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

Human antibodies can exist in two forms that are associated with hinge heterogeneity. In one form, an immunoglobulin molecule comprises a stable four chain construct of approximately 150-160 kDa in which the dimers are held together by an interchain heavy chain disulfide bond. In a second form, the dimers are not linked via inter-chain disulfide bonds and a molecule of about 75-80 kDa is formed composed of a covalently coupled light and heavy chain (half-antibody). These forms have been extremely difficult to separate, even after affinity purification.

The frequency of appearance of the second form in various intact IgG isotypes is due to, but not limited to, structural differences associated with the hinge region isotype of the antibody. A single amino acid substitution in the hinge region of the human IgG4 hinge can significantly reduce the appearance of the second form (Angal et al. (1993) Molecular Immunology 30:105) to levels typically observed using a human IgG1 hinge. The instant invention encompasses antibodies having one or more mutations in the hinge, $C_H2$ or $C_H3$ region which may be desirable, for example, in production, to improve the yield of the desired antibody form.

The antibodies of the invention may be isolated antibodies. An "isolated antibody," as used herein, means an antibody that has been identified and separated and/or recovered from at least one component of its natural environment. For example, an antibody that has been separated or removed from at least one component of an organism, or from a tissue or cell in which the antibody naturally exists or is naturally produced, is an "isolated antibody" for purposes of the present invention. An isolated antibody also includes an antibody in situ within a recombinant cell. Isolated antibodies are antibodies that have been subjected to at least one purification or isolation step. According to certain embodiments, an isolated antibody may be substantially free of other cellular material and/or chemicals.

The present invention includes neutralizing and/or blocking anti-PDGFR-beta antibodies. A "neutralizing" or "blocking" antibody, as used herein, is intended to refer to an antibody whose binding to PDGFR-beta: (i) interferes with the interaction between PDGFR-beta or a PDGFR-beta fragment and a PDGF ligand (e.g., PDGF-BB, PDGF-CC, PDGF-DD, PDGF-AB, etc.); (ii) interferes with the formation of ββ and/or αβ receptor dimers; and/or (ii) results in inhibition of at least one biological function of PDGFR-beta. The inhibition caused by a PDGFR-beta neutralizing or blocking antibody need not be complete so long as it is detectable using an appropriate assay. Exemplary assays for detecting PDGFR-beta inhibition are described in the working Examples herein.

The anti-PDGFR-beta antibodies disclosed herein may comprise one or more amino acid substitutions, insertions and/or deletions in the framework and/or CDR regions of the heavy and light chain variable domains as compared to the corresponding germline sequences from which the antibodies were derived. Such mutations can be readily ascertained by comparing the amino acid sequences disclosed herein to germline sequences available from, for example, public antibody sequence databases. The present invention includes antibodies, and antigen-binding fragments thereof, which are derived from any of the amino acid sequences disclosed herein, wherein one or more amino acids within one or more framework and/or CDR regions are mutated to the corresponding residue(s) of the germline sequence from which the antibody was derived, or to the corresponding residue(s) of another human germline sequence, or to a conservative amino acid substitution of the corresponding germline residue(s) (such sequence changes are referred to herein collectively as "germline mutations"). A person of ordinary skill in the art, starting with the heavy and light chain variable region sequences disclosed herein, can easily produce numerous antibodies and antigen-binding fragments which comprise one or more individual germline mutations or combinations thereof. In certain embodiments, all of the framework and/or CDR residues within the $V_H$ and/or $V_L$ domains are mutated back to the residues found in the original germline sequence from which the antibody was derived. In other embodiments, only certain residues are mutated back to the original germline sequence, e.g., only the mutated residues found within the first 8 amino acids of FR1 or within the last 8 amino acids of FR4, or only the mutated residues found within CDR1, CDR2 or CDR3. In other embodiments, one or more of the framework and/or CDR residue(s) are mutated to the corresponding residue(s) of a different germline sequence (i.e., a germline sequence that is different from the germline sequence from which the antibody was originally derived). Furthermore, the antibodies of the present invention may contain any combination of two or more germline mutations within the framework and/or CDR regions, e.g., wherein certain individual residues are mutated to the corresponding residue of a particular germline sequence while certain other residues that differ from the original germline sequence are maintained or are mutated to the corresponding residue of a different germline sequence. Once obtained, antibodies and antigen-binding fragments that contain one or more germline mutations can be easily tested for one or more desired property such as, improved binding specificity, increased binding affinity, improved or enhanced antagonistic or agonistic biological properties (as the case may be), reduced immunogenicity, etc. Antibodies and antigen-binding fragments obtained in this general manner are encompassed within the present invention.

The present invention also includes anti-PDGFR-beta antibodies comprising variants of any of the HCVR, LCVR, and/or CDR amino acid sequences disclosed herein having one or more conservative substitutions. For example, the present invention includes anti-PDGFR-beta antibodies having HCVR, LCVR, and/or CDR amino acid sequences with, e.g., 10 or fewer, 8 or fewer, 6 or fewer, 4 or fewer, etc. conservative amino acid substitutions relative to any of the HCVR, LCVR, and/or CDR amino acid sequences disclosed herein.

The term "epitope" refers to an antigenic determinant that interacts with a specific antigen binding site in the variable region of an antibody molecule known as a paratope. A single antigen may have more than one epitope. Thus, different antibodies may bind to different areas on an antigen and may have different biological effects. Epitopes may be either conformational or linear. A conformational epitope is produced by spatially juxtaposed amino acids from different segments of the linear polypeptide chain. A linear epitope is one produced by adjacent amino acid residues in a polypeptide chain. In certain circumstance, an epitope may include moieties of saccharides, phosphoryl groups, or sulfonyl groups on the antigen.

The term "substantial identity" or "substantially identical," when referring to a nucleic acid or fragment thereof, indicates that, when optimally aligned with appropriate nucleotide insertions or deletions with another nucleic acid (or its complementary strand), there is nucleotide sequence identity in at least about 95%, and more preferably at least about 96%, 97%, 98% or 99% of the nucleotide bases, as measured by any well-known algorithm of sequence identity, such as FASTA, BLAST or Gap, as discussed below. A nucleic acid molecule having substantial identity to a reference nucleic acid molecule may, in certain instances, encode a polypeptide having the same or substantially similar amino acid sequence as the polypeptide encoded by the reference nucleic acid molecule.

As applied to polypeptides, the term "substantial similarity" or "substantially similar" means that two peptide sequences, when optimally aligned, such as by the programs GAP or BESTFIT using default gap weights, share at least 95% sequence identity, even more preferably at least 98% or 99% sequence identity. Preferably, residue positions which are not identical differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of similarity may be adjusted upwards to correct for the conservative nature of the substitution. Means for making this adjustment are well-known to those of skill in the art. See, e.g., Pearson (1994) Methods Mol. Biol. 24: 307-331, herein incorporated by reference. Examples of groups of amino acids that have side chains with similar chemical properties include (1) aliphatic side chains: glycine, alanine, valine, leucine and isoleucine; (2) aliphatic-hydroxyl side chains: serine and threonine; (3) amide-containing side chains: asparagine and glutamine; (4) aromatic side chains: phenylalanine, tyrosine, and tryptophan; (5) basic side chains: lysine, arginine, and histidine; (6) acidic side chains: aspartate and glutamate, and (7) sulfur-containing side chains are cysteine and methionine. Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al. (1992) Science 256: 1443-1445, herein incorporated by reference. A "moderately conservative" replacement is any change having a nonnegative value in the PAM250 log-likelihood matrix.

Sequence similarity for polypeptides, which is also referred to as sequence identity, is typically measured using sequence analysis software. Protein analysis software matches similar sequences using measures of similarity assigned to various substitutions, deletions and other modifications, including conservative amino acid substitutions. For instance, GCG software contains programs such as Gap and Bestfit which can be used with default parameters to determine sequence homology or sequence identity between closely related polypeptides, such as homologous polypeptides from different species of organisms or between a wild type protein and a mutein thereof. See, e.g., GCG Version 6.1. Polypeptide sequences also can be compared using FASTA using default or recommended parameters, a program in GCG Version 6.1. FASTA (e.g., FASTA2 and FASTA3) provides alignments and percent sequence identity of the regions of the best overlap between the query and search sequences (Pearson (2000) supra). Another preferred algorithm when comparing a sequence of the invention to a database containing a large number of sequences from different organisms is the computer program BLAST, especially BLASTP or TBLASTN, using default parameters. See, e.g., Altschul et al. (1990) J. Mol. Biol. 215:403-410 and Altschul et al. (1997) Nucleic Acids Res. 25:3389-402, each herein incorporated by reference.

pH-Dependent Binding

The present invention includes anti-PDGFR-beta antibodies with pH-dependent binding characteristics. For example, an anti-PDGFR-beta antibody of the present invention may exhibit reduced binding to PDGFR-beta at acidic pH as compared to neutral pH. Alternatively, anti-PDGFR-beta antibody of the invention may exhibit enhanced binding to its antigen at acidic pH as compared to neutral pH. The expression "acidic pH" includes pH values less than about 6.2, e.g., about 6.0, 5.95, 5.9, 5.85, 5.8, 5.75, 5.7, 5.65, 5.6, 5.55, 5.5, 5.45, 5.4, 5.35, 5.3, 5.25, 5.2, 5.15, 5.1, 5.05, 5.0, or less. As used herein, the expression "neutral pH" means a pH of about 7.0 to about 7.4. The expression "neutral pH" includes pH values of about 7.0, 7.05, 7.1, 7.15, 7.2, 7.25, 7.3, 7.35, and 7.4.

In certain instances, "reduced binding to PDGFR-beta at acidic pH as compared to neutral pH" is expressed in terms of a ratio of the $K_D$ value of the antibody binding to PDGFR-beta at acidic pH to the $K_D$ value of the antibody binding to PDGFR-beta at neutral pH (or vice versa). For example, an antibody or antigen-binding fragment thereof may be regarded as exhibiting "reduced binding to PDGFR-beta at acidic pH as compared to neutral pH" for purposes of the present invention if the antibody or antigen-binding fragment thereof exhibits an acidic/neutral $K_D$ ratio of about 3.0 or greater. In certain exemplary embodiments, the acidic/neutral $K_D$ ratio for an antibody or antigen-binding fragment of the present invention can be about 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 20.0. 25.0, 30.0, 40.0, 50.0, 60.0, 70.0, 100.0 or greater.

Antibodies with pH-dependent binding characteristics may be obtained, e.g., by screening a population of antibodies for reduced (or enhanced) binding to a particular antigen at acidic pH as compared to neutral pH. Additionally, modifications of the antigen-binding domain at the amino acid level may yield antibodies with pH-dependent characteristics. For example, by substituting one or more amino acids of an antigen-binding domain (e.g., within a CDR) with a histidine residue, an antibody with reduced antigen-binding at acidic pH relative to neutral pH may be obtained.

Anti-PDGFR-Beta Antibodies Comprising Fc Variants

According to certain embodiments of the present invention, anti-PDGFR-beta antibodies are provided comprising an Fc domain comprising one or more mutations which enhance or diminish antibody binding to the FcRn receptor, e.g., at acidic pH as compared to neutral pH. For example, the present invention includes anti-PDGFR-beta antibodies comprising a mutation in the $C_H2$ or a $C_H3$ region of the Fc domain, wherein the mutation(s) increases the affinity of the Fc domain to FcRn in an acidic environment (e.g., in an endosome where pH ranges from about 5.5 to about 6.0). Such mutations may result in an increase in serum half-life of the antibody when administered to an animal. Non-limiting examples of such Fc modifications include, e.g., a modification at position 250 (e.g., E or Q); 250 and 428 (e.g., L or F); 252 (e.g., L/Y/F/W or T), 254 (e.g., S or T), and 256 (e.g., S/R/Q/E/D or T); or a modification at position 428 and/or 433 (e.g., H/L/R/S/P/Q or K) and/or 434 (e.g., H/F or Y); or a modification at position 250 and/or 428; or a modification at position 307 or 308 (e.g., 308F, V308F), and 434. In one embodiment, the modification comprises a 428L (e.g., M428L) and 434S (e.g., N434S) modification; a 428L, 259I (e.g., V259I), and 308F (e.g., V308F) modification; a 433K (e.g., H433K) and a 434 (e.g., 434Y) modification; a 252, 254, and 256 (e.g., 252Y, 254T, and 256E) modification; a 250Q and 428L modification (e.g., T250Q and M428L); and a 307 and/or 308 modification (e.g., 308F or 308P).

For example, the present invention includes anti-PDGFR-beta antibodies comprising an Fc domain comprising one or more pairs or groups of mutations selected from the group consisting of: 250Q and 248L (e.g., T250Q and M248L); 252Y, 254T and 256E (e.g., M252Y, S254T and T256E); 428L and 434S (e.g., M428L and N434S); and 433K and 434F (e.g., H433K and N434F). All possible combinations of the foregoing Fc domain mutations, and other mutations within the antibody variable domains disclosed herein, are contemplated within the scope of the present invention.

Biological Characteristics of the Antibodies

The present invention includes anti-PDGFR-beta antibodies and antigen-binding fragments thereof that bind soluble monomeric or dimeric PDGFR-beta molecules with high affinity. For example, the present invention includes antibodies and antigen-binding fragments of antibodies that bind monomeric PDGFR-beta (e.g., at 25° C. or 37° C.) with a $K_D$ of less than about 30 nM as measured by surface plasmon resonance, e.g., using the assay format as defined in Example 3 herein. In certain embodiments, the antibodies or antigen-binding fragments of the present invention bind monomeric PDGFR-beta with a $K_D$ of less than about 25 nM, less than about 20 nM, less than about 15 nM, less than about 10 nM, less than about 5 nM, less than about 2 nM, or less than about 1 nM, as measured by surface plasmon resonance, e.g., using the assay format as defined in Example 3 herein, or a substantially similar assay.

The present invention also includes antibodies and antigen-binding fragments thereof that bind dimeric PDGFR-beta (e.g., at 25° C. or 37° C.) with a $K_D$ of less than about 250 pM as measured by surface plasmon resonance, e.g., using the assay format as defined in Example 3 herein. In certain embodiments, the antibodies or antigen-binding fragments of the present invention bind dimeric PDGFR-beta with a $K_D$ of less than about 240 pM, less than about 230 pM, less than about 220 pM, less than about 210 pM, less than about 200 pM, less than about 190 pM, less than about 180 pM, less than about 170 pM, less than about 160 pM, less than about 150 pM, less than about 140 pM, less than about 130 pM, less than about 120 pM, less than about 110 pM, or less than about 100 pM, as measured by surface plasmon resonance, e.g., using the assay format as defined in Example 3 herein, or a substantially similar assay.

The present invention also includes anti-PDGFR-beta antibodies and antigen-binding fragments thereof that block the binding of one or more PDGF ligand(s) (e.g., PDGF-BB, -AB, -CC, or -DD) to PDGFR-beta. For example, the present invention includes anti-PDGFR-beta antibodies that block the binding of PDGF-BB to monomeric PDGFR-beta in vitro, with an $IC_{50}$ value of less than about 300 pM, as measured by an ELISA-based immunoassay, e.g., using the assay format as defined in Example 4(A) herein, or a real-time bioassay, e.g., using the assay format as defined in Example 4(B), or a substantially similar assay. In certain embodiments, the antibodies or antigen-binding fragments of the present invention block the binding of PDGF-BB to monomeric PDGFR-beta in vitro with an $IC_{50}$ value of less than about 280 pM, less than about 260 pM, less than about 240 pM, less than about 220 pM, less than about 200 pM, less than about 180 pM, less than about 160 pM, less than about 150 pM, less than about 140 pM, less than about 130 pM, less than about 120 pM, less than about 110 pM, less than about 100 pM, less than about 90 pM, less than about 80 pM, or less than about 75 pM, as measured by an ELISA-based immunoassay, e.g., using the assay format as defined in Example 4(A) herein, or a real-time bioassay, e.g., using the assay format as defined in Example 4(B), or a substantially similar assay.

The present invention also includes anti-PDGFR-beta antibodies and antigen-binding fragments thereof that inhibit PDGF ligand-mediated activation of cell surface-expressed PDGFR-beta. For example, the present invention includes anti-PDGFR-beta antibodies and antigen-binding fragments thereof that inhibit PDGF-BB- or PDGF-DD-mediated activation of cell surface-expressed PDGFR-beta, with an $IC_{50}$ value of less than about 500 pM, as measured in a cell-based blocking bioassay, e.g., using the assay format as defined in Example 6 herein, or a substantially similar assay. In certain embodiments, the antibodies or antigen-binding fragments of the present invention block PDGF-BB- or PDGF-DD-mediated activation of cell surface expressed PDGFR-beta with an $IC_{50}$ of less than about 400 pM, less than about 350 pM, less than about 300 pM, less than about 250 pM, less than about 200 pM, less than about 150 pM, less than about 100 pM, less than about 90 pM, less than about 80 pM, less than about 70 pM, less than about 60 pM, less than about 50 pM, less than about 40 pM, or less than about 30 pM, as measured in a cell-based blocking bioassay, e.g., using the assay format as defined in Example 6 herein, or a substantially similar assay.

The present invention also includes anti-PDGFR-beta antibodies and antigen-binding fragments thereof that are internalized into cells expressing PDGFR-beta. For example, the present invention includes anti-PDGFR-beta antibodies and antigen-binding fragments thereof that are effectively internalized into PDGFR-beta-expressing cells as measured using a cell-based antibody internalization assay as defined in Example 7 herein, or a substantially similar assay.

The antibodies of the present invention may possess one or more of the aforementioned biological characteristics, or any combinations thereof. Other biological characteristics of the antibodies of the present invention will be evident to a person of ordinary skill in the art from a review of the present disclosure including the working Examples herein.

Epitope Mapping and Related Technologies

The present invention includes anti-PDGFR-beta antibodies which interact with one or more amino acids found within the extracellular domain of human PDGFR-beta (e.g., within Ig domains 1, 2, 3, 4 and/or 5 of the extracellular domain of PDGFR-beta). Ig domains 1 through 3 (e.g., amino acids 1 through 277 of SEQ ID NO:337) are known to be involved in ligand binding. The present invention includes anti-PDGFR-beta antibodies that interact with one or more amino acids found within Ig domain 1 (e.g., amino acids 1 through 88 of SEQ ID NO:337), Ig domain 2 (e.g., amino acids 97 through 178 of SEQ ID NO:337) and/or Ig domain 3 (e.g., amino acids 182 through 277 of SEQ ID NO:337), and thereby effectively block the receptor/ligand interaction. In certain exemplary embodiments of the present invention, antibodies are provided which specifically interact with Ig domain 2 (e.g., within amino acids 97 through 178 of SEQ ID NO:337; see, e.g., Example 8). The epitope to which the antibodies bind may consist of a single contiguous sequence of 3 or more (e.g., 3, 4, 5, 6, 7, 8, 9, 10, 11, 12, 13, 14, 15, 16, 17, 18, 19, 20 or more) amino acids located within the extracellular domain of PDGFR-beta. Alternatively, the epitope may consist of a plurality of non-contiguous amino acids (or amino acid sequences) located within the extracellular domain of PDGFR-beta.

Various techniques known to persons of ordinary skill in the art can be used to determine whether an antibody "interacts with one or more amino acids" within a polypeptide or protein. Exemplary techniques include, e.g., routine cross-blocking assay such as that described *Antibodies*, Harlow and Lane (Cold Spring Harbor Press, Cold Spring Harb., N.Y.), alanine scanning mutational analysis, peptide blots analysis (Reineke, 2004, Methods Mol Biol 248:443-463), and peptide cleavage analysis. In addition, methods such as epitope excision, epitope extraction and chemical modification of antigens can be employed (Tomer, 2000, Protein Science 9:487-496). Another method that can be used to identify the amino acids within a polypeptide with which an antibody interacts is hydrogen/deuterium exchange detected by mass spectrometry. In general terms, the hydrogen/deuterium exchange method involves deuterium-labeling the protein of interest, followed by binding the antibody to the deuterium-labeled protein. Next, the protein/antibody complex is transferred to water to allow hydrogen-deuterium exchange to occur at all residues except for the residues protected by the antibody (which remain deuterium-labeled). After dissociation of the antibody, the target protein is subjected to protease cleavage and mass spectrometry analysis, thereby revealing the deuterium-labeled residues which correspond to the specific amino acids with which the antibody interacts. See, e.g., Ehring (1999) *Analytical Biochemistry* 267(2):252-259; Engen and Smith (2001) *Anal. Chem.* 73:256 A-265A.

The present invention further includes anti-PDGFR-beta antibodies that bind to the same epitope as any of the specific exemplary antibodies described herein (e.g. H1M3299N, H1M3305N, H1M3310N, H1M3361N, H2M3363N, H2M3365N, H2M3368N, H2M3373N, H2M3374N, H4H3094P, H4H3095S, H4H3096S, H4H3097S, H4H3098S, H4H3099S, H4H3102S, H4H3103S, H4H3104S, H4H3105S, H4H3106S, H4H3107S, etc.). Likewise, the present invention also includes anti-PDGFR-beta antibodies that compete for binding to PDGFR-beta with any of the specific exemplary antibodies described herein (e.g. H1M3299N, H1M3305N, H1M3310N, H1M3361N, H2M3363N, H2M3365N, H2M3368N, H2M3373N, H2M3374N, H4H3094P, H4H3095S, H4H3096S, H4H3097S, H4H3098S, H4H3099S, H4H3102S, H4H3103S, H4H3104S, H4H3105S, H4H3106S, H4H3107S, etc.). For example, the present invention includes anti-PDGFR-beta antibodies that cross-compete for binding to PDGFR-beta with one or more antibodies of "Bin 1" as defined in Example 5 herein (e.g., H4H3365N, H4H3374N, H4H3103S and H4H3094P). The present invention also includes anti-PDGFR-beta antibodies that cross-compete for binding to PDGFR-beta with one or more antibodies of "Bin 2" as defined in Example 5 herein (e.g., H4H3099S, H4H3107S, H4H3305N and H4H3310N).

One can easily determine whether an antibody binds to the same epitope as, or competes for binding with, a reference anti-PDGFR-beta antibody by using routine methods known in the art and exemplified herein. For example, to determine if a test antibody binds to the same epitope as a reference anti-PDGFR-beta antibody of the invention, the reference antibody is allowed to bind to a PDGFR-beta protein (e.g., a soluble portion of the PDGFR-beta extracellular domain or cell surface-expressed PDGFR-beta). Next, the ability of a test antibody to bind to the PDGFR-beta molecule is assessed. If the test antibody is able to bind to PDGFR-beta following saturation binding with the reference anti-PDGFR-beta antibody, it can be concluded that the test antibody binds to a different epitope than the reference anti-PDGFR-beta antibody. On the other hand, if the test antibody is not able to bind to the PDGFR-beta molecule following saturation binding with the reference anti-PDGFR-beta antibody, then the test antibody may bind to the same epitope as the epitope bound by the reference anti-PDGFR-beta antibody of the invention. Additional routine experimentation (e.g., peptide mutation and binding analyses) can then be carried out to confirm whether the observed lack of binding of the test antibody is in fact due to binding to the same epitope as the reference antibody or if steric blocking (or another phenomenon) is responsible for the lack of observed binding. Experiments of this sort can be performed using ELISA, RIA, Biacore, flow cytometry or any other quantitative or qualitative antibody-binding assay available in the art. In accordance with certain embodiments of the present invention, two antibodies bind to the same (or overlapping) epitope if, e.g., a 1-, 5-, 10-, 20- or 100-fold excess of one antibody inhibits binding of the other by at least 50% but preferably 75%, 90% or even 99% as measured in a competitive binding assay (see, e.g., Junghans et al., Cancer Res. 1990:50:1495-1502). Alternatively, two antibodies are deemed to bind to the same epitope if essentially all amino acid mutations in the antigen that reduce or eliminate binding of one antibody reduce or eliminate binding of the other. Two antibodies are deemed to have "overlapping epitopes" if only a subset of the amino acid mutations that reduce or eliminate binding of one antibody reduce or eliminate binding of the other.

To determine if an antibody competes for binding (or cross-competes for binding) with a reference anti-PDGFR-beta antibody, the above-described binding methodology is performed in two orientations: In a first orientation, the reference antibody is allowed to bind to a PDGFR-beta protein (e.g., a soluble portion of the PDGFR-beta extracellular domain or cell surface-expressed PDGFR-beta) under saturating conditions followed by assessment of binding of the test antibody to the PDGFR-beta molecule. In a second orientation, the test antibody is allowed to bind to a PDGFR-beta molecule under saturating conditions followed by assessment of binding of the reference antibody to the PDGFR-beta molecule. If, in both orientations, only the first (saturating) antibody is capable of binding to the PDGFR-beta molecule, then it is concluded that the test antibody and the reference antibody compete for binding to PDGFR-beta (see, e.g., the assay format described in Example 5 herein, in which soluble PDGFR-beta protein is captured onto sensor tips and the PDGFR-beta-coated sensor tips are treated with a reference antibody [mAb#1] and a test anti-PDGFR-beta antibody [mAb#2] sequentially and in both bsinding orders). As will be appreciated by a person of ordinary skill in the art, an antibody that competes for binding with a reference antibody may not necessarily bind to the same epitope as the reference antibody, but may sterically block binding of the reference antibody by binding an overlapping or adjacent epitope.

Preparation of Human Antibodies

Methods for generating monoclonal antibodies, including fully human monoclonal antibodies are known in the art. Any such known methods can be used in the context of the present invention to make human antibodies that specifically bind to human PDGFR-beta.

Using VELOCIMMUNE™ technology, for example, or any other known method for generating fully human monoclonal antibodies, high affinity chimeric antibodies to PDGFR-beta are initially isolated having a human variable region and a mouse constant region. As in the experimental section below, the antibodies are characterized and selected for desirable characteristics, including affinity, selectivity, epitope, etc. If necessary, mouse constant regions are replaced with a desired human constant region, for example wild-type or modified IgG1 or IgG4, to generate a fully human anti-PDGFR-beta antibody. While the constant region selected may vary according to specific use, high affinity antigen-binding and target specificity characteristics reside in the variable region. In certain instances, fully human anti-PDGFR-beta antibodies are isolated directly from antigen-positive B cells.

Bioequivalents

The anti-PDGFR-beta antibodies and antibody fragments of the present invention encompass proteins having amino acid sequences that vary from those of the described antibodies but that retain the ability to bind human PDGFR-beta. Such variant antibodies and antibody fragments comprise one or more additions, deletions, or substitutions of amino acids when compared to parent sequence, but exhibit biological activity that is essentially equivalent to that of the described antibodies. Likewise, the anti-PDGFR-beta antibody-encoding DNA sequences of the present invention encompass sequences that comprise one or more additions, deletions, or substitutions of nucleotides when compared to the disclosed sequence, but that encode an anti-PDGFR-beta antibody or antibody fragment that is essentially bioequivalent to an anti-PDGFR-beta antibody or antibody fragment of the invention. Examples of such variant amino acid and DNA sequences are discussed above.

Two antigen-binding proteins, or antibodies, are considered bioequivalent if, for example, they are pharmaceutical equivalents or pharmaceutical alternatives whose rate and extent of absorption do not show a significant difference when administered at the same molar dose under similar experimental conditions, either single does or multiple dose. Some antibodies will be considered equivalents or pharmaceutical alternatives if they are equivalent in the extent of their absorption but not in their rate of absorption and yet may be considered bioequivalent because such differences in the rate of absorption are intentional and are reflected in the labeling, are not essential to the attainment of effective body drug concentrations on, e.g., chronic use, and are considered medically insignificant for the particular drug product studied.

In one embodiment, two antigen-binding proteins are bioequivalent if there are no clinically meaningful differences in their safety, purity, and potency.

In one embodiment, two antigen-binding proteins are bioequivalent if a patient can be switched one or more times between the reference product and the biological product without an expected increase in the risk of adverse effects, including a clinically significant change in immunogenicity, or diminished effectiveness, as compared to continued therapy without such switching.

In one embodiment, two antigen-binding proteins are bioequivalent if they both act by a common mechanism or mechanisms of action for the condition or conditions of use, to the extent that such mechanisms are known.

Bioequivalence may be demonstrated by in vivo and in vitro methods. Bioequivalence measures include, e.g., (a) an in vivo test in humans or other mammals, in which the concentration of the antibody or its metabolites is measured in blood, plasma, serum, or other biological fluid as a function of time; (b) an in vitro test that has been correlated with and is reasonably predictive of human in vivo bioavailability data; (c) an in vivo test in humans or other mammals in which the appropriate acute pharmacological effect of the antibody (or its target) is measured as a function of time; and (d) in a well-controlled clinical trial that establishes safety, efficacy, or bioavailability or bioequivalence of an antibody.

Bioequivalent variants of anti-PDGFR-beta antibodies of the invention may be constructed by, for example, making various substitutions of residues or sequences or deleting terminal or internal residues or sequences not needed for biological activity. For example, cysteine residues not essential for biological activity can be deleted or replaced with other amino acids to prevent formation of unnecessary or incorrect intramolecular disulfide bridges upon renaturation. In other contexts, bioequivalent antibodies may include anti-PDGFR-beta antibody variants comprising amino acid changes which modify the glycosylation characteristics of the antibodies, e.g., mutations which eliminate or remove glycosylation.

Species Selectivity and Species Cross-Reactivity

The present invention, according to certain embodiments, provides anti-PDGFR-beta antibodies that bind to human PDGFR-beta but not to PDGFR-beta from other species. The present invention also includes anti-PDGFR-beta antibodies that bind to human PDGFR-beta and to PDGFR-beta from one or more non-human species. For example, the anti-PDGFR-beta antibodies of the invention may bind to human PDGFR-beta and may bind or not bind, as the case may be, to one or more of mouse, rat, guinea pig, hamster, gerbil, pig, cat, dog, rabbit, goat, sheep, cow, horse, camel, cynomolgous, marmoset, rhesus or chimpanzee PDGFR-beta. According to certain exemplary embodiments of the present invention, anti-PDGFR-beta antibodies are provided which specifically bind human PDGFR-beta (e.g., monomeric and/or dimeric hPDGFR-beta constructs) and cynomolgus monkey (e.g., *Macaca fascicularis*) PDGFR-beta (e.g., monomeric and/or dimeric mfPDGFR-beta constructs). (See, e.g., Example 3, herein).

Immunoconjugates

The invention encompasses anti-PDGFR-beta monoclonal antibodies conjugated to a therapeutic moiety ("immunoconjugate"), such as a cytotoxin, a chemotherapeutic drug, an immunosuppressant or a radioisotope. Cytotoxic agents include any agent that is detrimental to cells. Examples of suitable cytotoxic agents and chemotherapeutic agents for forming immunoconjugates are known in the art, (see for example, WO 05/103081).

Multispecific Antibodies

The antibodies of the present invention may be monospecific, bi-specific, or multispecific. Multispecific antibodies may be specific for different epitopes of one target polypeptide or may contain antigen-binding domains specific for more than one target polypeptide. See, e.g., Tutt et al., 1991, J. Immunol. 147:60-69; Kufer et al., 2004, Trends Biotechnol. 22:238-244. The anti-PDGFR-beta antibodies of the present invention can be linked to or co-expressed with another functional molecule, e.g., another peptide or protein. For example, an antibody or fragment thereof can be functionally linked (e.g., by chemical coupling, genetic fusion, noncovalent association or otherwise) to one or more other molecular entities, such as another antibody or antibody fragment to produce a bi-specific or a multispecific antibody with a second binding specificity. For example, the present invention includes bi-specific antibodies wherein one arm of an immunoglobulin is specific for human PDGFR-beta or a fragment thereof, and the other arm of the immunoglobulin is specific for a second therapeutic target or is conjugated to a therapeutic moiety.

An exemplary bi-specific antibody format that can be used in the context of the present invention involves the use of a first immunoglobulin (Ig) $C_H3$ domain and a second Ig $C_H3$ domain, wherein the first and second Ig $C_H3$ domains differ from one another by at least one amino acid, and wherein at least one amino acid difference reduces binding of the bispecific antibody to Protein A as compared to a bi-specific antibody lacking the amino acid difference. In one embodiment, the first Ig $C_H3$ domain binds Protein A and the second Ig $C_H3$ domain contains a mutation that reduces or abolishes Protein A binding such as an H95R modification (by IMGT exon numbering; H435R by EU numbering). The second $C_H3$ may further comprise a Y96F modification (by IMGT; Y436F by EU). Further modifications that may be found within the second $C_H3$ include: D16E, L18M, N44S, K52N, V57M, and V82I (by IMGT; D356E, L358M, N384S, K392N, V397M, and V422I by EU) in the case of IgG1 antibodies; N44S, K52N, and V82I (IMGT; N384S, K392N, and V422I by EU) in the case of IgG2 antibodies; and Q15R, N44S, K52N, V57M, R69K, E79Q, and V82I (by IMGT; Q355R, N384S, K392N, V397M, R409K, E419Q, and V422I by EU) in the case of IgG4 antibodies. Variations on the bi-specific antibody format described above are contemplated within the scope of the present invention.

Other exemplary bispecific formats that can be used in the context of the present invention include, without limitation, e.g., scFv-based or diabody bispecific formats, IgG-scFv fusions, dual variable domain (DVD)-Ig, Quadroma, knobs-into-holes, common light chain (e.g., common light chain with knobs-into-holes, etc.), CrossMab, CrossFab, (SEED) body, leucine zipper, Duobody, IgG1/IgG2, dual acting Fab (DAF)-IgG, and Mab[2] bispecific formats (see, e.g., Klein et al. 2012, mAbs 4:6, 1-11, and references cited therein, for a review of the foregoing formats). Bispecific antibodies can also be constructed using peptide/nucleic acid conjugation, e.g., wherein unnatural amino acids with orthogonal chemical reactivity are used to generate site-specific antibody-oligonucleotide conjugates which then self-assemble into multimeric complexes with defined composition, valency and geometry. (See, e.g., Kazane et al., *J. Am. Chem. Soc.* [Epub: Dec. 4, 2012]).

Therapeutic Formulation and Administration

The invention provides pharmaceutical compositions comprising the anti-PDGFR-beta antibodies or antigen-binding fragments thereof of the present invention. The pharmaceutical compositions of the invention are formulated with suitable carriers, excipients, and other agents that provide improved transfer, delivery, tolerance, and the like. A multitude of appropriate formulations can be found in the formulary known to all pharmaceutical chemists: Remington's Pharmaceutical Sciences, Mack Publishing Company, Easton, Pa. These formulations include, for example, powders, pastes, ointments, jellies, waxes, oils, lipids, lipid (cationic or anionic) containing vesicles (such as LIPOFECTIN™, Life Technologies, Carlsbad, Calif.), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA (1998) J Pharm Sci Technol 52:238-311.

The dose of antibody administered to a patient may vary depending upon the age and the size of the patient, target disease, conditions, route of administration, and the like. The preferred dose is typically calculated according to body weight or body surface area. When an antibody of the present invention is used for treating a condition or disease associated with PDGFR-beta activity in an adult patient, it may be advantageous to intravenously administer the antibody of the present invention normally at a single dose of about 0.01 to about 20 mg/kg body weight, more preferably about 0.02 to about 7, about 0.03 to about 5, or about 0.05 to about 3 mg/kg body weight. Depending on the severity of the condition, the frequency and the duration of the treatment can be adjusted. Effective dosages and schedules for administering anti-PDGFR-beta antibodies may be determined empirically; for example, patient progress can be monitored by periodic assessment, and the dose adjusted accordingly. Moreover, interspecies scaling of dosages can be performed using well-known methods in the art (e.g., Mordenti et al., 1991, *Pharmaceut. Res.* 8:1351).

Various delivery systems are known and can be used to administer the pharmaceutical composition of the invention, e.g., encapsulation in liposomes, microparticles, microcapsules, recombinant cells capable of expressing an antibody or other therapeutic protein of the invention, receptor mediated endocytosis (see, e.g., Wu et al., 1987, J. Biol. Chem. 262: 4429-4432). The antibodies and other therapeutically active components of the present invention may also be delivered by gene therapy techniques. Methods of introduction include, but are not limited to, intradermal, intramuscular, intraperitoneal, intravenous, subcutaneous, intranasal, epidural, and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

A pharmaceutical composition of the present invention can be delivered subcutaneously or intravenously with a standard needle and syringe. In addition, with respect to subcutaneous delivery, a pen delivery device readily has applications in delivering a pharmaceutical composition of the present invention. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

Numerous reusable pen and autoinjector delivery devices have applications in the subcutaneous delivery of a pharmaceutical composition of the present invention. Examples include, but are not limited to AUTOPEN™ (Owen Mumford, Inc., Woodstock, UK), DISETRONIC™ pen (Disetronic Medical Systems, Bergdorf, Switzerland), HUMALOG MIX 75/25™ pen, HUMALOG™ pen, HUMALIN 70/30™ pen (Eli Lilly and Co., Indianapolis, Ind.), NOVOPEN™ I, II and III (Novo Nordisk, Copenhagen, Denmark), NOVOPEN JUNIOR™ (Novo Nordisk, Copenhagen, Denmark), BD™ pen (Becton Dickinson, Franklin Lakes, N.J.), OPTIPEN™, OPTIPEN PRO™, OPTIPEN STARLET™, and OPTICLIK™ (sanofi-aventis, Frankfurt, Germany), to name only a few. Examples of disposable pen delivery devices having applications in subcutaneous delivery of a pharmaceutical composition of the present invention include, but are not limited to the SOLOSTAR™ pen (sanofi-aventis), the FLEXPEN™ (Novo Nordisk), and the KWIK-PEN™ (Eli Lilly), the SURECLICK™ Autoinjector (Amgen, Thousand Oaks, Calif.), the PENLET™ (Haselmeier, Stuttgart, Germany), the EPIPEN (Dey, L. P.), and the HUMIRA™ Pen (Abbott Labs, Abbott Park Ill.), to name only a few.

In certain situations, the pharmaceutical composition can be delivered in a controlled release system. In one embodiment, a pump may be used (see Langer, supra; Sefton, 1987, CRC Crit. Ref. Biomed. Eng. 14:201). In another embodiment, polymeric materials can be used; see, Medical Applications of Controlled Release, Langer and Wise (eds.), 1974, CRC Pres., Boca Raton, Fla. In yet another embodiment, a controlled release system can be placed in proximity of the composition's target, thus requiring only a fraction of the systemic dose (see, e.g., Goodson, 1984, in Medical Applications of Controlled Release, supra, vol. 2, pp. 115-138). Other controlled release systems are discussed in the review by Langer, 1990, Science 249:1527-1533.

The injectable preparations may include dosage forms for intravenous, subcutaneous, intracutaneous and intramuscular injections, drip infusions, etc. These injectable preparations may be prepared by methods publicly known. For example, the injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared is preferably filled in an appropriate ampoule.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc. The amount of the aforesaid antibody contained is generally about 5 to about 500 mg per dosage form in a unit dose; especially in the form of injection, it is preferred that the aforesaid antibody is contained in about 5 to about 100 mg and in about 10 to about 250 mg for the other dosage forms.

Therapeutic Uses of the Antibodies

The antibodies of the invention are useful, inter alia, for the treatment, prevention and/or amelioration of any disease or disorder associated with or mediated by PDGFR-beta expression, signaling, or activity, or treatable by blocking the interaction between PDGFR-beta and a PDGFR-beta ligand (e.g., PDGF-BB, PDGF-CC, PDGF-DD, PDGF-AB, etc.) or otherwise inhibiting PDGFR-beta activity and/or signaling. For example, the present invention provides methods for treating eye diseases, fibrotic diseases (fibrosis), vascular diseases and/or cancer (tumor growth inhibition) by administering an anti-PDGFR-beta antibody (or pharmaceutical composition comprising an anti-PDGFR-beta antibody) as described herein to a patient in need of such treatment. In the context of the methods of treatment described herein, the anti-PDGFR-beta antibody may be administered as a monotherapy (i.e., as the only therapeutic agent) or in combination with one or more additional therapeutic agents (examples of which are described elsewhere herein).

Exemplary eye diseases that are treatable by administering the anti-PDGFR-beta antibodies of the invention include age-related macular degeneration (e.g., "wet" AMD), exudative AMD, diabetic retinopathy (e.g., proliferative diabetic retinopathy), retinal venous occlusive diseases such as central retinal vein occlusion (CRVO), iris neovascularization, neovascular glaucoma, post-surgical fibrosis in glaucoma, proliferative vitreoretinopathy (PVR), choroidal neovascularization, optic disc neovascularization, corneal neovascularization, retinal neovascularization, vitreal neovascularization, pannus, pterygium, macular edema, diabetic macular edema (DME), vascular retinopathy, retinal degeneration, uveitis, and inflammatory diseases of the eye.

Exemplary fibrotic diseases that are treatable by administering the anti-PDGFR-beta antibodies of the invention include pulmonary fibrosis (e.g., idiopathic pulmonary fibrosis, bleomycin-induced pulmonary fibrosis, asbestos-induced pulmonary fibrosis, and bronchiolitis obliterans syndrome), chronic asthma, fibrosis associated with acute lung injury and acute respiratory distress (e.g., bacterial pneumonia induced fibrosis, trauma induced fibrosis, viral pneumonia induced fibrosis, ventilator induced fibrosis, non-pulmonary sepsis induced fibrosis and aspiration induced fibrosis), silicosis, radiation-induced fibrosis, chronic obstructive pulmonary disease (COPD), ocular fibrosis (e.g., ocular fibrotic scarring), skin fibrosis (e.g., scleroderma), hepatic fibrosis (e.g., cirrhosis, alcohol-induced liver fibrosis, non-alcoholic steatohepatitis (NASH), bilary duct injury, primary bilary cirrhosis, infection- or viral-induced liver fibrosis [e.g., chronic HCV infection], autoimmune hepatitis), kidney (renal) fibrosis, cardiac fibrosis, atherosclerosis, stent restenosis, and myelofibrosis.

Exemplary vascular diseases that are treatable by administering the anti-PDGFR-beta antibodies of the invention include vasoproliferative diseases, pulmonary arterial hypertension, restenosis, vascular scarring, etc.

The present invention also includes methods for treating cancer, inhibiting tumor growth, promoting tumor regression, inhibiting metastasis, and/or inhibiting pathological angiogenesis (e.g., angiogenesis related to tumor growth) by administering an anti-PDGFR-beta antibody as described herein to a patient in need of such treatment. For example, the antibodies and antigen-binding fragments of the present invention may be used to treat, e.g., primary and/or metastatic tumors arising in the brain and meninges, oropharynx, lung and bronchial tree, gastrointestinal tract, male and female reproductive tract, muscle, bone, skin and appendages, connective tissue, spleen, immune system, blood forming cells and bone marrow, liver and urinary tract, and special sensory organs such as the eye. In certain embodiments, the antibodies and antigen-binding fragments of the invention are used to treat one or more of the following cancers: renal cell carcinoma, pancreatic carcinoma, breast cancer, head and neck cancer (e.g., cancer of the brain, oral cavity, orophyarynx, nasopharynx, hypopharynx, nasal cavity, paranasal sinuses, larynx, lip, etc.), prostate cancer, urinary bladder cancer, malignant gliomas, osteosarcoma, osteoblastoma, osteochondroma, colorectal cancer, gastric cancer (e.g., gastric cancer with MET amplification), malignant mesothelioma, astrocytoma, glioblastoma, medulloblastoma, retinoblastoma, multiple myeloma, ovarian cancer, small cell lung cancer, non-small cell lung cancer, synovial sarcoma, thyroid cancer, connective tissue neoplasms, Kaposi's sarcoma, basal cell carcinoma, squamous cell carcinoma, or melanoma.

Combination Therapies and Formulations

The present invention includes compositions and therapeutic formulations comprising any of the anti-PDGFR-beta antibodies described herein in combination with one or more additional therapeutically active components, and methods of treatment comprising administering such combinations to subjects in need thereof.

The anti-PDGFR-beta antibodies of the present invention may be co-formulated with and/or administered in combination with, e.g., a VEGF antagonist, e.g., a "VEGF-trap" such as aflibercept or other VEGF-inhibiting fusion protein as set forth in U.S. Pat. No. 7,087,411, an anti-VEGF antibody or antigen binding fragment thereof (e.g., bevacizumab, ranibizumab), a small molecule kinase inhibitor of VEGF receptor (e.g., sunitinib, sorafenib or pazopanib), or an anti-VEGF receptor antibody. The anti-PDGFR-beta antibody may also be combined with a PDGF ligand antagonist (e.g., an anti-PDGF-BB antibody, an anti-PDGF-DD antibody, an anti-PDGF-CC antibody, an anti-PDGF-AB antibody, or other PDGF ligand antagonist such as an aptamer [e.g., an anti-PDGF-B aptamer such as Fovista™, Ophthotech Corp., Princeton, N.J.], an antisense molecule, a ribozyme, an siRNA, a peptibody, a nanobody or an antibody fragment directed against a PDGF ligand). In other embodiments, the anti-PDGFR-beta antibodies of the present invention may be co-formulated with and/or administered in combination with an EGFR antagonist (e.g., an anti-EGFR antibody [e.g., cetuximab or panitumumab] or small molecule inhibitor of EGFR [e.g., gefitinib or erlotinib]), an antagonist of another EGFR family member such as Her2/ErbB2, ErbB3 or ErbB4 (e.g., anti-ErbB2, anti-ErbB3 or anti-ErbB4 antibody or small molecule inhibitor of ErbB2, ErbB3 or ErbB4 activity), an antagonist specific for EGFRvIII (e.g., an antibody that specifically binds EGFRvIII), a cMET anagonist (e.g., an anti-cMET antibody), an IGF1R antagonist (e.g., an anti-IGF1R antibody), or a B-raf inhibitor (e.g., vemurafenib, sorafenib, GDC-0879, PLX-4720). In certain instances, the anti-PDGFR-beta antibodies of the present invention are combined, co-formulated and/or administered in combination with a PDGFR-alpha inhibitor (e.g., an anti-PDGFR-alpha antibody), a DLL4 antagonist (e.g., an anti-DLL4 antibody disclosed in US 2009/0142354 such as REGN421), an Ang2 antagonist (e.g., an anti-Ang2 antibody disclosed in US 2011/0027286 such as H1H685P), etc. Other agents that may be beneficially administered in combination with the anti-PDGFR-beta antibodies of the invention include cytokine inhibitors, including small-molecule cytokine inhibitors and antibodies that bind to cytokines such as IL-1, IL-2, IL-3, IL-4, IL-5, IL-6, IL-8, IL-9, IL-11, IL-12, IL-13, IL-17, IL-18, or to their respective receptors.

The anti-PDGFR-beta antibodies of the invention may also be administered and/or co-formulated in combination with antivirals, antibiotics, analgesics, corticosteroids, steroids, oxygen, antioxidants, metal chelators, IFN-gamma, and/or NSAIDs. The anti-PDGFR-beta antibodies of the invention may also be administered as part of a treatment regimen that also includes radiation treatment and/or conventional chemotherapy (e.g., in the context of methods of treating cancer or inhibiting tumor growth).

Any of the aforementioned additional therapeutically active components may be administered in combination with any of the anti-PDGFR-beta antibodies of the present invention for the treatment of any disease or disorder in which administration of an anti-PDGFR-beta antibody is beneficial, including, e.g., any of the eye diseases, fibrotic diseases, vascular diseases and/or cancers mentioned herein. For example, in the context of treating an eye disease (e.g., wet AMD, diabetic retinopathy, CRVO, or any of the other eye diseases described herein), an anti-PDGFR-beta antibody of the present invention may be co-formulated with, and/or administered in combination with a VEGF antagonist, e.g., a "VEGF-trap" such as aflibercept or other VEGF-inhibiting fusion protein as set forth in U.S. Pat. No. 7,087,411, or an anti-VEGF antibody or antigen binding fragment thereof (e.g., bevacizumab, or ranibizumab).

In exemplary embodiments in which an anti-PDGFR-beta antibody of the invention is administered in combination with a VEGF antagonist (e.g., a VEGF trap such as aflibercept), including administration of co-formulations comprising an anti-PDGFR-beta antibody and a VEGF antagonist, the individual components may be administered to a subject and/or co-formulated using a variety of dosage combinations. For example, the anti-PDGFR-beta antibody may be administered to a subject and/or contained in a co-formulation in an amount selected from the group consisting of 0.05 mg, 0.1 mg, 0.2 mg, 0.3 mg, 0.4 mg, 0.5 mg, 0.6 mg, 0.7 mg, 0.8 mg, 0.9 mg, 1.0 mg, 1.5 mg, 2.0 mg, 2.5 mg, 3.0 mg, 3.5 mg, 4.0 mg, 4.5 mg, 5.0 mg, and 5.5 mg; and the VEGF antagonist (e.g., a VEGF trap such as aflibercept) may be administered to the subject and/or contained in a co-formulation in an amount selected from the group consisting of 1.0 mg, 1.1 mg, 1.2 mg, 1.3 mg, 1.4 mg, 1.5 mg, 1.6 mg, 1.7 mg, 1.8 mg, 1.9 mg, 2.0 mg, 2.1 mg, 2.2 mg, 2.3 mg, 2.4 mg, 2.5 mg, 2.6 mg, 2.7 mg, 2.8 mg, 2.9 mg and 3.0 mg. Exemplary anti-PDGFR-beta antibody/aflibercept dosage combinations of the present invention include, e.g.: (i) 0.2 mg anti-PDGFR-beta antibody+2 mg aflibercept; (ii) 0.5 mg anti-PDGFR-beta antibody+2 mg aflibercept; (iii) 1 mg anti-PDGFR-beta antibody+2 mg aflibercept; (iv) 3 mg anti-PDGFR-beta antibody+2 mg aflibercept; and (v) 4 mg anti-PDGFR-beta antibody+2 mg aflibercept. The combinations/co-formulations may be administered to a subject according to any of the administration regimens disclosed elsewhere herein, including, e.g., once every week, once every 2 weeks, once every 3 weeks, once every month, once every 2 months, once every 3 months, once every 4 months, once every 5 months, once every 6 months, etc.

The additional therapeutically active component(s) may be administered to a subject prior to administration of an anti-PDGFR-beta antibody of the present invention. For example, a first component may be deemed to be administered "prior to" a second component if the first component is administered 1 week before, 72 hours before, 60 hours before, 48 hours before, 36 hours before, 24 hours before, 12 hours before, 6 hours before, 5 hours before, 4 hours before, 3 hours before, 2 hours before, 1 hour before, 30 minutes before, 15 minutes before, 10 minutes before, 5 minutes before, or less than 1 minute before administration of the second component. In other embodiments, the additional therapeutically active component(s) may be administered to a subject after administration of an anti-PDGFR-beta antibody of the present invention. For example, a first component may be deemed to be administered "after" a second component if the first component is administered 1 minute after, 5 minutes after, 10 minutes after, 15 minutes after, 30 minutes after, 1 hour after, 2 hours after, 3 hours after, 4 hours after, 5 hours after, 6 hours after, 12 hours after, 24 hours after, 36 hours after, 48 hours after, 60 hours after, 72 hours after administration of the second component. In yet other embodiments, the additional therapeutically active component(s) may be administered to a subject concurrent with administration of an anti-PDGFR-beta antibody of the present invention. "Concurrent" administration, for purposes of the present invention, includes, e.g., administration of an anti-PDGFR-beta antibody and an additional therapeutically active component to a subject in a single dosage form (e.g., co-formulated), or in separate dosage forms administered to the subject within about 30 minutes or less of each other. If administered in separate dosage forms, each dosage form may be administered via the same route (e.g., both the anti-PDGFR-beta antibody and the additional therapeutically active component may be administered intravitreally, subcutaneously, etc.); alternatively, each dosage form may be administered via a different route (e.g., the anti-PDGFR-beta antibody may be administered Intravitreally, and the additional therapeutically active component may be administered systemically). In any event, administering the components in a single dosage from, in separate dosage forms by the same route, or in separate dosage forms by different routes are all considered "concurrent administration," for purposes of the present disclosure. For purposes of the present disclosure, administration of an anti-PDGFR-beta antibody "prior to", "concurrent with," or "after" (as those terms are defined herein above) administration of an additional therapeutically active component is considered administration of an anti-PDGFR-beta antibody "in combination with" an additional therapeutically active component).

The present invention includes pharmaceutical compositions in which an anti-PDGFR-beta antibody of the present invention is co-formulated with one or more of the additional therapeutically active component(s) as described elsewhere herein.

The present invention also includes additional therapeutic compositions comprising a combination of a PDGF antagonist and a VEGF antagonist. PDGF antagonists according to this aspect of the invention include PDGF receptor antagonists as well as PDGF ligand antagonists. Likewise, VEGF antagonists according to this aspect of the invention include VEGF receptor antagonists as well as VEGF ligand antagonists.

Administration Regimens

According to certain embodiments of the present invention, multiple doses of an anti-PDGFR-beta antibody (or a pharmaceutical composition comprising a combination of an anti-PDGFR-beta antibody and any of the additional therapeutically active agents mentioned herein) may be administered to a subject over a defined time course. The methods according to this aspect of the invention comprise sequentially administering to a subject multiple doses of an anti-PDGFR-beta antibody of the invention. As used herein, "sequentially administering" means that each dose of anti-PDGFR-beta antibody is administered to the subject at a different point in time, e.g., on different days separated by a predetermined interval (e.g., hours, days, weeks or months). The present invention includes methods which comprise sequentially administering to the patient a single initial dose of an anti-PDGFR-beta antibody, followed by one or more secondary doses of the anti-PDGFR-beta antibody, and optionally followed by one or more tertiary doses of the anti-PDGFR-beta antibody.

The terms "initial dose," "secondary doses," and "tertiary doses," refer to the temporal sequence of administration of the anti-PDGFR-beta antibody of the invention. Thus, the "initial dose" is the dose which is administered at the beginning of the treatment regimen (also referred to as the "baseline dose"); the "secondary doses" are the doses which are administered after the initial dose; and the "tertiary doses" are the doses which are administered after the secondary doses. The initial, secondary, and tertiary doses may all contain the same amount of anti-PDGFR-beta antibody, but generally may differ from one another in terms of frequency of administration. In certain embodiments, however, the amount of anti-PDGFR-beta antibody contained in the initial, secondary and/or tertiary doses varies from one another (e.g., adjusted up or down as appropriate) during the course of treatment. In certain embodiments, two or more (e.g., 2, 3, 4, or 5) doses are administered at the beginning of the treatment regimen as "loading doses" followed by subsequent doses that are administered on a less frequent basis (e.g., "maintenance doses").

In certain exemplary embodiments of the present invention, each secondary and/or tertiary dose is administered 1 to 26 (e.g., 1, 1½, 2, 2½, 3, 3½, 4, 4½, 5, 5½, 6, 6½, 7, 7½, 8, 8½, 9, 9½, 10, 10½, 11, 11½, 12, 12½, 13, 13½, 14, 14½, 15, 15½, 16, 16½, 17, 17½, 18, 18½, 19, 19½, 20, 20½, 21, 21½, 22, 22½, 23, 23½, 24, 24½, 25, 25½, 26, 26½, or more) weeks after the immediately preceding dose. The phrase "the immediately preceding dose," as used herein, means, in a sequence of multiple administrations, the dose of anti-PDGFR-beta antibody which is administered to a patient prior to the administration of the very next dose in the sequence with no intervening doses.

The methods according to this aspect of the invention may comprise administering to a patient any number of secondary and/or tertiary doses of an anti-PDGFR-beta antibody. For example, in certain embodiments, only a single secondary dose is administered to the patient. In other embodiments, two or more (e.g., 2, 3, 4, 5, 6, 7, 8, or more) secondary doses are administered to the patient. Likewise, in certain embodiments, only a single tertiary dose is administered to the patient. In other embodiments, two or more (e.g., 2, 3, 4, 5, 6, 7, 8, or more) tertiary doses are administered to the patient.

In embodiments involving multiple secondary doses, each secondary dose may be administered at the same frequency as the other secondary doses. For example, each secondary dose may be administered to the patient 1 to 2 weeks or 1 to 2 months after the immediately preceding dose. Similarly, in embodiments involving multiple tertiary doses, each tertiary dose may be administered at the same frequency as the other tertiary doses. For example, each tertiary dose may be administered to the patient 2 to 12 weeks after the immediately preceding dose. In certain embodiments of the invention, the frequency at which the secondary and/or tertiary doses are administered to a patient can vary over the course of the treatment regimen. The frequency of administration may also be adjusted during the course of treatment by a physician depending on the needs of the individual patient following clinical examination.

The present invention includes administration regimens in which 2 to 6 loading doses are administered to a patient at a first frequency (e.g., once a week, once every two weeks, once every three weeks, once a month, once every two months, etc.), followed by administration of two or more maintenance doses to the patient on a less frequent basis. For example, according to this aspect of the invention, if the loading doses are administered at a frequency of, e.g., once a month (e.g., two, three, four, or more loading doses administered once a month), then the maintenance doses may be administered to the patient once every five weeks, once every six weeks, once every seven weeks, once every eight weeks, once every ten weeks, once every twelve weeks, etc.).

Diagnostic Uses of the Antibodies

The anti-PDGFR-beta antibodies of the present invention may also be used to detect and/or measure PDGFR-beta, or PDGFR-beta-expressing cells in a sample, e.g., for diagnostic purposes. For example, an anti-PDGFR-beta antibody, or fragment thereof, may be used to diagnose a condition or disease characterized by aberrant expression (e.g., over-expression, under-expression, lack of expression, etc.) of PDGFR-beta. Exemplary diagnostic assays for PDGFR-beta may comprise, e.g., contacting a sample, obtained from a patient, with an anti-PDGFR-beta antibody of the invention, wherein the anti-PDGFR-beta antibody is labeled with a detectable label or reporter molecule. Alternatively, an unlabeled anti-PDGFR-beta antibody can be used in diagnostic applications in combination with a secondary antibody which is itself detectably labeled. The detectable label or reporter molecule can be a radioisotope, such as $^3$H, $^{14}$C, $^{32}$P, $^{35}$S, or $^{125}$I; a fluorescent or chemiluminescent moiety such as fluorescein isothiocyanate, or rhodamine; or an enzyme such as alkaline phosphatase, beta-galactosidase, horseradish peroxidase, or luciferase. Specific exemplary assays that can be used to detect or measure PDGFR-beta in a sample include enzyme-linked immunosorbent assay (ELISA), radioimmunoassay (RIA), and fluorescence-activated cell sorting (FACS).

Samples that can be used in PDGFR-beta diagnostic assays according to the present invention include any tissue or fluid sample obtainable from a patient which contains detectable quantities of PDGFR-beta protein, or fragments thereof, under normal or pathological conditions. Generally, levels of PDGFR-beta in a particular sample obtained from a healthy patient (e.g., a patient not afflicted with a disease or condition associated with abnormal PDGFR-beta levels or activity) will be measured to initially establish a baseline, or standard, level of PDGFR-beta. This baseline level of PDGFR-beta can then be compared against the levels of PDGFR-beta measured in samples obtained from individuals suspected of having a PDGFR-beta related disease or condition.

EXAMPLES

The following examples are put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1

Generation of Human Antibodies to PDGFR-Beta

An immunogen comprising the PDGFR-beta ecto domain was administered directly, with an adjuvant to stimulate the immune response, to a VELOCIMMUNE® mouse comprising DNA encoding human Immunoglobulin heavy and kappa light chain variable regions. The antibody immune response was monitored by a PDGFR-beta-specific immunoassay. When a desired immune response was achieved splenocytes were harvested and fused with mouse myeloma cells to preserve their viability and form hybridoma cell lines. The hybridoma cell lines were screened and selected to identify cell lines that produce PDGFR-beta-specific antibodies. Using this technique several anti-PDGFR-beta chimeric antibodies (i.e., antibodies possessing human variable domains and mouse constant domains) were obtained; exemplary antibodies generated in this manner were designated as follows: H1M3299N, H1M3305N, H1M3310N, H1M3361N, H2M3363N, H2M3365N, H2M3368N, H2M3373N and H2M3374N. The human variable domains from the chimeric antibodies were subsequently cloned onto human constant domains to make fully human anti-PDGFR-beta antibodies as described herein.

Anti-PDGFR-beta antibodies were also isolated directly from antigen-positive B cells without fusion to myeloma cells, as described in US 2007/0280945A1. Using this method, several fully human anti-PDGFR-beta antibodies (i.e., antibodies possessing human variable domains and human constant domains) were obtained; exemplary antibodies generated in this manner were designated as follows: H4H3394P, H4H3095S, H4H3096S, H4H3097S, H4H3098S, H4H3099S, H4H3102S, H4H3103S, H4H3104S, H4H3105S, H4H3106S, H4H3107S.

Certain biological properties of the exemplary anti-PDGFR-beta antibodies generated in accordance with the methods of this Example are described in detail in the Examples set forth below.

Example 2

Heavy and Light Chain Variable Region Amino Acid Sequences

Table 1 sets forth the heavy and light chain variable region amino acid sequence pairs of selected anti-PDGFR-beta antibodies and their corresponding antibody identifiers.

TABLE 1

| Antibody Designation | SEQ ID NOs: | | | | | | | |
|---|---|---|---|---|---|---|---|---|
| | HCVR | HCDR1 | HCDR2 | HCDR3 | LCVR | LCDR1 | LCDR2 | LCDR3 |
| 3299N | 2 | 4 | 6 | 8 | 10 | 12 | 14 | 16 |
| 3305N | 18 | 20 | 22 | 24 | 26 | 28 | 30 | 32 |
| 3310N | 34 | 36 | 38 | 40 | 42 | 44 | 46 | 48 |
| 3361N | 50 | 52 | 54 | 56 | 58 | 60 | 62 | 64 |
| 3363N | 66 | 68 | 70 | 72 | 74 | 76 | 78 | 80 |
| 3365N | 82 | 84 | 86 | 88 | 90 | 92 | 94 | 96 |
| 3368N | 98 | 100 | 102 | 104 | 106 | 108 | 110 | 112 |
| 3373N | 114 | 116 | 118 | 120 | 122 | 124 | 126 | 128 |
| 3374N | 130 | 132 | 134 | 136 | 138 | 140 | 142 | 144 |
| 3094P | 146 | 148 | 150 | 152 | 154 | 156 | 158 | 160 |

TABLE 1-continued

| Antibody Designation | SEQ ID NOs: | | | | | | | |
|---|---|---|---|---|---|---|---|---|
| | HCVR | HCDR1 | HCDR2 | HCDR3 | LCVR | LCDR1 | LCDR2 | LCDR3 |
| 3095S | 162 | 164 | 166 | 168 | 170 | 172 | 174 | 176 |
| 3096S | 178 | 180 | 182 | 184 | 186 | 188 | 190 | 192 |
| 3097S | 194 | 196 | 198 | 200 | 202 | 204 | 206 | 208 |
| 3098S | 210 | 212 | 214 | 216 | 218 | 220 | 222 | 224 |
| 3099S | 226 | 228 | 230 | 232 | 234 | 236 | 238 | 240 |
| 3102S | 242 | 244 | 246 | 248 | 250 | 252 | 254 | 256 |
| 3103S | 258 | 260 | 262 | 264 | 266 | 268 | 270 | 272 |
| 3104S | 274 | 276 | 278 | 280 | 282 | 284 | 286 | 288 |
| 3105S | 290 | 292 | 294 | 296 | 298 | 300 | 302 | 304 |
| 3106S | 306 | 308 | 310 | 312 | 314 | 316 | 318 | 320 |
| 3107S | 322 | 324 | 326 | 328 | 330 | 332 | 334 | 336 |

Antibodies are typically referred to herein according to the following nomenclature: Fc prefix (e.g. "H1M," "H2M," "H4H"), followed by a numerical identifier (e.g. "3299," "3363," or "3094" as shown in Table 1), followed by a "P," "N" or "S" suffix. Thus, according to this nomenclature, an antibody may be referred to herein as, e.g., "H1M3299N," "H2M3363N," "H4H3094," etc. The H1M, H2M and H4H prefixes on the antibody designations used herein indicate the particular Fc region isotype of the antibody. For example, an "H1M" antibody has a mouse IgG1 Fc, whereas an "H4H" antibody has a human IgG4 Fc. As will be appreciated by a person of ordinary skill in the art, an antibody having a particular Fc isotype can be converted to an antibody with a different Fc isotype (e.g., an antibody with a mouse IgG1 Fc can be converted to an antibody with a human IgG4 Fc, etc.), but in any event, the variable domains (including the CDRs)—which are indicated by the numerical identifiers shown in Table 1—will remain the same, and the binding properties are expected to be identical or substantially similar regardless of the nature of the Fc domain.

Control Construct Used in the Following Examples

An anti-PDGFR-beta control antibody was included in the following Examples for comparative purposes. The control antibody is designated herein as Control I: a human anti-PDGFR-beta antibody with heavy and light chain variable domain sequences of "2C5" as set forth in U.S. Pat. No. 7,740,850.

Example 3

Antibody Binding to Human PDGFR-Beta as Determined by Surface Plasmon Resonance

Binding affinities and kinetic constants for antigen binding to selected purified anti-human PDGFR-beta monoclonal antibodies were determined using a real-time surface plasmon resonance biosensor (Biacore T100, GE Healthcare Life Sciences, Piscataway, N.J.) assay at 25° C. and 37° C. Antibodies, expressed as either mouse Fc (prefix H1M; H2M) or human Fc (prefix H4H), were captured on their respective anti-Fc sensor surfaces (Mab capture format). Different concentrations of soluble monomeric PDGFR-beta constructs (hPDGFRb.mmh [SEQ ID NO:337], *Macaca fascicularis* PDGFRb.mmh [SEQ ID NO:340]) or dimeric PDGFR-beta constructs (human PDGFRb.mFc [SEQ ID NO:338] or human PDGFRb.hFc [SEQ ID NO:339]) were injected over the anti-PDFR-beta monoclonal antibody captured surface at a flow rate of 50 μL/min. Kinetic association ($k_a$) and dissociation ($k_d$) rate constants were determined by processing and fitting the data to a 1:1 binding model using Scrubber 2.0 curve fitting software. Binding dissociation equilibrium constants ($K_D$) and dissociative half-lives ($t_{1/2}$) were calculated from the kinetic rate constants as: $K_D$ (M)=$k_d/k_a$; and $t_{1/2}$ (min)=(ln2/(60*$k_d$). Kinetic binding parameters for different anti-PDGFR-beta monoclonal antibodies are shown in Tables 2 to 5. (NB=no binding observed under the conditions used; NT=not tested).

TABLE 2

Binding Characteristics of Anti-PDGFR-beta Antibodies (Mouse Fc Format) to Monomeric and Dimeric PDGFR-beta constructs at 25° C.

| Antibody | Analyte | ka (Ms$^{-1}$) | kd (s$^{-1}$) | $K_D$ (Molar) | $t_{1/2}$ (min) |
|---|---|---|---|---|---|
| H1M3305N | hPDGFRb.mmh | 3.12E+04 | 2.52E−05 | 8.08E−10 | 458 |
| | mfPDGFRb.mmh | 5.10E+04 | 4.16E−05 | 8.16E−10 | 278 |
| | hPDGFRb.mFc | 1.62E+05 | 1.00E−06 | 6.18E−12 | 11550 |
| H1M3310N | hPDGFRb.mmh | 1.40E+04 | 1.00E−06 | 7.00E−11 | 11550 |
| | mfPDGFRb.mmh | 1.00E+04 | 1.00E−06 | 2.00E−10 | 11550 |
| | hPDGFRb.mFc | 1.27E+04 | 1.00E−06 | 7.89E−11 | 11550 |
| H1M3299N | hPDGFRb.mmh | 2.11E+04 | 9.20E−04 | 4.35E−08 | 13 |
| | mfPDGFRb.mmh | NB | NB | NB | NB |
| | hPDGFRb.mFc | 2.59E+04 | 1.65E−04 | 6.35E−09 | 70 |
| H1M3361N | hPDGFRb.mmh | 1.73E+05 | 1.26E−03 | 7.29E−09 | 9 |
| | mfPDGFRb.mmh | 1.00E+04 | 3.89E−05 | 3.90E−09 | 297 |
| | hPDGFRb.mFc | 1.31E+04 | 1.00E−06 | 7.65E−11 | 11550 |
| H2M3363N | hPDGFRb.mmh | 7.11E+04 | 3.33E−03 | 4.68E−08 | 3 |
| | mfPDGFRb.mmh | 5.00E+04 | 6.85E−05 | 1.40E−09 | 169 |
| | hPDGFRb.mFc | 1.04E+05 | 4.03E−06 | 3.86E−11 | 2867 |
| H2M3365N | hPDGFRb.mmh | 4.54E+04 | 1.27E−04 | 2.79E−09 | 91 |
| | mfPDGFRb.mmh | 6.00E+04 | 2.06E−04 | 3.40E−09 | 56 |
| | hPDGFRb.mFc | 2.36E+05 | 8.01E−05 | 3.40E−10 | 144 |

TABLE 2-continued

Binding Characteristics of Anti-PDGFR-beta Antibodies (Mouse Fc Format) to Monomeric and Dimeric PDGFR-beta constructs at 25° C.

| Antibody | Analyte | ka (Ms$^{-1}$) | kd (s$^{-1}$) | K$_D$ (Molar) | t$_{1/2}$ (min) |
|---|---|---|---|---|---|
| H2M3368N | hPDGFRb.mmh | 4.61E+04 | 3.41E−04 | 7.41E−09 | 34 |
|  | mfPDGFRb.mmh | 7.00E+03 | 1.85E−04 | 3.00E−08 | 63 |
|  | hPDGFRb.mFc | 1.18E+05 | 3.70E−05 | 3.13E−10 | 313 |
| H2M3373N | hPDGFRb.mmh | 1.89E+05 | 2.35E−03 | 1.24E−08 | 5 |
|  | mfPDGFRb.mmh | 1.30E+05 | 2.38E−03 | 1.83E−08 | 5 |
|  | hPDGFRb.mFc | 4.73E+05 | 2.40E−04 | 5.07E−10 | 48 |
| H1M3374N | hPDGFRb.mmh | 1.67E+05 | 3.31E−04 | 1.99E−09 | 35 |
|  | mfPDGFRb.mmh | 1.37E+05 | 3.71E−04 | 2.70E−09 | 31 |
|  | hPDGFRb.mFc | 9.96E+05 | 1.07E−04 | 1.08E−10 | 108 |

TABLE 3

Binding Characteristics of Anti-PDGFR-beta Antibodies (Human Fc Format) to Monomeric and Dimeric PDGFR-beta constructs at 25° C.

| Antibody | Analyte | ka (Ms$^{-1}$) | kd (s$^{-1}$) | K$_D$ (Molar) | t$_{1/2}$ (min) |
|---|---|---|---|---|---|
| H4H3305N | hPDGFRb.mmh | 5.99E+04 | 1.09E−04 | 1.81E−09 | 106 |
|  | mfPDGFRb.mmh | 6.12E+04 | 1.11E−04 | 1.82E−09 | 104 |
|  | hPDGFRb.hFc | 1.38E+05 | 3.42E−05 | 2.48E−10 | 338 |
| H4H3310N | hPDGFRb.mmh | 2.61E+04 | 8.92E−05 | 3.41E−09 | 130 |
|  | mfPDGFRb.mmh | 2.88E+04 | 1.08E−04 | 3.75E−09 | 107 |
|  | hPDGFRb.hFc | 4.45E+04 | 2.90E−05 | 6.52E−10 | 398 |
| H4H3365N | hPDGFRb.mmh | 8.53E+04 | 1.42E−04 | 1.66E−09 | 81 |
|  | mfPDGFRb.mmh | 8.83E+04 | 1.50E−04 | 1.70E−09 | 77 |
|  | hPDGFRb.hFc | 1.84E+05 | 4.55E−05 | 2.44E−10 | 254 |
| H4H3374N | hPDGFRb.mmh | 2.83E+05 | 3.58E−04 | 1.26E−09 | 32 |
|  | mfPDGFRb.mmh | 2.84E+05 | 4.72E−04 | 1.66E−09 | 24 |
|  | hPDGFRb.hFc | 6.00E+05 | 8.93E−05 | 1.48E−10 | 129 |
| H4H3107S | hPDGFRb.mmh | 2.21E+05 | 1.91E−04 | 8.63E−10 | 61 |
|  | mfPDGFRb.mmh | 2.36E+05 | 1.98E−04 | 8.36E−10 | 58 |
|  | hPDGFRb.hFc | 5.29E+05 | 4.24E−05 | 8.01E−11 | 272 |
| H4H3102S | hPDGFRb.mmh | 5.09E+05 | 4.55E−04 | 8.90E−10 | 25 |
|  | mfPDGFRb.mmh | 2.83E+05 | 4.89E−04 | 1.73E−09 | 24 |
|  | hPDGFRb.hFc | 3.00E+05 | 1.18E−04 | 3.90E−10 | 98 |
| H4H3099S | hPDGFRb.mmh | 1.45E+05 | 1.69E−04 | 1.16E−09 | 68 |
|  | mfPDGFRb.mmh | 1.66E+05 | 1.64E−04 | 9.87E−10 | 71 |
|  | hPDGFRb.hFc | 2.38E+05 | 5.48E−05 | 2.30E−10 | 211 |
| H4H3098S | hPDGFRb.mmh | 3.86E+05 | 5.96E−04 | 1.54E−09 | 19 |
|  | mfPDGFRb.mmh | 1.36E+05 | 9.40E−03 | 6.89E−08 | 1.2 |
|  | hPDGFRb.hFc | 2.80E+05 | 6.22E−05 | 2.19E−10 | 186 |
| H4H3104S | hPDGFRb.mmh | 4.28E+05 | 6.88E−04 | 1.61E−09 | 17 |
|  | mfPDGFRb.mmh | 7.86E+05 | 7.14E−04 | 9.09E−10 | 16 |
|  | hPDGFRb.hFc | 4.80E+05 | 1.46E−04 | 3.04E−10 | 79 |
| H4H3094P | hPDGFRb.mmh | 1.65E+05 | 2.57E−04 | 1.56E−09 | 45 |
|  | mfPDGFRb.mmh | 1.77E+05 | 2.89E−04 | 1.63E−09 | 40 |
|  | hPDGFRb.hFc | 2.42E+05 | 6.20E−05 | 2.56E−10 | 186 |
| H4H3103S | hPDGFRb.mmh | 3.35E+05 | 1.05E−03 | 3.13E−09 | 11 |
|  | mfPDGFRb.mmh | 3.59E+05 | 1.16E−03 | 3.24E−09 | 10 |
|  | hPDGFRb.hFc | 6.21E+05 | 1.64E−04 | 2.64E−10 | 70 |
| H4H3106S | hPDGFRb.mmh | 2.99E+05 | 7.44E−04 | 2.49E−09 | 16 |
|  | mfPDGFRb.mmh | 1.90E+05 | 8.82E−04 | 4.65E−09 | 13 |
|  | hPDGFRb.hFc | 3.14E+05 | 2.15E−04 | 6.86E−10 | 54 |
| H4H3105S | hPDGFRb.mmh | 2.46E+05 | 7.84E−04 | 3.19E−09 | 15 |
|  | mfPDGFRb.mmh | 1.80E+05 | 9.32E−04 | 5.20E−09 | 12 |
|  | hPDGFRb.hFc | 2.47E+05 | 2.25E−04 | 9.10E−10 | 51 |
| H4H3095S | hPDGFRb.mmh | 2.85E+05 | 1.36E−03 | 4.78E−09 | 8 |
|  | mfPDGFRb.mmh | 2.07E+05 | 1.75E−03 | 8.50E−09 | 7 |
|  | hPDGFRb.hFc | 3.21E+05 | 2.32E−04 | 7.20E−10 | 50 |
| H4H3096S | hPDGFRb.mmh | 2.81E+05 | 1.04E−03 | 3.68E−09 | 11 |
|  | mfPDGFRb.mmh | 1.82E+05 | 1.17E−03 | 6.39E−09 | 10 |
|  | hPDGFRb.hFc | 2.22E+05 | 2.60E−04 | 1.17E−09 | 44 |
| H4H3097S | hPDGFRb.mmh | NB | NB | NB | NB |
|  | mfPDGFRb.mmh | NB | NB | NB | NB |
|  | hPDGFRb.hFc | NB | NB | NB | NB |
| Control I | hPDGFRb.mmh | 2.77E+05 | 3.49E−03 | 1.26E−08 | 3 |
|  | mfPDGFRb.mmh | 3.02E+05 | 2.43E−03 | 8.06E−09 | 5 |
|  | hPDGFRb.hFc | 5.39E+05 | 1.50E−04 | 2.78E−10 | 77 |

TABLE 4

Binding Characteristics of Anti-PDGFR-beta Antibodies (Mouse Fc Format) to Monomeric and Dimeric PDGFR-beta constructs at 37° C.

| Antibody | Analyte | ka (Ms$^{-1}$) | kd (s$^{-1}$) | $K_D$ (Molar) | $t_{1/2}$ (min) |
|---|---|---|---|---|---|
| H1M3305N | hPDGFRb.mmh | 1.16E+05 | 1.02E−04 | 8.80E−10 | 113 |
|  | mfPDGFRb.mmh | NT | NT | NT | NT |
|  | hPDGFRb.mFc | NT | NT | NT | NT |
| H1M3310N | hPDGFRb.mmh | 3.53E+04 | 6.46E−05 | 1.83E−09 | 179 |
|  | mfPDGFRb.mmh | NT | NT | NT | NT |
|  | hPDGFRb.mFc | NT | NT | NT | NT |
| H1M3299N | hPDGFRb.mmh | 3.16E+04 | 2.17E−03 | 6.86E−08 | 5 |
|  | mfPDGFRb.mmh | NT | NT | NT | NT |
|  | hPDGFRb.mFc | NT | NT | NT | NT |
| H1M3361N | hPDGFRb.mmh | 3.04E+05 | 8.33E−03 | 2.74E−08 | 1.4 |
|  | mfPDGFRb.mmh | NT | NT | NT | NT |
|  | hPDGFRb.mFc | NT | NT | NT | NT |
| H2M3363N | hPDGFRb.mmh | 2.86E+05 | 5.03E−03 | 1.76E−08 | 2 |
|  | mfPDGFRb.mmh | NT | NT | NT | NT |
|  | hPDGFRb.mFc | NT | NT | NT | NT |
| H2M3365N | hPDGFRb.mmh | 1.15E+05 | 5.51E−04 | 4.79E−09 | 21 |
|  | mfPDGFRb.mmh | NT | NT | NT | NT |
|  | hPDGFRb.mFc | NT | NT | NT | NT |
| H2M3368N | hPDGFRb.mmh | 1.37E+05 | 8.44E−04 | 6.17E−09 | 14 |
|  | mfPDGFRb.mmh | NT | NT | NT | NT |
|  | hPDGFRb.mFc | NT | NT | NT | NT |
| H2M3373N | hPDGFRb.mmh | 4.10E+05 | 1.22E−02 | 2.98E−08 | 0.9 |
|  | mfPDGFRb.mmh | NT | NT | NT | NT |
|  | hPDGFRb.mFc | NT | NT | NT | NT |
| H1M3374N | hPDGFRb.mmh | 4.63E+05 | 7.90E−04 | 1.71E−09 | 15 |
|  | mfPDGFRb.mmh | NT | NT | NT | NT |
|  | hPDGFRb.mFc | NT | NT | NT | NT |

TABLE 5

Binding Characteristics of Anti-PDGFR-beta Antibodies (Human Fc Format) to Monomeric and Dimeric PDGFR-beta constructs at 37° C.

| Antibody | Analyte | ka (Ms$^{-1}$) | kd (s$^{-1}$) | $K_D$ (Molar) | $t_{1/2}$ (min) |
|---|---|---|---|---|---|
| H4H3305N | hPDGFRb.mmh | 1.84E+05 | 3.55E−04 | 1.93E−09 | 33 |
|  | mfPDGFRb.mmh | 1.91E+05 | 3.90E−04 | 2.04E−09 | 30 |
|  | hPDGFRb.hFc | 2.47E+05 | 4.85E−05 | 1.97E−10 | 238 |
| H4H3310N | hPDGFRb.mmh | 5.09E+04 | 3.39E−04 | 6.65E−09 | 34 |
|  | mfPDGFRb.mmh | 5.14E+04 | 3.92E−04 | 7.62E−09 | 29 |
|  | hPDGFRb.hFc | 7.13E+04 | 4.50E−05 | 6.32E−10 | 256 |
| H4H3365N | hPDGFRb.mmh | 1.90E+05 | 1.02E−03 | 5.38E−09 | 11 |
|  | mfPDGFRb.mmh | 2.00E+05 | 1.01E−03 | 5.06E−09 | 11 |
|  | hPDGFRb.hFc | 2.50E+05 | 2.64E−04 | 1.05E−09 | 44 |
| H4H3374N | hPDGFRb.mmh | 6.85E+05 | 1.26E−03 | 1.84E−09 | 9 |
|  | mfPDGFRb.mmh | 6.70E+05 | 1.77E−03 | 2.63E−09 | 7 |
|  | hPDGFRb.hFc | 1.63E+06 | 2.91E−04 | 1.78E−10 | 40 |
| H4H3107S | hPDGFRb.mmh | 6.05E+05 | 8.79E−04 | 1.45E−09 | 13 |
|  | mfPDGFRb.mmh | 6.83E+05 | 9.42E−04 | 1.38E−09 | 12 |
|  | hPDGFRb.hFc | 6.95E+05 | 1.15E−04 | 1.65E−10 | 101 |
| H4H3102S | hPDGFRb.mmh | 1.04E+06 | 1.47E−03 | 1.42E−09 | 8 |
|  | mfPDGFRb.mmh | 5.74E+05 | 1.64E−03 | 2.86E−09 | 7 |
|  | hPDGFRb.hFc | 4.20E+05 | 3.19E−04 | 7.60E−10 | 36 |
| H4H3099S | hPDGFRb.mmh | 2.67E+05 | 6.39E−04 | 2.39E−09 | 18 |
|  | mfPDGFRb.mmh | 3.00E+05 | 6.52E−04 | 2.17E−09 | 18 |
|  | hPDGFRb.hFc | 5.40E+05 | 1.05E−04 | 1.93E−10 | 110 |
| H4H3098S | hPDGFRb.mmh | 7.33E+05 | 1.71E−03 | 2.34E−09 | 7 |
|  | mfPDGFRb.mmh | 2.80E+05 | 2.67E−02 | 9.56E−08 | 0.4 |
|  | hPDGFRb.hFc | 3.74E+05 | 7.66E−05 | 2.06E−10 | 151 |
| H4H3104S | hPDGFRb.mmh | 8.33E+05 | 2.80E−03 | 3.37E−09 | 4 |
|  | mfPDGFRb.mmh | 7.40E+05 | 2.99E−03 | 4.05E−09 | 4 |
|  | hPDGFRb.hFc | 9.36E+05 | 5.67E−04 | 6.06E−10 | 20 |
| H4H3094P | hPDGFRb.mmh | 2.23E+05 | 1.47E−03 | 6.58E−09 | 8 |
|  | mfPDGFRb.mmh | 2.53E+05 | 1.70E−03 | 6.69E−09 | 7 |
|  | hPDGFRb.hFc | 2.83E+05 | 2.48E−04 | 8.77E−10 | 47 |
| H4H3103S | hPDGFRb.mmh | 4.92E+05 | 4.97E−03 | 1.01E−08 | 2 |
|  | mfPDGFRb.mmh | 5.44E+05 | 5.56E−03 | 1.02E−08 | 2 |
|  | hPDGFRb.hFc | 7.57E+05 | 3.06E−04 | 4.05E−10 | 38 |
| H4H3106S | hPDGFRb.mmh | 3.94E+05 | 3.35E−03 | 8.49E−09 | 3 |
|  | mfPDGFRb.mmh | 3.72E+05 | 3.45E−03 | 9.26E−09 | 3 |
|  | hPDGFRb.hFc | 3.56E+05 | 7.41E−04 | 2.08E−09 | 16 |

TABLE 5-continued

Binding Characteristics of Anti-PDGFR-beta Antibodies (Human Fc Format) to Monomeric and Dimeric PDGFR-beta constructs at 37° C.

| Antibody | Analyte | ka (M$s^{-1}$) | kd ($s^{-1}$) | $K_D$ (Molar) | $t_{1/2}$ (min) |
|---|---|---|---|---|---|
| H4H3105S | hPDGFRb.mmh | 3.14E+05 | 3.54E−03 | 1.13E−08 | 3 |
|  | mfPDGFRb.mmh | 2.89E+05 | 4.16E−03 | 1.44E−08 | 3 |
|  | hPDGFRb.hFc | 2.80E+05 | 8.24E−04 | 3.00E−09 | 14 |
| H4H3095S | hPDGFRb.mmh | 4.52E+05 | 6.24E−03 | 1.38E−08 | 2 |
|  | mfPDGFRb.mmh | 2.39E+05 | 7.97E−03 | 3.33E−08 | 1.5 |
|  | hPDGFRb.hFc | 4.25E+05 | 7.10E−04 | 1.67E−09 | 16 |
| H4H3096S | hPDGFRb.mmh | 4.52E+05 | 6.24E−03 | 1.38E−08 | 2 |
|  | mfPDGFRb.mmh | 1.62E+05 | 5.12E−03 | 3.16E−08 | 2 |
|  | hPDGFRb.hFc | 2.50E+05 | 7.93E−04 | 3.10E−09 | 15 |
| H4H3097S | hPDGFRb.mmh | NB | NB | NB | NB |
|  | mfPDGFRb.mmh | NB | NB | NB | NB |
|  | hPDGFRb.hFc | NB | NB | NB | NB |
| Control I | hPDGFRb.mmh | 4.50E+05 | 1.46E−02 | 3.25E−08 | 0.8 |
|  | mfPDGFRb.mmh | 4.89E+05 | 9.82E−03 | 2.01E−08 | 1.2 |
|  | hPDGFRb.hFc | 8.04E+05 | 2.17E−04 | 2.70E−10 | 53 |

As shown in Tables 2-5, Several anti-PDGFR-beta antibodies of the present invention displayed sub-nanomolar affinity to the human and M. fascicularis PDGFR-beta constructs. In addition, several clones showed tighter (lower $K_D$) binding to the PDGFR-beta constructs than the reference (Control 1) antibody.

Example 4

Anti-PDGFR-Beta Antibodies Block Binding of PDGF Ligands to PDGFR-Beta

A. Receptor/Ligand Blocking Assessed Using an ELISA-Based Immunoassay

The ability of certain anti-human PDGFR-beta antibodies of the invention to block receptor binding to its ligand PDGF-BB was first evaluated with an ELISA-based immunoassay. Briefly, plates were coated with human PDGF-BB (2 μg/mL). Separately, 250 pM of biotinylated soluble hPDGFR-beta.mmh ("biot-hPDGFR-beta-mmh," SEQ ID NO:337) was premixed with serially diluted anti-PDGFR-beta antibodies (0-100 nM) for 1 hr at room temperature (25° C.). The equilibrated PDGFR-beta/antibody solutions were added to ligand-coated plates, allowed to incubate for 1 hr, and washed. Levels of bound biot-hPDGFR-beta.mmh were detected using HRP conjugated streptavidin. Data were analyzed using Prism software and $IC_{50}$ values were calculated as the amount of antibody required to achieve 50% reduction of hPDGFR-beta-mmh bound to ligand. Maximum blocking values were also calculated and reflect the ability of the antibody to block relative to baseline. The absorbance measured at the constant amount of 250 pM biot-hPDGFR-beta-mmh on the dose curve is defined as 0% blocking and the absorbance with no added PDGFR-beta is defined as 100%. The absorbance of the wells containing the highest antibody concentration determined the maximum blocking percent. Results are shown in Table 6. ("E" indicates that the antibody is an enhancer, i.e., signal was higher in the presence of some concentrations of the antibody than in the absence of the antibody.)

TABLE 6

Anti-PDGFR-beta Antibody Blocking of PDGF-BB Binding to PDGFR-beta

| Antibody | $IC_{50}$ of Antibody Blocking of Ligand/Receptor Interaction (Molar) | % Maximum Blocking |
|---|---|---|
| H1M3299N | 7.6E−09 | 67 |
| H1M3305N | 8.5E−11 | 83 |
| H1M3310N | 1.2E−10 | 88 |
| H1M3361N | 1.0E−10 | 76 |
| H1M3374N | 7.7E−11 | 88 |
| H2M3363N | 4.1E−09 | 77 |
| H2M3365N | 9.0E−11 | 82 |
| H2M3368N | 1.3E−10 | 79 |
| H2M3373N | 9.0E−10 | 80 |
| H4H3094P | 1.2E−10 | 85 |
| H4H3095S | 1.4E−09 | 82 |
| H4H3096S | 1.8E−10 | 84 |
| H4H3097S | E | 5 |
| H4H3098S | E | −13 |
| H4H3099S | 9.7E−11 | 91 |
| H4H3102S | E | 30 |
| H4H3103S | 2.4E−10 | 90 |
| H4H3104S | 3.8E−10 | 89 |
| H4H3105S | 1.6E−10 | 86 |
| H4H3106S | 1.7E−10 | 86 |
| H4H3107S | 6.6E−11 | 83 |
| H4H3305N | 3.0E−10 | 86 |
| H4H3310N | 4.5E−10 | 86 |
| H4H3365N | 3.7E−10 | 87 |
| H4H3374N | 1.2E−10 | 86 |
| Control I | 3.4E−10* | 92 |

*Denotes the average $IC_{50}$ of three separate experiments.

As shown in Table 6, several antibodies of the invention potently block the interaction of PDGFR-beta with its natural ligand PDGF-BB, with $IC_{50}$ values ranging from about 7.6 nM (H1M3299N) to about 66 pM (H4H3107S), and certain antibodies enhanced receptor-ligand interactions (e.g., H4H3097S, H4H3098S and H4H3102S).

B. Receptor/Ligand Blocking Assessed Using a Real-Time Biosensor Assay

The ability of select anti-human PDGFR-beta antibodies to block ligand (PDGF-BB, PDGF-DD and PDGF-AB) binding to human PDGFR-beta was also evaluated using a real-time SPR biosensor assay (Biacore 3000).

Briefly, 400 RUs of soluble human PDGFR-beta.mFc (SEQ ID NO:338) was captured on a Biacore sensor surface derivatized (covalently coupled) with polyclonal rabbit anti-mouse Fc antibody (GE Healthcare Life Sciences, Piscataway, N.J.). The captured surface was saturated with 300 nM of selected anti-PDGFR-beta antibodies for 4 min followed by a 30 nM injection of ligand (PDGF-BB, PDGF-DD or PDGF-AB) for an additional 4 min at 25° C. Real-time binding response was monitored throughout the course of the assay and was compared to the binding response measured when PDGF ligand was applied over the derivatized captured control surface in the absence of captured antibody. Results are illustrated in FIG. 1.

As seen in FIG. 1, all antibodies displayed the ability to block PDGF-BB and PDGF-AB ligands with fewer antibodies enabling efficient blocking of PDGF-DD when compared to the no antibody control. Of note were antibodies H4H3094P, H4H3374N, and Control I, which displayed the least amount of RU response when ligand was applied over the Biacore sensor surface.

Example 5

Cross-Competition Analysis of Anti-PDGFR-Beta Antibodies

A cross-competition assay was conducted to assess the ability of select antibodies to compete with one another for binding to human PDGFR-beta. Briefly, soluble human PDGFR-beta.mmh (SEQ ID NO:337), was captured onto anti-Penta-his Octet sensor tips (ForteBio Corp., Menlo Park, Calif.). Each PDGFR-beta.mmh-coated sensor tip was saturated for 5 min with a first anti-PDGFR-beta antibody (Mab #1; 50 µg/mL). Next, each sensor tip was saturated with a solution of a second anti-PDGFR-beta antibody (Mab #2). The real time response of Mab #2 binding to PDGR-beta.mmh pre-complexed with Mab #1 was then monitored. All assays were performed at 25° C. with a flow rate of 1000 rpm on an Octet RED384 biosensor in Octet HBST buffer according to manufacturer's instructions (ForteBio Corp., Menlo Park, Calif.). Results are illustrated in FIG. 2.

Binding responses of less than 0.1 nM are shown in FIG. 2 in black or gray shading and indicate that the corresponding antibody pairs compete with one another for binding to PDGFR-beta. Binding responses greater than 0.2 nM (shown in white boxes in FIG. 2) denote antibody pairs that do not compete with one another for binding to PDGFR-beta.

The results of this Example indicate that the anti-PDGFR beta antibodies of the invention can be grouped into two distinct "bins" based on epitope binding characteristics: Bin 1 includes Control I, H4H3365N, H4H3374N, H4H3103S and H4H3094P. Bin 2 includes H4H3099S, H4H3107S, H4H3305N and H4H3310N. The results of this Example suggest that the antibodies of Bin 1 bind to distinct regions on PDGFR-beta than the antibodies of Bin 2.

Example 6

Inhibition of Ligand-Mediated Receptor Activation and MAPK Signaling with Anti-PDGFR-Beta Antibodies To further characterize anti-PDGFR-beta antibodies of the present invention, a bioassay was developed to detect the activation of PDGFR-beta by two of its known binding ligands, PDGF BB and DD. The interaction between PDGFR-beta receptors and its ligands is necessary for the induction of diverse cellular processes including proliferation, survival, migration and morphogenesis (Hoch and Soriano, 2003, Development 130:5769-4784). PDGF receptors are receptor tyrosine kinases and are formed by homo- or hetero-dimerization of alpha and beta receptors upon activation by PDGF BB and DD. Upon activation, auto-phosphorylation is induced and several signal transduction pathway cascades are triggered, including the Ras-MAPK (mitogen-activated protein kinase) pathway.

To detect the activation of the MAPK signal transduction pathway via ligand binding to PDGFR beta, a stable HEK293 cell line was generated to express full length human PDGFR-beta along with a luciferase reporter (Serum-Responsive Element [SRE-luciferase]). HEK293/hPDGFR-beta cells were seeded in a 96-well plate and maintained in low-serum media containing 0.1% FBS overnight. Following incubation, PDGF BB or DD, serially diluted 1:3, was added to cells at concentrations ranging from 100 nM to 0.002 nM, to determine dose response. To examine the inhibition of ligand-activated MAPK signaling cascade, antibodies were serially diluted at 1:3 and added to cells at a concentration ranging from 100 nM to 0.002 nM. PDGF BB and DD concentrations remained constant at 250 pM and 400 pM respectively and luciferase activity was detected after 5.5 h. PDGF BB and DD activated human PDGFRb with $EC_{50}$s of 0.04-1.11 nM and 0.34-1.82 nM respectively. The antibody concentration required to inhibit 50% of PDGFR-beta-mediated signaling ($IC_{50}$) was determined for each antibody. Results are summarized in Table 7. (NB=no blocking; Isotype 1=mouse IgG negative control irrelevant antibody; Isotype 2=human IgG negative control irrelevant antibody).

TABLE 7

$IC_{50}$ Values for Anti-PDGFR-beta Antibodies Blocking PDGF-BB and PDGF-DD Ligand Activation

| Antibody | PDGF-BB (250 pM) $IC_{50}$ (M) | PDGF-DD (400 pM) $IC_{50}$ (M) |
|---|---|---|
| H4H3094P | 4.0E−10 | 3.9E−10 |
| H4H3095S | 6.1E−10 | 8.2E−10 |
| H4H3096S | 4.5E−10 | 5.8E−10 |
| H4H3097S | NB | NB |
| H4H3098S | 1.2E−09 | 1.1E−09 |
| H4H3099S | 2.1E−10 | 1.9E−10 |
| H4H3102S | 4.1E−09 | 4.4E−09 |
| H4H3103S | 2.0E−10 | 2.6E−10 |
| H4H3104S | 5.0E−10 | 3.3E−10 |
| H4H3105S | 5.8E−10 | 5.1E−10 |
| H4H3106S | 7.4E−10 | 5.2E−10 |
| H4H3107S | 1.7E−10 | 2.4E−10 |
| H1M3299N | 5.6E−10 | 4.2E−10 |
| H1M3305N | 8.5E−09 | 1.9E−10 |
| H1M3310N | 2.3E−08 | 2.8E−10 |
| H1M3361N | 6.8E−09 | 8.4E−11 |
| H2M3363N | 7.5E−09 | 1.9E−10 |
| H2M3365N | 7.9E−09 | 1.1E−10 |
| H2M3368N | 1.8E−10 | 1.7E−10 |
| H2M3373N | 7.0E−11 | 9.2E−11 |
| H1M3374N | 3.1E−10 | 2.1E−10 |
| H4H3305N | 5.0E−10 | 4.8E−10 |
| H4H3310N | 6.8E−10 | 6.6E−10 |
| H4H3365N | 2.3E−10 | 3.7E−10 |
| H4H3374N | 1.3E−10 | 1.5E−10 |
| Control I | 1.8E−10 | 1.8E−10 |
| Isotype 1 | NB | NB |
| Isotype 2 | NB | NB |

As shown in Table 7, several of the anti-PDGFR-beta antibodies of the present invention potently blocked ligand-dependent PDGFR-beta activation, with $IC_{50}$s in the sub-nanomolar range. Additionally, both mouse IgG (isotype 1) and human IgG (isotype 2) negative controls did not block ligand activation of the receptor.

Example 7

Internalization of Anti-PDGFR-Beta Antibodies on PDGFR-Beta-Expressing Cells To study antibody mediated receptor internalization, experiments were performed using cells engineered to express human PDGFR-beta (HEK293/SRE-luc/PDGFRb cells). Briefly, 20,000 HEK293/SRE Luc/PDGFRb cells/well were plated overnight in full media (10% FBS, Pen/Strep/Glut, NEAA, and G418 in DMEM) and stained with anti-PDGFR-beta antibodies at 10 µg/ml for 30 mins at 4° C. Cells were washed twice and stained with Dylight 488 conjugated Fab goat anti-human IgG secondary antibody (10 µg/mL; Jackson ImmunoResearch Laboratories, West Grove, Pa.) for 30 mins at 4° C. Next, cells were incubated at 37° C. for 2 hours to allow receptor internalization. Alexa-488 fluorescence was quenched by incubating washed cells with anti-Alexa fluor 488 (Invitrogen Corp., Carlsbad, Calif.) for 45 mins at 4° C. to differentiate surface-bound antibodies from the internalized antibodies. Images were taken with ImageXpress Micro XL (Molecular Devices LLC, Sunnyvale, Calif.) and spot analysis was performed using Columbus software (Perkin Elmer, Waltham, Mass.). Relative internalization was calculated by comparing the quenched staining (i.e. internalized antibody) of each antibody to that of the Control 1 antibody. Results are summarized in Table 8.

TABLE 8

Internalization of Select Anti-PDGFR-beta Antibodies

| Antibody | Percent Internalization (Relative to Control I) |
| --- | --- |
| H4H3094P | 77% |
| H4H3099S | 88% |
| H4H3103S | 87% |
| H4H3107S | 92% |
| H4H3305N | 79% |
| H4H3310N | 66% |
| H4H3365N | 65% |
| H4H3374N | 81% |
| Isotype Ctrl | 4% |
| Control I | 100% |

As shown in Table 8, all anti-PDGFR-beta antibodies studied showed robust internalization in this assay format, reflecting the potential ability of the antibodies to effectively target PDGFR-beta-expressing cells in various therapeutic contexts.

Example 8

Anti-PDGFR-Beta Antibodies Bind within Distinct Domains on PDGFR-Beta

The extracellular portion of PDGFR-beta consists of 5 Ig-like C2-type domains, referred to as D1-D5. D1 through D3 are required for high affinity ligand binding. In this Example, experiments were conducted to determine which extracellular domain(s) certain anti-PDGFR-beta antibodies of the invention interact with.

For this experiment, four different PDGFR-beta extracellular domain constructs were used: D1 (SEQ ID NO:342), D1-D2 (SEQ ID NO:343), D1-D3 (SEQ ID NO:344), and D1-D4 (SEQ ID NO:345), as well as full-length PDGFR-beta. Four different anti-PDGFR-beta antibodies were tested for binding to the various constructs by surface plasmon resonance (Biacore). Briefly, 150-200 RU's of anti-PDGFR beta antibody was captured via an anti-human Fc CM5 chip. Next, the individual domain constructs, or full-length PDGFR beta, was applied over the antibody-bound surface at a concentration of 50 nM. The ability of the various antibodies to bind to the various domain constructs was measured. Results are shown in Table 9. (−)=No binding observed; (+)=Binding observed; ND=Not determined.

TABLE 9

Observed Binding of Selected Anti-PDGFR-beta Antibodies to PDGFR-beta Domains and Full-length PDGFR-beta Protein

| | PDGFR-beta Domains | | | | Full-Length | Predicted Domain of |
| --- | --- | --- | --- | --- | --- | --- |
| Antibody | D1 | D1-2 | D1-3 | D1-4 | PDGFR beta | Binding |
| H4H3094P | − | + | + | + | + | 2 |
| H4H3099S | − | − | − | − | + | ND |
| H4H3305N | − | − | − | − | + | ND |
| H4H3374N | − | + | + | + | + | 2 |

As summarized in Table 9, all antibodies bound to full-length PDGFR-beta. Two antibodies, H4H3094P and H4H3374N, were determined to bind to domain 2. Interestingly these two antibodies are also ligand blockers based on the ELISA immunoassay, confirming that domain 2 is important for ligand (PDGF-BB) binding. The two other exemplary antibodies tested, H4H3099S and H4H3305N, did not bind to any of the domain constructs, suggesting that these antibodies may need the amino acids between domains 4 and 5 and/or domain 5 itself for high affinity binding.

Example 9

Anti-PDGFR-Beta Antibodies Deplete Pericytes in an In Vivo Retinal Model

Two exemplary anti-PDGFR beta antibodies, H4H3374N and H4H3094P, were tested in an in vivo retinal pericyte depletion model. Pericytes are smooth-muscle-like cells that express PDGFR-beta. PDGF-B, expressed on endothelial cells, plays a role in the recruitment of pericytes to newly forming vessels, thus promoting angiogenesis and the establishment of vascular architecture. However, the interaction between pericytes and the endothelium, and PDGF-B/PDGFR-beta signaling, is disrupted during pathogenic angiogenesis, contributing to uncontrolled vessel formation. In diseases of the eye, this neovascularization can lead to visual morbidity and blindness.

In a first experiment, humanized PDGFR-beta mouse pups were injected subcutaneously (s.c.) with 3 mg/kg H4H3374N, H4H3094P, control I (2C5) or human Fc (hFc) to see the effect of blocking PDGF-B/PDGFR-beta signaling in newly forming vasculature. Briefly, post-natal day 2 (P2) humanized PDGFR-beta pups were injected subcutaneously with 3 mg/kg of hFc control or PDGFR-beta antibody. On post-natal day 5, pups were sacrificed. Both eyes were collected and fixed in 4% P.F.A for 1 h. Eyes were washed 3× with PBS and retinas were dissected removing hyaloid vessels. Retinas were stained O/N at room temp with a rabbit anti-NG2 chondroitin sulfate primary antibody prepared in antibody dilution serum (ADS; 1% BSA in 0.05% Triton-X-100 in PBS). After incubation, all retinas were washed 3× for 15 min in PBS and then stained O/N at 4° C. with fluorescein labeled *Griffonia Simplicifolia* lectin and a goat anti-rabbit alexa 594 labeled secondary prepared in ADS. After incubation, all retinas were again washed 3× for 15 min in PBS. Retinas were flat-mounted on slides and cover-slipped using Fluoromount-G™ without DAPI.

Retinas were imaged using a Nikon 80i fluorescent microscope. Images were analyzed using Adobe Photoshop and Fovea. The average NG2 positive area, normalized to the hFc, was measured for each treatment group. Both imaging and analysis were performed in a blinded fashion. Statistical analysis was done using one-way ANOVA in prism software. Results are summarized in Tables 10-11.

TABLE 10

Reduction in NG2 Positive Retinal Area Post Treatment with 3 mg/kg H4H3374N, Control I or hFc

| | Normalized NG2 Area Relative to hFc | | |
|---|---|---|---|
| N | hFc | Control I (2C5) | H4H3374N |
| 1 | 1.0 | 1.00 | 0.13 |
| 2 | 1.0 | 0.48 | 0.25 |
| 3 | 1.0 | 0.76 | 0.14 |
| 4 | 1.0 | 0.68 | 0.15 |
| 5 | 1.0 | 0.64 | — |
| Avg | 1.0 | 0.71 | 0.17 |

TABLE 11

Reduction in NG2 Positive Retinal Area Post Treatment with 3 mg/kg H4H3094P, Control I or hFc

| | Normalized NG2 Area Relative to hFc | | |
|---|---|---|---|
| N | hFc | Control I (2C5) | H4H3094P |
| 1 | 1.0 | 0.88 | 0.79 |
| 2 | 1.0 | 0.85 | 0.61 |
| 3 | 1.0 | 0.85 | 0.37 |
| 4 | 1.0 | 0.87 | 0.66 |
| 5 | 1.0 | 0.88 | 0.83 |
| Avg | 1.0 | 0.86 | 0.65 |

As shown in Tables 10-11, the average retinal NG2 positive area was decreased in mice treated with the anti-PDGFR-beta antibodies compared to the hFc. The NG2 positive area was significantly decreased ($p<0.001$) for antibodies H4H3374N and H4H3094P relative to hFc. Furthermore, H4H3374N displayed the greatest reduction in NG2 positive area when compared to both H4H3094P and the Control I antibody.

In a separate set of experiments, C57B1/6 mouse pups were injected subcutaneously (SC) at P2 with an anti-mouse PDGFR-beta antibody "mAb39" (having the variable regions of the antibody referred to as APB5, see Uemura et al., J. Clin. Invest. 2002; 110(11):1619-1628) at doses of 50 mg/kg, 25 mg/kg, 12.5 mg/kg, or 6.25 mg/kg, or with Fc at 50 mg/kg as a control (Study 1). The effect on pericyte coverage was assessed at P5 using a rabbit anti-NG2 chondroitin sulfate proteoglycan 4 primary antibody. In the developing retinal vessels, all doses of mAb39≥12.5 mg/kg inhibited blood vessel pericyte coverage.

In another study (Study 2), P2 pups were injected SC with 25 mg/kg of mAb39 or control. Retinas were collected at P5 and stained with *Griffonia simplicifolia* lectins ("GS Lectin I," Vector Labs). At a 25 mg/kg dose, mAb39 moderately decreased vascularized retinal areas and vessel density compared to controls.

In a separate set of experiments (Study 3), left eyes of pups were injected intravitreally (IVT) with 5 µg (0.5 µl) of mAb39 or control at P4 and collected at P6. A single intravitreal anti-PDGFR-beta antibody administration almost completely depleted mural cells and produced marked effects on retinal vascular differentiation and morphology, e.g., irregular blood vessel caliber. Additional experiments were conducted to investigate the effect of PDGFR-beta neutralization in the eyes of adult mice. In particular, left eyes of adult mice were injected IVT with mAb39 (5 µg or 10 µg) or control (5 µg or 10 µg). Eyes were collected 48 hrs later and stained with anti-NG2 and GS Lectin I. In adult mice, mAb39 produced no evidence of any pericyte loss or any vascular morphological changes.

These studies collectively demonstrate that selective pharmacological neutralization of PDGFR-beta is effective in promoting pericyte depletion and contributes to changes in vascular morphology and growth in developing retinal neovessels. In contrast, this same inhibition does not appear to have any effect on mature pericytes and vessels in the established vasculature in the adult mouse retina.

Example 10

A Phase 1 Clinical Trial of a Combination Formulation Comprising an Anti-PDGFR-Beta Antibody and a VEGF Antagonist in Patients with Age-Related Macular Degeneration Study Overview A phase 1 clinical trial is conducted to test the safety of an anti-PDGFR-beta antibody of the invention delivered by intravitreal injection in patients with neovascular age-related macular degeneration (AMD) in conjunction with intravitreal (IVT) aflibercept. The amino acid sequence of aflibercept (also known as VEGFR1R2-FcΔC1(a)), as well as the nucleic acid sequence encoding the same, are set forth, e.g., in WO2012/097019, the disclosure of which is incorporated by reference herein in its entirety.

The primary objective of this study is to investigate the safety of intravitreal (IVT) anti-PDGFR-beta antibody in patients with neovascular AMD. The secondary objectives are to explore the anatomic effects of IVT anti-PDGFR-beta on corneal neovascularization (CNV) in patients with neovascular AMD, and to determine the pharmacokinetics of anti-PDGFR-beta and aflibercept in humans. Another objective of this study is to determine the presence of antibodies against the anti-PDGFR-beta antibody and/or aflibercept in subjects treated with these agents.

Target Population

The target population for this study is men and women aged 50 years and older with neovascular AMD. Approximately 3-6 patients will be enrolled in four planned cohorts. A total of 15-24 patients is planned. Six patients will be enrolled at the maximum tolerated dose (MTD), if identified, or the highest dose level.

Key Inclusion/Exclusion Criteria

The key inclusion criteria for this study are as follows: (1) men or women 50 years of age or older; and (2) active subfoveal CNV secondary to AMD, including juxtafoveal lesions that affect the fovea as evidenced by FA in the study eye.

The key exclusion criteria are as follows: (1) IVT anti-VEGF therapy in the study eye within 8 weeks of the start of the study (Day 1); (2) any prior treatment with PDGF or PDGFR inhibitors; (3) intraocular pressure greater than or equal to 25 mmHg in the study eye; (4) evidence of infectious blepharitis, keratitis, scleritis, or conjunctivitis in either eye; (5) any intraocular inflammation/infection in either eye within 3 months of the screening visit; (6) current iris neovascularization, vitreous hemorrhage, or tractional retinal detachment visible at the screening assessments in the study eye; (7) evidence of CNV due to any cause other than AMD in either eye; (8) evidence of diabetic retinopathy or diabetic macular edema in either eye; (9) inability to obtain photographs, FA or OCT to document CNV, e.g., due to media opacity, allergy to fluorescein dye or lack of venous access; and (10) systemic (IV) anti-VEGF administration within 6 weeks of Day 1.

Study Design

Patients will be assessed for study eligibility at the screening visit, up to 2 weeks before Day 1/baseline (Visit 2). At the Day 1/baseline (Visit 2), patients will undergo safety assessments prior to receiving the first dose of study drug.

Eligible patients will be enrolled into the current cohort that is open to enrollment. The initial cohort will receive anti-PDGFR-beta/aflibercept (coformulated at 0.2 mg:2 mg). On Day 1 and Day 29 (±3 days), patients will receive an injection of anti-PDGFR-beta/aflibercept.

The dose of anti-PDGFR-beta/aflibercept will be escalated based on safety and tolerability assessed during the previous cohort (starting from the first patient, first dose to 2 weeks following the last patient's second dose in that cohort, or approximately Week 6). Also, the first patient enrolled in each cohort will be observed for at least 1 week after the first dose before additional patients are dosed. Escalation to the next dose cohort will occur once the data have been reviewed. Intra-patient dose escalation will not be permitted.

Patients will be evaluated at study visits for ocular and systemic safety (including ophthalmic exam, laboratory assessments, etc.) and efficacy (OCT, FA/FP, CNV area, classic CNV size, total lesion size, macular volume, imaging, and BCVA using the 4-meter ETDRS protocol) and will be followed to Week 24.

Study Drug Treatments

Four different anti-PDGFR-beta/aflibercept co-formulations will be administered to patients. The co-formulations are summarized in Table 12.

TABLE 12

| Co-Formulation | Anti-PDGFR-beta Antibody | Aflibercept |
|---|---|---|
| 1 | 0.2 mg | 2 mg |
| 2 | 0.5 mg | 2 mg |
| 3 | 1 mg | 2 mg |
| 4 | 3 mg | 2 mg |

Each formulation will consist of 10 mM sodium phosphate, pH 6.2, 0.03% (w/v) polysorbate 20, 5% (w/v) sucrose, and 40 mM sodium chloride.

The various anti-PDGFR-beta/aflibercept co-formulations will be delivered via IVT injection and the injection volume will be 50 µl. As noted above, patients will receive two separate administrations of the co-formulation. The first administration will be on Day 1, and the second administration will be on Day 29.

Primary and Secondary Endpoints

The primary endpoint of the study is safety of study drug. Secondary endpoints are: (1) change in central retinal thickness from baseline (measured by OCT) at Week 8 and Week 12; (2) proportion of patients with complete resolution of retinal fluid (measured by OCT) at Week 8 and Week 12; (3) change in CNV area from baseline (measured by OCT) at Week 8 and Week 12; (4) change in CNV size from baseline (measured by FA) at Week 8 and Week 12; (5) change in area of leakage from baseline (measured by FA) at Week 8 and Week 12; (6) change in BCVA from baseline; and (7) pharmacokinetics and development of anti-drug antibodies.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

What is claimed is:

1. An isolated antibody or antigen-binding fragment thereof that specifically binds human platelet derived growth factor receptor beta (PDGFR-beta), wherein the antibody or antigen-binding fragment thereof comprises three heavy chain complementarity determining regions (HCDR1, HCDR2 and HCDR3) comprising SEQ ID NOs: 132, 134 and 136, respectively; and three light chain complementarity determining regions (LCDR1, LCDR2 and LCDR3) comprising SEQ ID NOs: 140, 142 and 144, respectively.

2. The isolated antibody or antigen-binding fragment of claim 1, wherein the antibody or antigen-binding fragment thereof comprises a heavy chain variable region (HCVR) comprising SEQ ID NO:130, and a light chain variable region (LCVR) comprising SEQ ID NO.138.

3. An isolated antibody or antigen-binding fragment thereof that specifically binds monomeric human platelet derived growth factor receptor beta (PDGFR-beta) with a binding dissociation equilibrium constant ($K_D$) of less than about 200 pM as measured in a surface plasmon resonance assay at 37° C., wherein the antibody or antigen-binding fragment thereof comprises three heavy chain complementarity determining regions (HCDR1, HCDR2 and HCDR3) comprising SEQ ID NOs: 132, 134 and 136, respectively; and three light chain complementarity determining regions (LCDR1, LCDR2 and LCDR3) comprising SEQ ID NOs: 140, 142 and 144, respectively.

4. The isolated antibody or antigen-binding fragment of claim 3, wherein the antibody or antigen-binding fragment thereof comprises a heavy chain variable region (HCVR) comprising SEQ ID NO:130, and a light chain variable region (LCVR) comprising SEQ ID NO.138.

5. A pharmaceutical composition, comprising:
- an antibody or antigen-binding fragment thereof that specifically binds monomeric human platelet derived growth factor receptor beta (PDGFR-beta) with a binding dissociation equilibrium constant ($K_D$) of less than about 200 pM as measured in a surface plasmon resonance assay at 37° C., wherein the antibody or antigen-binding fragment thereof comprises three heavy chain complementarity determining regions (HCDR1, HCDR2 and HCDR3) comprising SEQ ID NOs: 132, 134 and 136, respectively; and three light chain complementarity determining regions (LCDR1, LCDR2 and LCDR3) comprising SEQ ID NOs: 140, 142 and 144, respectively; and
- a VEGF antagonist wherein the VEGF antagonist is selected from the group consisting of aflibercept, bevacizumab, and ranibizumab; and
- a pharmaceutically acceptable carrier or diluent.

6. The pharmaceutical composition of claim 5, wherein the antibody or antigen-binding fragment thereof comprises a heavy chain variable region (HCVR) comprising SEQ ID NO:130, and a light chain variable region (LCVR) comprising SEQ ID NO.138.

* * * * *

SEQUENCE LISTING

```
<160> NUMBER OF SEQ ID NOS: 345

<210> SEQ ID NO 1
<211> LENGTH: 360
<212> TYPE: DNA
<213> ORGANISM: Artificial Sequence
<220> FEATURE:
<223> OTHER INFORMATION: Synthetic

<400> SEQUENCE: 1
caggtgcagc tggtggagtc tgggggaggc gtggtccagc ctgggaggtc cctgagactc      60
tcctgtgcag cctctggatt caccttcagt agctatggct tgcactgggt ccgccaggct     120
ccaggcaagg ggctggagtg ggtggcactt atatcaaatg ttggaagtaa taaatactat     180
gcagactccg tgaagggccg attcaccatc tccagagaca attccaagaa ctcgctgttt     240
ctgcaaatga acagcctgag agctgaggac acggctgtgt attactgtgc gaagggggcc     300
gactactact actacggtat ggacgtctgg ggccaaggga ccacggtcac cgtctcctca     360

<210> SEQ ID NO 2
<211> LENGTH: 120
<212> TYPE: PRT
<213> ORGANISM: Artificial Sequence
<220> FEATURE:
```

```
<223> OTHER INFORMATION: Synthetic

<400> SEQUENCE: 2

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
            20                  25                  30

Gly Leu His Trp Val Arg Gln Ala Pro Gly Lys Gly Leu Glu Trp Val
        35                  40                  45

Ala Leu Ile Ser Asn Val Gly Ser Asn Lys Tyr Tyr Ala Asp Ser Val
    50                  55                  60

Lys Gly Arg Phe Thr Ile Ser Arg Asp Asn Ser Lys Asn Ser Leu Phe
65                  70                  75                  80

Leu Gln Met Asn Ser Leu Arg Ala Glu Asp Thr Ala Val Tyr Tyr Cys
                85                  90                  95

Ala Lys Gly Ala Asp Tyr Tyr Tyr Gly Met Asp Val Trp Gly Gln
            100                 105                 110

Gly Thr Thr Val Thr Val Ser Ser
        115                 120

<210> SEQ ID NO 3
<211> LENGTH: 24
<212> TYPE: DNA
<213> ORGANISM: Artificial Sequence
<220> FEATURE:
<223> OTHER INFORMATION: Synthetic

<400> SEQUENCE: 3
ggattcacct tcagtagcta tggc                                          24

<210> SEQ ID NO 4
<211> LENGTH: 8
<212> TYPE: PRT
<213> ORGANISM: Artificial Sequence
<220> FEATURE:
<223> OTHER INFORMATION: Synthetic

<400> SEQUENCE: 4

Gly Phe Thr Phe Ser Ser Tyr Gly
 1               5

<210> SEQ ID NO 5
<211> LENGTH: 24
<212> TYPE: DNA
<213> ORGANISM: Artificial Sequence
<220> FEATURE:
<223> OTHER INFORMATION: Synthetic

<400> SEQUENCE: 5
atatcaaatg ttggaagtaa taaa                                          24

<210> SEQ ID NO 6
<211> LENGTH: 8
<212> TYPE: PRT
<213> ORGANISM: Artificial Sequence
<220> FEATURE:
<223> OTHER INFORMATION: Synthetic

<400> SEQUENCE: 6

Ile Ser Asn Val Gly Ser Asn Lys
 1               5
```

```
<210> SEQ ID NO 7
<211> LENGTH: 39
<212> TYPE: DNA
<213> ORGANISM: Artificial Sequence
<220> FEATURE:
<223> OTHER INFORMATION: Synthetic

<400> SEQUENCE: 7
gcgaaggggg ccgactacta ctactacggt atggacgtc                                  39

<210> SEQ ID NO 8
<211> LENGTH: 13
<212> TYPE: PRT
<213> ORGANISM: Artificial Sequence
<220> FEATURE:
<223> OTHER INFORMATION: Synthetic

<400> SEQUENCE: 8

Ala Lys Gly Ala Asp Tyr Tyr Tyr Tyr Gly Met Asp Val
 1               5                  10

<210> SEQ ID NO 9
<211> LENGTH: 339
<212> TYPE: DNA
<213> ORGANISM: Artificial Sequence
<220> FEATURE:
<223> OTHER INFORMATION: Synthetic

<400> SEQUENCE: 9
gacatcgtga tgacccagtc tccagactcc ctggctgtgt ctctgggcga gagggccacc           60
atcaactgca gtccagcca gagtgtttta tacagctcca acaataagaa ctacttagct          120
tggtaccagc agaaaccagg acagcctcct aagctgatca tttactggac atccacccgg         180
gaatccgggg tccctgaccg attcagtggc agcgggtctg ggacagattt cactctcacc         240
atcagcagcc tgcaggctga agatgtggca gtttattact gtcagcaata ttatagtact         300
ccattcactt tcggccctgg gaccaaagtg gatatcaaa                                339

<210> SEQ ID NO 10
<211> LENGTH: 113
<212> TYPE: PRT
<213> ORGANISM: Artificial Sequence
<220> FEATURE:
<223> OTHER INFORMATION: Synthetic

<400> SEQUENCE: 10

Asp Ile Val Met Thr Gln Ser Pro Asp Ser Leu Ala Val Ser Leu Gly
 1               5                  10                  15

Glu Arg Ala Thr Ile Asn Cys Lys Ser Ser Gln Ser Val Leu Tyr Ser
                20                  25                  30

Ser Asn Asn Lys Asn Tyr Leu Ala Trp Tyr Gln Gln Lys Pro Gly Gln
            35                  40                  45

Pro Pro Lys Leu Ile Ile Tyr Trp Thr Ser Thr Arg Glu Ser Gly Val
        50                  55                  60

Pro Asp Arg Phe Ser Gly Ser Gly Ser Gly Thr Asp Phe Thr Leu Thr
 65                 70                  75                  80

Ile Ser Ser Leu Gln Ala Glu Asp Val Ala Val Tyr Tyr Cys Gln Gln
                85                  90                  95

Tyr Tyr Ser Thr Pro Phe Thr Phe Gly Pro Gly Thr Lys Val Asp Ile
               100                 105                 110

Lys
```

```
<210> SEQ ID NO 11
<211> LENGTH: 36
<212> TYPE: DNA
<213> ORGANISM: Artificial Sequence
<220> FEATURE:
<223> OTHER INFORMATION: Synthetic

<400> SEQUENCE: 11
cagagtgttt tatacagctc caacaataag aactac                                 36

<210> SEQ ID NO 12
<211> LENGTH: 12
<212> TYPE: PRT
<213> ORGANISM: Artificial Sequence
<220> FEATURE:
<223> OTHER INFORMATION: Synthetic

<400> SEQUENCE: 12

Gln Ser Val Leu Tyr Ser Ser Asn Asn Lys Asn Tyr
 1               5                  10

<210> SEQ ID NO 13
<211> LENGTH: 9
<212> TYPE: DNA
<213> ORGANISM: Artificial Sequence
<220> FEATURE:
<223> OTHER INFORMATION: Synthetic

<400> SEQUENCE: 13 tggacatcc                                                                9

<210> SEQ ID NO 14
<211> LENGTH: 3
<212> TYPE: PRT
<213> ORGANISM: Artificial Sequence
<220> FEATURE:
<223> OTHER INFORMATION: Synthetic

<400> SEQUENCE: 14

Trp Thr Ser
 1

<210> SEQ ID NO 15
<211> LENGTH: 27
<212> TYPE: DNA
<213> ORGANISM: Artificial Sequence
<220> FEATURE:
<223> OTHER INFORMATION: Synthetic

<400> SEQUENCE: 15
cagcaatatt atagtactcc attcact                                           27

<210> SEQ ID NO 16
<211> LENGTH: 9
<212> TYPE: PRT
<213> ORGANISM: Artificial Sequence
<220> FEATURE:
<223> OTHER INFORMATION: Synthetic

<400> SEQUENCE: 16

Gln Gln Tyr Tyr Ser Thr Pro Phe Thr
 1               5

<210> SEQ ID NO 17
<211> LENGTH: 363
<212> TYPE: DNA
```

-continued

<213> ORGANISM: Artificial Sequence
<220> FEATURE:
<223> OTHER INFORMATION: Synthetic

<400> SEQUENCE: 17

```
cagctgcagc tgcaggagtc gggcccagga ctggtgaagc cttcggagac cctgtccctc      60
acctgcattg tctctggtgg ctccatcagc agtagtagtt actactgggg ctggatccgc     120
cagcccccag ggaagggact ggagtggatt gggagtctct attatagtgg gatcaccttc     180
tacaacccgt ccctcaagag tcgagtcacc atatccgtag acacgtccaa gaaccagttc     240
tccctgacgc tgacctctgt gaccgccgca gacacggctg tgttttactg tgcgagacat     300
agggttatgg cttcgagccc ctttgaccac tggggccagg gaaccctggt caccgtctcc     360
tca                                                                    363
```

<210> SEQ ID NO 18
<211> LENGTH: 121
<212> TYPE: PRT
<213> ORGANISM: Artificial Sequence
<220> FEATURE:
<223> OTHER INFORMATION: Synthetic

<400> SEQUENCE: 18

```
Gln Leu Gln Leu Gln Glu Ser Gly Pro Gly Leu Val Lys Pro Ser Glu
 1               5                  10                  15
Thr Leu Ser Leu Thr Cys Ile Val Ser Gly Gly Ser Ile Ser Ser Ser
            20                  25                  30
Ser Tyr Tyr Trp Gly Trp Ile Arg Gln Pro Pro Gly Lys Gly Leu Glu
        35                  40                  45
Trp Ile Gly Ser Leu Tyr Tyr Ser Gly Ile Thr Phe Tyr Asn Pro Ser
    50                  55                  60
Leu Lys Ser Arg Val Thr Ile Ser Val Asp Thr Ser Lys Asn Gln Phe
65                  70                  75                  80
Ser Leu Thr Leu Thr Ser Val Thr Ala Ala Asp Thr Ala Val Phe Tyr
                85                  90                  95
Cys Ala Arg His Arg Val Met Ala Ser Ser Pro Phe Asp His Trp Gly
            100                 105                 110
Gln Gly Thr Leu Val Thr Val Ser Ser
        115                 120
```

<210> SEQ ID NO 19
<211> LENGTH: 30
<212> TYPE: DNA
<213> ORGANISM: Artificial Sequence
<220> FEATURE:
<223> OTHER INFORMATION: Synthetic

<400> SEQUENCE: 19

```
ggtggctcca tcagcagtag tagttactac                                        30
```

<210> SEQ ID NO 20
<211> LENGTH: 10
<212> TYPE: PRT
<213> ORGANISM: Artificial Sequence
<220> FEATURE:
<223> OTHER INFORMATION: Synthetic

<400> SEQUENCE: 20

```
Gly Gly Ser Ile Ser Ser Ser Ser Tyr Tyr
 1               5                  10
```

<210> SEQ ID NO 21
<211> LENGTH: 21
<212> TYPE: DNA
<213> ORGANISM: Artificial Sequence
<220> FEATURE:
<223> OTHER INFORMATION: Synthetic

<400> SEQUENCE: 21
ctctattata gtgggatcac c                                          21

<210> SEQ ID NO 22
<211> LENGTH: 7
<212> TYPE: PRT
<213> ORGANISM: Artificial Sequence
<220> FEATURE:
<223> OTHER INFORMATION: Synthetic

<400> SEQUENCE: 22

Leu Tyr Tyr Ser Gly Ile Thr
1               5

<210> SEQ ID NO 23
<211> LENGTH: 39
<212> TYPE: DNA
<213> ORGANISM: Artificial Sequence
<220> FEATURE:
<223> OTHER INFORMATION: Synthetic

<400> SEQUENCE: 23
gcgagacata gggttatggc ttcgagcccc tttgaccac                        39

<210> SEQ ID NO 24
<211> LENGTH: 13
<212> TYPE: PRT
<213> ORGANISM: Artificial Sequence
<220> FEATURE:
<223> OTHER INFORMATION: Synthetic

<400> SEQUENCE: 24

Ala Arg His Arg Val Met Ala Ser Ser Pro Phe Asp His
1               5                   10

<210> SEQ ID NO 25
<211> LENGTH: 339
<212> TYPE: DNA
<213> ORGANISM: Artificial Sequence
<220> FEATURE:
<223> OTHER INFORMATION: Synthetic

<400> SEQUENCE: 25
gacatcgtga tgacccagtc tccagagtcc ctggctgtgt ctctgggcga gagggccacc    60
atcaactgca agtccagcca gagtatttta tacagctcca acaataagaa ctaccttgct   120
tggtaccagc tgaaaccagg acagcctcct aacctgctca tttattgggc atctacccgg   180
gaatccgggg tccctgaccg attcagtggc agcgggtctg ggacagattt cactctcacc   240
atcggcagcc tgcaggctga agatgtggca gtttattact gtcagcaata ttatagtact   300
ccattcactt tcggccctgg gaccaaagtg gatatcaaa                         339

<210> SEQ ID NO 26
<211> LENGTH: 113
<212> TYPE: PRT
<213> ORGANISM: Artificial Sequence
<220> FEATURE:
<223> OTHER INFORMATION: Synthetic

<400> SEQUENCE: 26

Asp Ile Val Met Thr Gln Ser Pro Glu Ser Leu Ala Val Ser Leu Gly
1               5                  10                  15

Glu Arg Ala Thr Ile Asn Cys Lys Ser Ser Gln Ser Ile Leu Tyr Ser
            20                  25                  30

Ser Asn Asn Lys Asn Tyr Leu Ala Trp Tyr Gln Leu Lys Pro Gly Gln
        35                  40                  45

Pro Pro Asn Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Gly Ser Leu Gln Ala Glu Asp Val Ala Val Tyr Tyr Cys Gln Gln
                85                  90                  95

Tyr Tyr Ser Thr Pro Phe Thr Phe Gly Pro Gly Thr Lys Val Asp Ile
            100                 105                 110

Lys

<210> SEQ ID NO 27
<211> LENGTH: 36
<212> TYPE: DNA
<213> ORGANISM: Artificial Sequence
<220> FEATURE:
<223> OTHER INFORMATION: Synthetic

<400> SEQUENCE: 27
cagagtattt tatacagctc caacaataag aactac                             36

<210> SEQ ID NO 28
<211> LENGTH: 12
<212> TYPE: PRT
<213> ORGANISM: Artificial Sequence
<220> FEATURE:
<223> OTHER INFORMATION: Synthetic

<400> SEQUENCE: 28

Gln Ser Ile Leu Tyr Ser Ser Asn Asn Lys Asn Tyr
1               5                   10

<210> SEQ ID NO 29
<211> LENGTH: 9
<212> TYPE: DNA
<213> ORGANISM: Artificial Sequence
<220> FEATURE:
<223> OTHER INFORMATION: Synthetic

<400> SEQUENCE: 29 tgggcatct                                                            9

<210> SEQ ID NO 30
<211> LENGTH: 3
<212> TYPE: PRT
<213> ORGANISM: Artificial Sequence
<220> FEATURE:
<223> OTHER INFORMATION: Synthetic

<400> SEQUENCE: 30

Trp Ala Ser
1

<210> SEQ ID NO 31
<211> LENGTH: 27

<210> SEQ ID NO 32
<211> LENGTH: 9
<212> TYPE: PRT
<213> ORGANISM: Artificial Sequence
<220> FEATURE:
<223> OTHER INFORMATION: Synthetic

<400> SEQUENCE: 32

Gln Gln Tyr Tyr Ser Thr Pro Phe Thr
 1               5

<210> SEQ ID NO 33
<211> LENGTH: 369
<212> TYPE: DNA
<213> ORGANISM: Artificial Sequence
<220> FEATURE:
<223> OTHER INFORMATION: Synthetic

<400> SEQUENCE: 33

```
gaggtgcaac tgttggagtc tgggggagac ttggtacagc cggggggtc ccttagactc      60
tcctgtgcag cctctggaat cacctttagt agttttgcca tgagctgggt ccgccaggct    120
ccagggaagg ggctggagtg ggtctcaact gttagtgtta gtgctggtat cacatactac    180
gcagactccg tgaagggccg gttcaccatc tccagagaca attccaagaa cacactttat    240
ctgcaaatga acagcctgag agccgaggac acggccatat attattgtgc gaaatcagt    300
tgtactacta acagctgccc cgcttacttt gactactggg gcctgggaac cctggtcacc    360
gtctcctca                                                            369
```

<210> SEQ ID NO 34
<211> LENGTH: 123
<212> TYPE: PRT
<213> ORGANISM: Artificial Sequence
<220> FEATURE:
<223> OTHER INFORMATION: Synthetic

<400> SEQUENCE: 34

Glu Val Gln Leu Leu Glu Ser Gly Gly Asp Leu Val Gln Pro Gly Gly
 1               5                  10                  15

Ser Leu Arg Leu Ser Cys Ala Ala Ser Gly Ile Thr Phe Ser Ser Phe
            20                  25                  30

Ala Met Ser Trp Val Arg Gln Ala Pro Gly Lys Gly Leu Glu Trp Val
        35                  40                  45

Ser Thr Val Ser Val Ser Ala Gly Ile Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Ile Tyr Tyr Cys
                85                  90                  95

Ala Lys Ser Ser Cys Thr Thr Asn Ser Cys Pro Ala Tyr Phe Asp Tyr
            100                 105                 110

Trp Gly Leu Gly Thr Leu Val Thr Val Ser Ser
        115                 120

<210> SEQ ID NO 35
<211> LENGTH: 24
<212> TYPE: DNA
<213> ORGANISM: Artificial Sequence
<220> FEATURE:
<223> OTHER INFORMATION: Synthetic

<400> SEQUENCE: 35
ggaatcacct ttagtagttt tgcc                                    24

<210> SEQ ID NO 36
<211> LENGTH: 8
<212> TYPE: PRT
<213> ORGANISM: Artificial Sequence
<220> FEATURE:
<223> OTHER INFORMATION: Synthetic

<400> SEQUENCE: 36

Gly Ile Thr Phe Ser Ser Phe Ala
 1               5

<210> SEQ ID NO 37
<211> LENGTH: 24
<212> TYPE: DNA
<213> ORGANISM: Artificial Sequence
<220> FEATURE:
<223> OTHER INFORMATION: Synthetic

<400> SEQUENCE: 37
gttagtgtta gtgctggtat caca                                    24

<210> SEQ ID NO 38
<211> LENGTH: 8
<212> TYPE: PRT
<213> ORGANISM: Artificial Sequence
<220> FEATURE:
<223> OTHER INFORMATION: Synthetic

<400> SEQUENCE: 38

Val Ser Val Ser Ala Gly Ile Thr
 1               5

<210> SEQ ID NO 39
<211> LENGTH: 48
<212> TYPE: DNA
<213> ORGANISM: Artificial Sequence
<220> FEATURE:
<223> OTHER INFORMATION: Synthetic

<400> SEQUENCE: 39
gcgaaatcta gttgtactac taacagctgc cccgcttact ttgactac          48

<210> SEQ ID NO 40
<211> LENGTH: 16
<212> TYPE: PRT
<213> ORGANISM: Artificial Sequence
<220> FEATURE:
<223> OTHER INFORMATION: Synthetic

<400> SEQUENCE: 40

Ala Lys Ser Ser Cys Thr Thr Asn Ser Cys Pro Ala Tyr Phe Asp Tyr
 1               5                  10                  15

<210> SEQ ID NO 41
<211> LENGTH: 339

```
<212> TYPE: DNA
<213> ORGANISM: Artificial Sequence
<220> FEATURE:
<223> OTHER INFORMATION: Synthetic

<400> SEQUENCE: 41
gacatcgtga tgacccagtc tccagagtcc ctggctgtgt ctctgggcga gagggccacc    60
atcaactgca agtccagcca gaatatttta tacaggtcca ataataagaa ctacttagct   120
tggtaccagc agaaaccagg acagcctcct aagctgctca tttactgggc atctacccgg   180
gaatccgggg tccctgaccg attcagtggc agcgggtctg ggacagattt cactctcacc   240
atcagcagcc tgcaggctga agatgtggca gtttattact gtcagcaata ttatggcact   300
ccgtacactt ttggccaggg gaccaacctg gagatcaaa                          339

<210> SEQ ID NO 42
<211> LENGTH: 113
<212> TYPE: PRT
<213> ORGANISM: Artificial Sequence
<220> FEATURE:
<223> OTHER INFORMATION: Synthetic

<400> SEQUENCE: 42

Asp Ile Val Met Thr Gln Ser Pro Glu Ser Leu Ala Val Ser Leu Gly
 1               5                  10                  15

Glu Arg Ala Thr Ile Asn Cys Lys Ser Ser Gln Asn Ile Leu Tyr Arg
             20                  25                  30

Ser Asn Asn Lys Asn Tyr Leu Ala Trp Tyr Gln Gln Lys Pro Gly Gln
         35                  40                  45

Pro Pro Lys Leu Leu Ile Tyr Trp Ala Ser Thr Arg Glu Ser Gly Val
     50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                 85                  90                  95

Tyr Tyr Gly Thr Pro Tyr Thr Phe Gly Gln Gly Thr Asn Leu Glu Ile
            100                 105                 110

Lys

<210> SEQ ID NO 43
<211> LENGTH: 36
<212> TYPE: DNA
<213> ORGANISM: Artificial Sequence
<220> FEATURE:
<223> OTHER INFORMATION: Synthetic

<400> SEQUENCE: 43
cagaatattt tatacaggtc aataataag aactac                               36

<210> SEQ ID NO 44
<211> LENGTH: 12
<212> TYPE: PRT
<213> ORGANISM: Artificial Sequence
<220> FEATURE:
<223> OTHER INFORMATION: Synthetic

<400> SEQUENCE: 44

Gln Asn Ile Leu Tyr Arg Ser Asn Asn Lys Asn Tyr
 1               5                  10

<210> SEQ ID NO 45
```

```
<211> LENGTH: 9
<212> TYPE: DNA
<213> ORGANISM: Artificial Sequence
<220> FEATURE:
<223> OTHER INFORMATION: Synthetic

<400> SEQUENCE: 45 tgggcatct                                                                    9

<210> SEQ ID NO 46
<211> LENGTH: 3
<212> TYPE: PRT
<213> ORGANISM: Artificial Sequence
<220> FEATURE:
<223> OTHER INFORMATION: Synthetic

<400> SEQUENCE: 46

Trp Ala Ser
 1

<210> SEQ ID NO 47
<211> LENGTH: 27
<212> TYPE: DNA
<213> ORGANISM: Artificial Sequence
<220> FEATURE:
<223> OTHER INFORMATION: Synthetic

<400> SEQUENCE: 47
cagcaatatt atggcactcc gtacact                                                27

<210> SEQ ID NO 48
<211> LENGTH: 9
<212> TYPE: PRT
<213> ORGANISM: Artificial Sequence
<220> FEATURE:
<223> OTHER INFORMATION: Synthetic

<400> SEQUENCE: 48

Gln Gln Tyr Tyr Gly Thr Pro Tyr Thr
 1               5

<210> SEQ ID NO 49
<211> LENGTH: 378
<212> TYPE: DNA
<213> ORGANISM: Artificial Sequence
<220> FEATURE:
<223> OTHER INFORMATION: Synthetic

<400> SEQUENCE: 49
gaggtgcagc tggtggagtc tgggggaggc ttggtccagc ctgggggtc cctgagactc      60 tcatgtgcag cctctggatt cacctttagt agttattgga tgacctgggt ccgccaggct    120
ccagggaagg ggctggagtg ggtggccaac ataaggcaag atggaagtga caaatactat    180
gtggactctg tgaagggccg attcaccatc tccagagaca cgccaagaa ctcactgttt     240 ctgcaaatga acagcctgag agccgaagac acggctgtgt attactgtgc gaggactaac    300
ggtgggacct acggttataa ccactactac tacggtatgg acgtctgggg ccaagggacc    360
acggtcaccg tctcctca                                                  378

<210> SEQ ID NO 50
<211> LENGTH: 126
<212> TYPE: PRT
<213> ORGANISM: Artificial Sequence
<220> FEATURE:
<223> OTHER INFORMATION: Synthetic
```

<400> SEQUENCE: 50

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Thr Trp Val Arg Gln Ala Pro Gly Lys Gly Leu Glu Trp Val
        35                  40                  45

Ala Asn Ile Arg Gln Asp Gly Ser Asp Lys Tyr Tyr Val Asp Ser Val
    50                  55                  60

Lys Gly Arg Phe Thr Ile Ser Arg Asp Asn Ala Lys Asn Ser Leu Phe
65                  70                  75                  80

Leu Gln Met Asn Ser Leu Arg Ala Glu Asp Thr Ala Val Tyr Tyr Cys
                85                  90                  95

Ala Arg Thr Asn Gly Gly Thr Gly Tyr Asn His Tyr Tyr Tyr Gly
            100                 105                 110

Met Asp Val Trp Gly Gln Gly Thr Thr Val Thr Val Ser Ser
        115                 120                 125

<210> SEQ ID NO 51
<211> LENGTH: 24
<212> TYPE: DNA
<213> ORGANISM: Artificial Sequence
<220> FEATURE:
<223> OTHER INFORMATION: Synthetic

<400> SEQUENCE: 51
ggattcacct ttagtagtta ttgg                                          24

<210> SEQ ID NO 52
<211> LENGTH: 8
<212> TYPE: PRT
<213> ORGANISM: Artificial Sequence
<220> FEATURE:
<223> OTHER INFORMATION: Synthetic

<400> SEQUENCE: 52

Gly Phe Thr Phe Ser Ser Tyr Trp
1               5

<210> SEQ ID NO 53
<211> LENGTH: 24
<212> TYPE: DNA
<213> ORGANISM: Artificial Sequence
<220> FEATURE:
<223> OTHER INFORMATION: Synthetic

<400> SEQUENCE: 53
ataaggcaag atggaagtga caaa                                          24

<210> SEQ ID NO 54
<211> LENGTH: 8
<212> TYPE: PRT
<213> ORGANISM: Artificial Sequence
<220> FEATURE:
<223> OTHER INFORMATION: Synthetic

<400> SEQUENCE: 54

Ile Arg Gln Asp Gly Ser Asp Lys
1               5

<210> SEQ ID NO 55

<211> LENGTH: 57
<212> TYPE: DNA
<213> ORGANISM: Artificial Sequence
<220> FEATURE:
<223> OTHER INFORMATION: Synthetic

<400> SEQUENCE: 55

```
gcgaggacta acggtgggac ctacggttat aaccactact actacggtat ggacgtc      57
```

<210> SEQ ID NO 56
<211> LENGTH: 19
<212> TYPE: PRT
<213> ORGANISM: Artificial Sequence
<220> FEATURE:
<223> OTHER INFORMATION: Synthetic

<400> SEQUENCE: 56

Ala Arg Thr Asn Gly Gly Thr Tyr Gly Tyr Asn His Tyr Tyr Tyr Gly
1               5                   10                  15

Met Asp Val

<210> SEQ ID NO 57
<211> LENGTH: 321
<212> TYPE: DNA
<213> ORGANISM: Artificial Sequence
<220> FEATURE:
<223> OTHER INFORMATION: Synthetic

<400> SEQUENCE: 57

```
gacatccaga tgacccagtc tccatcctcc ctgtctgcat ctgtaggaga cagagtcacc      60
atcacttgcc gggcaagtca gggcattaga aatgatttag gctggtatca gttgaaacca     120
gggaaagccc ctaagcgcct gatctttgct gcatccagtt tgcaaagtgg ggtcccatca     180
aggttcagcg gcagtggatc tgggacagaa ttcactctca caatcagcag cctgcagcct     240
gaagattttg caacttatta ctgtctacaa cataatagtt acccgtggac gttcggccaa     300
gggaccaagg tggaaatcaa a                                                321
```

<210> SEQ ID NO 58
<211> LENGTH: 107
<212> TYPE: PRT
<213> ORGANISM: Artificial Sequence
<220> FEATURE:
<223> OTHER INFORMATION: Synthetic

<400> SEQUENCE: 58

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Leu Lys Pro Gly Lys Ala Pro Lys Arg Leu Ile
        35                  40                  45

Phe Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Trp
                85                  90                  95

Thr Phe Gly Gln Gly Thr Lys Val Glu Ile Lys
            100                 105

-continued

```
<210> SEQ ID NO 59
<211> LENGTH: 18
<212> TYPE: DNA
<213> ORGANISM: Artificial Sequence
<220> FEATURE:
<223> OTHER INFORMATION: Synthetic

<400> SEQUENCE: 59
cagggcatta gaaatgat                                                 18

<210> SEQ ID NO 60
<211> LENGTH: 6
<212> TYPE: PRT
<213> ORGANISM: Artificial Sequence
<220> FEATURE:
<223> OTHER INFORMATION: Synthetic

<400> SEQUENCE: 60

Gln Gly Ile Arg Asn Asp
 1               5

<210> SEQ ID NO 61
<211> LENGTH: 9
<212> TYPE: DNA
<213> ORGANISM: Artificial Sequence
<220> FEATURE:
<223> OTHER INFORMATION: Synthetic

<400> SEQUENCE: 61 gctgcatcc                                                            9

<210> SEQ ID NO 62
<211> LENGTH: 3
<212> TYPE: PRT
<213> ORGANISM: Artificial Sequence
<220> FEATURE:
<223> OTHER INFORMATION: Synthetic

<400> SEQUENCE: 62

Ala Ala Ser
 1

<210> SEQ ID NO 63
<211> LENGTH: 27
<212> TYPE: DNA
<213> ORGANISM: Artificial Sequence
<220> FEATURE:
<223> OTHER INFORMATION: Synthetic

<400> SEQUENCE: 63
ctacaacata atagttaccc gtggacg                                       27

<210> SEQ ID NO 64
<211> LENGTH: 9
<212> TYPE: PRT
<213> ORGANISM: Artificial Sequence
<220> FEATURE:
<223> OTHER INFORMATION: Synthetic

<400> SEQUENCE: 64

Leu Gln His Asn Ser Tyr Pro Trp Thr
 1               5

<210> SEQ ID NO 65
<211> LENGTH: 369
<212> TYPE: DNA
<213> ORGANISM: Artificial Sequence
```

<220> FEATURE:
<223> OTHER INFORMATION: Synthetic

<400> SEQUENCE: 65

```
caggtgcagg tgcaggagtc gggcccagga ctggtgaagc cttcggagac cctgtccctc    60
acctgcactg tctctggtga ctccatcagc agtagtagct actactgggg ctggatccgc   120
cagcccccag ggaaggggct gagtggatt gggagtatct attataatgg gatctcctcc   180
tacaacccgt ccctcaagag tcgagtcacc atatccgtag agtcgtccaa gaaccaattc   240
tccctgaggc tggcctctgt gaccgccgca gacacggctc tatattactg tgcgagacat   300
cgagcagctc gccgttttc tgaggctttt gatatctggg gccaagggac aatggtcacc   360
gtctcttca                                                            369
```

<210> SEQ ID NO 66
<211> LENGTH: 123
<212> TYPE: PRT
<213> ORGANISM: Artificial Sequence
<220> FEATURE:
<223> OTHER INFORMATION: Synthetic

<400> SEQUENCE: 66

```
Gln Val Gln Val Gln Glu Ser Gly Pro Gly Leu Val Lys Pro Ser Glu
 1               5                  10                  15

Thr Leu Ser Leu Thr Cys Thr Val Ser Gly Asp Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Ser Ile Tyr Tyr Asn Gly Ile Ser Ser Tyr Asn Pro Ser
    50                  55                  60

Leu Lys Ser Arg Val Thr Ile Ser Val Glu Ser Ser Lys Asn Gln Phe
65                  70                  75                  80

Ser Leu Arg Leu Ala Ser Val Thr Ala Ala Asp Thr Ala Leu Tyr Tyr
                85                  90                  95

Cys Ala Arg His Arg Ala Ala Arg Arg Phe Ser Glu Ala Phe Asp Ile
            100                 105                 110

Trp Gly Gln Gly Thr Met Val Thr Val Ser Ser
        115                 120
```

<210> SEQ ID NO 67
<211> LENGTH: 30
<212> TYPE: DNA
<213> ORGANISM: Artificial Sequence
<220> FEATURE:
<223> OTHER INFORMATION: Synthetic

<400> SEQUENCE: 67

```
ggtgactcca tcagcagtag tagctactac                                      30
```

<210> SEQ ID NO 68
<211> LENGTH: 10
<212> TYPE: PRT
<213> ORGANISM: Artificial Sequence
<220> FEATURE:
<223> OTHER INFORMATION: Synthetic

<400> SEQUENCE: 68

```
Gly Asp Ser Ile Ser Ser Ser Ser Tyr Tyr
 1               5                  10
```

<210> SEQ ID NO 69
<211> LENGTH: 21
<212> TYPE: DNA
<213> ORGANISM: Artificial Sequence
<220> FEATURE:
<223> OTHER INFORMATION: Synthetic

<400> SEQUENCE: 69
atctattata atgggatctc c                                             21

<210> SEQ ID NO 70
<211> LENGTH: 7
<212> TYPE: PRT
<213> ORGANISM: Artificial Sequence
<220> FEATURE:
<223> OTHER INFORMATION: Synthetic

<400> SEQUENCE: 70

Ile Tyr Tyr Asn Gly Ile Ser
1               5

<210> SEQ ID NO 71
<211> LENGTH: 45
<212> TYPE: DNA
<213> ORGANISM: Artificial Sequence
<220> FEATURE:
<223> OTHER INFORMATION: Synthetic

<400> SEQUENCE: 71
gcgagacatc gagcagctcg ccgttttctc gaggcttttg atatc                   45

<210> SEQ ID NO 72
<211> LENGTH: 15
<212> TYPE: PRT
<213> ORGANISM: Artificial Sequence
<220> FEATURE:
<223> OTHER INFORMATION: Synthetic

<400> SEQUENCE: 72

Ala Arg His Arg Ala Ala Arg Arg Phe Ser Glu Ala Phe Asp Ile
1               5                   10                  15

<210> SEQ ID NO 73
<211> LENGTH: 339
<212> TYPE: DNA
<213> ORGANISM: Artificial Sequence
<220> FEATURE:
<223> OTHER INFORMATION: Synthetic

<400> SEQUENCE: 73
gacatcgtga tgacccagtc tccagactcc ccggctgtgt ctctgggcga gagggccacc    60
atcaactgca gtccagcca gagtgtttta tacagctcca gcaataagaa ctacttagct   120
tggtaccagc agaaaccagg acagcctcct aggttgctca tttactgggc atctacccgg   180
gaatccgggg tccctgaccg attcagtggc agcgggtctg ggacagattt cactctcacc   240
atcagcagcc tgcaggctga agatgtggca gtttattact gtcagcaata ttatagtggt   300
ccgtacactt ttggccaggg gaccaagctg gagatcaaa                         339

<210> SEQ ID NO 74
<211> LENGTH: 113
<212> TYPE: PRT
<213> ORGANISM: Artificial Sequence
<220> FEATURE:
<223> OTHER INFORMATION: Synthetic

<400> SEQUENCE: 74

Asp Ile Val Met Thr Gln Ser Pro Asp Ser Pro Ala Val Ser Leu Gly
1               5                   10                  15

Glu Arg Ala Thr Ile Asn Cys Lys Ser Ser Gln Ser Val Leu Tyr Ser
            20                  25                  30

Ser Ser Asn Lys Asn Tyr Leu Ala Trp Tyr Gln Gln Lys Pro Gly Gln
        35                  40                  45

Pro Pro Arg Leu Leu Ile Tyr Trp Ala Ser Thr Arg Glu Ser Gly Val
50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Gly Pro Tyr Thr Phe Gly Gln Gly Thr Lys Leu Glu Ile
            100                 105                 110

Lys

<210> SEQ ID NO 75
<211> LENGTH: 36
<212> TYPE: DNA
<213> ORGANISM: Artificial Sequence
<220> FEATURE:
<223> OTHER INFORMATION: Synthetic

<400> SEQUENCE: 75
cagagtgttt tatacagctc cagcaataag aactac                                 36

<210> SEQ ID NO 76
<211> LENGTH: 12
<212> TYPE: PRT
<213> ORGANISM: Artificial Sequence
<220> FEATURE:
<223> OTHER INFORMATION: Synthetic

<400> SEQUENCE: 76

Gln Ser Val Leu Tyr Ser Ser Ser Asn Lys Asn Tyr
1               5                   10

<210> SEQ ID NO 77
<211> LENGTH: 9
<212> TYPE: DNA
<213> ORGANISM: Artificial Sequence
<220> FEATURE:
<223> OTHER INFORMATION: Synthetic

<400> SEQUENCE: 77 tgggcatct                                                               9

<210> SEQ ID NO 78
<211> LENGTH: 3
<212> TYPE: PRT
<213> ORGANISM: Artificial Sequence
<220> FEATURE:
<223> OTHER INFORMATION: Synthetic

<400> SEQUENCE: 78

Trp Ala Ser
1

<210> SEQ ID NO 79
<211> LENGTH: 27
<212> TYPE: DNA

<210> SEQ ID NO 79
<211> LENGTH: 27
<212> TYPE: DNA
<213> ORGANISM: Artificial Sequence
<220> FEATURE:
<223> OTHER INFORMATION: Synthetic

<400> SEQUENCE: 79
cagcaatatt atagtggtcc gtacact                                27

<210> SEQ ID NO 80
<211> LENGTH: 9
<212> TYPE: PRT
<213> ORGANISM: Artificial Sequence
<220> FEATURE:
<223> OTHER INFORMATION: Synthetic

<400> SEQUENCE: 80

Gln Gln Tyr Tyr Ser Gly Pro Tyr Thr
 1               5

<210> SEQ ID NO 81
<211> LENGTH: 360
<212> TYPE: DNA
<213> ORGANISM: Artificial Sequence
<220> FEATURE:
<223> OTHER INFORMATION: Synthetic

<400> SEQUENCE: 81
gaagtgcagt tggtggagtc tgggggaggc ttggtacagc ctggcaggtc cctgagactc    60
tcctgtgcag cctctggatt cacctttgat gattttgcca tgcactgggt ccggcaagtt   120
ccagggaagg gcctggagtg ggtctcaggc attagttgga gtagtggaac cataggctat   180
gtgggctctg tgaagggccg cttcaccatc tccagagaca acgccaagaa ctccctgtat   240
ctgcaaatga acagtctgag agctgaggac acggccatgt atttctgtac aaaggataaa   300
gcagctttcc atgatgcctt tgatatctgg ggccaaggga caatggtcac cgtctcttca   360

<210> SEQ ID NO 82
<211> LENGTH: 120
<212> TYPE: PRT
<213> ORGANISM: Artificial Sequence
<220> FEATURE:
<223> OTHER INFORMATION: Synthetic

<400> SEQUENCE: 82

Glu Val Gln Leu Val Glu Ser Gly Gly Gly Leu Val Gln Pro Gly Arg
 1               5                  10                  15

Ser Leu Arg Leu Ser Cys Ala Ala Ser Gly Phe Thr Phe Asp Asp Phe
            20                  25                  30

Ala Met His Trp Val Arg Gln Val Pro Gly Lys Gly Leu Glu Trp Val
        35                  40                  45

Ser Gly Ile Ser Trp Ser Ser Gly Thr Ile Gly Tyr Val Gly Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Met Tyr Phe Cys
                85                  90                  95

Thr Lys Asp Lys Ala Ala Phe His Asp Ala Phe Asp Ile Trp Gly Gln
            100                 105                 110

Gly Thr Met Val Thr Val Ser Ser
        115                 120

<210> SEQ ID NO 83

```
<211> LENGTH: 24
<212> TYPE: DNA
<213> ORGANISM: Artificial Sequence
<220> FEATURE:
<223> OTHER INFORMATION: Synthetic

<400> SEQUENCE: 83
ggattcacct ttgatgattt tgcc                                              24

<210> SEQ ID NO 84
<211> LENGTH: 8
<212> TYPE: PRT
<213> ORGANISM: Artificial Sequence
<220> FEATURE:
<223> OTHER INFORMATION: Synthetic

<400> SEQUENCE: 84

Gly Phe Thr Phe Asp Asp Phe Ala
 1               5

<210> SEQ ID NO 85
<211> LENGTH: 24
<212> TYPE: DNA
<213> ORGANISM: Artificial Sequence
<220> FEATURE:
<223> OTHER INFORMATION: Synthetic

<400> SEQUENCE: 85
attagttgga gtagtggaac cata                                              24

<210> SEQ ID NO 86
<211> LENGTH: 8
<212> TYPE: PRT
<213> ORGANISM: Artificial Sequence
<220> FEATURE:
<223> OTHER INFORMATION: Synthetic

<400> SEQUENCE: 86

Ile Ser Trp Ser Ser Gly Thr Ile
 1               5

<210> SEQ ID NO 87
<211> LENGTH: 39
<212> TYPE: DNA
<213> ORGANISM: Artificial Sequence
<220> FEATURE:
<223> OTHER INFORMATION: Synthetic

<400> SEQUENCE: 87
acaaaggata aagcagcttt ccatgatgcc tttgatatc                              39

<210> SEQ ID NO 88
<211> LENGTH: 13
<212> TYPE: PRT
<213> ORGANISM: Artificial Sequence
<220> FEATURE:
<223> OTHER INFORMATION: Synthetic

<400> SEQUENCE: 88

Thr Lys Asp Lys Ala Ala Phe His Asp Ala Phe Asp Ile
 1               5                  10

<210> SEQ ID NO 89
<211> LENGTH: 339
<212> TYPE: DNA
<213> ORGANISM: Artificial Sequence
<220> FEATURE:
```

<223> OTHER INFORMATION: Synthetic

<400> SEQUENCE: 89

```
gacatcgtga tgacccagtc tccagactcc ctggctgtgt ctctgggcga gagggccacc    60
atcaactgca gtccagcca gagtgtgtta tacaggtccg acaataagaa ctacttagct   120
tggtaccagc agagaccagg acagcctcct aagctgctca tttactgggc atctacccgg   180
gaatccgggg tccctggccg attcagtggc agcgggtctg ggacagattt cactctcacc   240
atcagcagcc tgcagggtga agatgtggca gtttattact gtcatcaata ttataatatt   300
ccattcactt tcggccctgg gaccaaagtg gatatcaaa                          339
```

<210> SEQ ID NO 90
<211> LENGTH: 113
<212> TYPE: PRT
<213> ORGANISM: Artificial Sequence
<220> FEATURE:
<223> OTHER INFORMATION: Synthetic

<400> SEQUENCE: 90

```
Asp Ile Val Met Thr Gln Ser Pro Asp Ser Leu Ala Val Ser Leu Gly
 1               5                  10                  15
Glu Arg Ala Thr Ile Asn Cys Lys Ser Ser Gln Ser Val Leu Tyr Arg
             20                  25                  30
Ser Asp Asn Lys Asn Tyr Leu Ala Trp Tyr Gln Gln Arg Pro Gly Gln
         35                  40                  45
Pro Pro Lys Leu Leu Ile Tyr Trp Ala Ser Thr Arg Glu Ser Gly Val
     50                  55                  60
Pro Gly Arg Phe Ser Gly Ser Gly Ser Gly Thr Asp Phe Thr Leu Thr
 65                  70                  75                  80
Ile Ser Ser Leu Gln Gly Glu Asp Val Ala Val Tyr Tyr Cys His Gln
                 85                  90                  95
Tyr Tyr Asn Ile Pro Phe Thr Phe Gly Pro Gly Thr Lys Val Asp Ile
            100                 105                 110
Lys
```

<210> SEQ ID NO 91
<211> LENGTH: 36
<212> TYPE: DNA
<213> ORGANISM: Artificial Sequence
<220> FEATURE:
<223> OTHER INFORMATION: Synthetic

<400> SEQUENCE: 91

```
cagagtgtgt tatacaggtc cgacaataag aactac                              36
```

<210> SEQ ID NO 92
<211> LENGTH: 12
<212> TYPE: PRT
<213> ORGANISM: Artificial Sequence
<220> FEATURE:
<223> OTHER INFORMATION: Synthetic

<400> SEQUENCE: 92

```
Gln Ser Val Leu Tyr Arg Ser Asp Asn Lys Asn Tyr
 1               5                  10
```

<210> SEQ ID NO 93
<211> LENGTH: 9
<212> TYPE: DNA
<213> ORGANISM: Artificial Sequence
<220> FEATURE:
<223> OTHER INFORMATION: Synthetic

<400> SEQUENCE: 93 tgggcatct                                                                   9

<210> SEQ ID NO 94
<211> LENGTH: 3
<212> TYPE: PRT
<213> ORGANISM: Artificial Sequence
<220> FEATURE:
<223> OTHER INFORMATION: Synthetic

<400> SEQUENCE: 94

Trp Ala Ser
 1

<210> SEQ ID NO 95
<211> LENGTH: 27
<212> TYPE: DNA
<213> ORGANISM: Artificial Sequence
<220> FEATURE:
<223> OTHER INFORMATION: Synthetic

<400> SEQUENCE: 95
catcaatatt ataatattcc attcact                                              27

<210> SEQ ID NO 96
<211> LENGTH: 9
<212> TYPE: PRT
<213> ORGANISM: Artificial Sequence
<220> FEATURE:
<223> OTHER INFORMATION: Synthetic

<400> SEQUENCE: 96

His Gln Tyr Tyr Asn Ile Pro Phe Thr
 1               5

<210> SEQ ID NO 97
<211> LENGTH: 369
<212> TYPE: DNA
<213> ORGANISM: Artificial Sequence
<220> FEATURE:
<223> OTHER INFORMATION: Synthetic

<400> SEQUENCE: 97
caggtgcagc tacagcagtg gggcgcagga ctgttgaagc cttcggagac cctgtccctc          60
acctgcgctg tctatggtgg gtccttcagt ggttactact ggacctggat ccgccagtcc         120
ccagggaagg gctggagtg gatggggaa atcagtcatc gtggaaccac caactacaac          180
ccgtccctca agagtcgact caccatttct cttgacacgt ccaataacca cttctccctg         240
aaattgagct ctgtgaccgc cgcggacacg gctgtttatt attgcgcgag agaggaaagg         300
ttggggatgg gctacgacta cttcggtttg gacgtctggg gccaagggac cacggtcacc         360
gtctcgtca                                                                369

<210> SEQ ID NO 98
<211> LENGTH: 123
<212> TYPE: PRT
<213> ORGANISM: Artificial Sequence
<220> FEATURE:
<223> OTHER INFORMATION: Synthetic

<400> SEQUENCE: 98

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Thr Trp Ile Arg Gln Ser Pro Gly Lys Gly Leu Glu Trp Met
            35                  40                  45

Gly Glu Ile Ser His Arg Gly Thr Thr Asn Tyr Asn Pro Ser Leu Lys
50                  55                  60

Ser Arg Leu Thr Ile Ser Leu Asp Thr Ser Asn Asn His Phe Ser Leu
65                  70                  75                  80

Lys Leu Ser Ser Val Thr Ala Ala Asp Thr Ala Val Tyr Tyr Cys Ala
            85                  90                  95

Arg Glu Glu Arg Leu Gly Met Gly Tyr Asp Tyr Phe Gly Leu Asp Val
            100                 105                 110

Trp Gly Gln Gly Thr Thr Val Thr Val Ser Ser
            115                 120

<210> SEQ ID NO 99
<211> LENGTH: 24
<212> TYPE: DNA
<213> ORGANISM: Artificial Sequence
<220> FEATURE:
<223> OTHER INFORMATION: Synthetic

<400> SEQUENCE: 99
ggtgggtcct tcagtggtta ctac                                      24

<210> SEQ ID NO 100
<211> LENGTH: 8
<212> TYPE: PRT
<213> ORGANISM: Artificial Sequence
<220> FEATURE:
<223> OTHER INFORMATION: Synthetic

<400> SEQUENCE: 100

Gly Gly Ser Phe Ser Gly Tyr Tyr
1               5

<210> SEQ ID NO 101
<211> LENGTH: 21
<212> TYPE: DNA
<213> ORGANISM: Artificial Sequence
<220> FEATURE:
<223> OTHER INFORMATION: Synthetic

<400> SEQUENCE: 101
atcagtcatc gtggaaccac c                                         21

<210> SEQ ID NO 102
<211> LENGTH: 7
<212> TYPE: PRT
<213> ORGANISM: Artificial Sequence
<220> FEATURE:
<223> OTHER INFORMATION: Synthetic

<400> SEQUENCE: 102

Ile Ser His Arg Gly Thr Thr
1               5

<210> SEQ ID NO 103
<211> LENGTH: 51
<212> TYPE: DNA
<213> ORGANISM: Artificial Sequence
<220> FEATURE:
<223> OTHER INFORMATION: Synthetic

<400> SEQUENCE: 103
gcgagagagg aaaggttggg gatgggctac gactacttcg gtttggacgt c         51

<210> SEQ ID NO 104
<211> LENGTH: 17
<212> TYPE: PRT
<213> ORGANISM: Artificial Sequence
<220> FEATURE:
<223> OTHER INFORMATION: Synthetic

<400> SEQUENCE: 104

Ala Arg Glu Glu Arg Leu Gly Met Gly Tyr Asp Tyr Phe Gly Leu Asp
 1               5                  10                  15

Val

<210> SEQ ID NO 105
<211> LENGTH: 318
<212> TYPE: DNA
<213> ORGANISM: Artificial Sequence
<220> FEATURE:
<223> OTHER INFORMATION: Synthetic

<400> SEQUENCE: 105
gaaattgtgt tgacacagtc tccagccacc ctgtctttgt ctccagggga aagagccacc      60
ctctcctgca gggccagtca gagtgtcagc acttacttaa cctggtacca acagaaacct     120
ggccaggctc ccaggctcct catctatgat gcatccaaca gggccactgg catcccagcc     180
aggttcagtg gcagtggatc tgggacagac ttcactctca ccatcagtag cctagagcct     240
gaagattgtg cagtttatta ctgtcagcag cgtagcatct ggatcacctt cggccagggg     300
acacgactgg agattaaa                                                  318

<210> SEQ ID NO 106
<211> LENGTH: 106
<212> TYPE: PRT
<213> ORGANISM: Artificial Sequence
<220> FEATURE:
<223> OTHER INFORMATION: Synthetic

<400> SEQUENCE: 106

Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Ser Val Ser Thr Tyr
            20                  25                  30

Leu Thr Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Cys Ala Val Tyr Tyr Cys Gln Gln Arg Ser Ile Trp Ile Thr
                85                  90                  95

Phe Gly Gln Gly Thr Arg Leu Glu Ile Lys
            100                 105

<210> SEQ ID NO 107
<211> LENGTH: 18
<212> TYPE: DNA

<213> ORGANISM: Artificial Sequence
<220> FEATURE:
<223> OTHER INFORMATION: Synthetic

<400> SEQUENCE: 107
cagagtgtca gcacttac                                                    18

<210> SEQ ID NO 108
<211> LENGTH: 6
<212> TYPE: PRT
<213> ORGANISM: Artificial Sequence
<220> FEATURE:
<223> OTHER INFORMATION: Synthetic

<400> SEQUENCE: 108

Gln Ser Val Ser Thr Tyr
 1               5

<210> SEQ ID NO 109
<211> LENGTH: 9
<212> TYPE: DNA
<213> ORGANISM: Artificial Sequence
<220> FEATURE:
<223> OTHER INFORMATION: Synthetic

<400> SEQUENCE: 109 gatgcatcc                                                               9

<210> SEQ ID NO 110
<211> LENGTH: 3
<212> TYPE: PRT
<213> ORGANISM: Artificial Sequence
<220> FEATURE:
<223> OTHER INFORMATION: Synthetic

<400> SEQUENCE: 110

Asp Ala Ser
 1

<210> SEQ ID NO 111
<211> LENGTH: 24
<212> TYPE: DNA
<213> ORGANISM: Artificial Sequence
<220> FEATURE:
<223> OTHER INFORMATION: Synthetic

<400> SEQUENCE: 111
cagcagcgta gcatctggat cacc                                             24

<210> SEQ ID NO 112
<211> LENGTH: 8
<212> TYPE: PRT
<213> ORGANISM: Artificial Sequence
<220> FEATURE:
<223> OTHER INFORMATION: Synthetic

<400> SEQUENCE: 112

Gln Gln Arg Ser Ile Trp Ile Thr
 1               5

<210> SEQ ID NO 113
<211> LENGTH: 360
<212> TYPE: DNA
<213> ORGANISM: Artificial Sequence
<220> FEATURE:
<223> OTHER INFORMATION: Synthetic

<400> SEQUENCE: 113

```
gaggtacaac tgagagactc tgggggaggc ttggtccagc cggggggtc cctgagactc      60 tcctgtgtag cctctggatt cacctttagt tcctattgga tgagttgggt ccgccaggct    120
ccagggaagg ggctggagtg ggtggtcaat ataaaccgag atggaagtga gaaatactat    180
gtggattctg tgaagggccg attcatcatc tccagagaca acaccaagaa ctcactatat    240
ttacaaatgg agagcctgag agccgaagac acggctgtat attactgtgc gagagatccc    300
ccctaccact tatacggtat ggacgtctgg ggccaaggga ccacggtcac cgtctcctca    360
```

<210> SEQ ID NO 114
<211> LENGTH: 120
<212> TYPE: PRT
<213> ORGANISM: Artificial Sequence
<220> FEATURE:
<223> OTHER INFORMATION: Synthetic

<400> SEQUENCE: 114

```
Glu Val Gln Leu Arg Asp Ser Gly Gly Gly Leu Val Gln Pro Gly Gly
 1               5                  10                  15

Ser Leu Arg Leu Ser Cys Val Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Val Asn Ile Asn Arg Asp Gly Ser Glu Lys Tyr Tyr Val Asp Ser Val
    50                  55                  60

Lys Gly Arg Phe Ile Ile Ser Arg Asp Asn Thr Lys Asn Ser Leu Tyr
65                  70                  75                  80

Leu Gln Met Glu Ser Leu Arg Ala Glu Asp Thr Ala Val Tyr Tyr Cys
                85                  90                  95

Ala Arg Asp Pro Pro Tyr His Leu Tyr Gly Met Asp Val Trp Gly Gln
            100                 105                 110

Gly Thr Thr Val Thr Val Ser Ser
        115                 120
```

<210> SEQ ID NO 115
<211> LENGTH: 24
<212> TYPE: DNA
<213> ORGANISM: Artificial Sequence
<220> FEATURE:
<223> OTHER INFORMATION: Synthetic

<400> SEQUENCE: 115

```
ggattcacct ttagttccta ttgg                                            24
```

<210> SEQ ID NO 116
<211> LENGTH: 8
<212> TYPE: PRT
<213> ORGANISM: Artificial Sequence
<220> FEATURE:
<223> OTHER INFORMATION: Synthetic

<400> SEQUENCE: 116

```
Gly Phe Thr Phe Ser Ser Tyr Trp
 1               5
```

<210> SEQ ID NO 117
<211> LENGTH: 24
<212> TYPE: DNA
<213> ORGANISM: Artificial Sequence
<220> FEATURE:

<223> OTHER INFORMATION: Synthetic

<400> SEQUENCE: 117
ataaaccgag atggaagtga gaaa                                              24

<210> SEQ ID NO 118
<211> LENGTH: 8
<212> TYPE: PRT
<213> ORGANISM: Artificial Sequence
<220> FEATURE:
<223> OTHER INFORMATION: Synthetic

<400> SEQUENCE: 118

Ile Asn Arg Asp Gly Ser Glu Lys
1               5

<210> SEQ ID NO 119
<211> LENGTH: 39
<212> TYPE: DNA
<213> ORGANISM: Artificial Sequence
<220> FEATURE:
<223> OTHER INFORMATION: Synthetic

<400> SEQUENCE: 119
gcgagagatc ccccctacca cttatacggt atggacgtc                              39

<210> SEQ ID NO 120
<211> LENGTH: 13
<212> TYPE: PRT
<213> ORGANISM: Artificial Sequence
<220> FEATURE:
<223> OTHER INFORMATION: Synthetic

<400> SEQUENCE: 120

Ala Arg Asp Pro Pro Tyr His Leu Tyr Gly Met Asp Val
1               5                   10

<210> SEQ ID NO 121
<211> LENGTH: 321
<212> TYPE: DNA
<213> ORGANISM: Artificial Sequence
<220> FEATURE:
<223> OTHER INFORMATION: Synthetic

<400> SEQUENCE: 121
gacatccaga tgacccagtc tccatcctcc ctgtctgcat ctgtaggaga cagagtcacc        60
atcacttgcc ggacaagtca gggcattaga gttgatttag cctggtatca gcagaaacca       120
gggaaagccc ctgagcgcct gatctatgct gcatccagtt tgcaaagtgg ggtcccatca       180
aggttcagcg gcggtggatc tgggacagag ttcactctca cagtcagcag cctgcagcct       240
gaagattttg caacttatta ttgtctacag catcataatt tcccgtacac ttttggccag       300
gggaccaagc tggagatcaa a                                                321

<210> SEQ ID NO 122
<211> LENGTH: 107
<212> TYPE: PRT
<213> ORGANISM: Artificial Sequence
<220> FEATURE:
<223> OTHER INFORMATION: Synthetic

<400> SEQUENCE: 122

Asp Ile Gln Met Thr Gln Ser Pro Ser Ser Leu Ser Ala Ser Val Gly
1               5                   10                  15

```
Asp Arg Val Thr Ile Thr Cys Arg Thr Ser Gln Gly Ile Arg Val Asp
             20                  25                  30

Leu Ala Trp Tyr Gln Gln Lys Pro Gly Lys Ala Pro Glu Arg Leu Ile
         35                  40                  45

Tyr Ala Ala Ser Ser Leu Gln Ser Gly Val Pro Ser Arg Phe Ser Gly
     50                  55                  60

Gly Gly Ser Gly Thr Glu Phe Thr Leu Thr Val Ser Ser Leu Gln Pro
65                  70                  75                  80

Glu Asp Phe Ala Thr Tyr Tyr Cys Leu Gln His His Asn Phe Pro Tyr
             85                  90                  95

Thr Phe Gly Gln Gly Thr Lys Leu Glu Ile Lys
            100                 105
```

<210> SEQ ID NO 123
<211> LENGTH: 18
<212> TYPE: DNA
<213> ORGANISM: Artificial Sequence
<220> FEATURE:
<223> OTHER INFORMATION: Synthetic

<400> SEQUENCE: 123
cagggcatta gagttgat                                            18

<210> SEQ ID NO 124
<211> LENGTH: 6
<212> TYPE: PRT
<213> ORGANISM: Artificial Sequence
<220> FEATURE:
<223> OTHER INFORMATION: Synthetic

<400> SEQUENCE: 124

Gln Gly Ile Arg Val Asp
 1               5

<210> SEQ ID NO 125
<211> LENGTH: 9
<212> TYPE: DNA
<213> ORGANISM: Artificial Sequence
<220> FEATURE:
<223> OTHER INFORMATION: Synthetic

<400> SEQUENCE: 125 gctgcatcc                                                       9

<210> SEQ ID NO 126
<211> LENGTH: 3
<212> TYPE: PRT
<213> ORGANISM: Artificial Sequence
<220> FEATURE:
<223> OTHER INFORMATION: Synthetic

<400> SEQUENCE: 126

Ala Ala Ser
 1

<210> SEQ ID NO 127
<211> LENGTH: 27
<212> TYPE: DNA
<213> ORGANISM: Artificial Sequence
<220> FEATURE:
<223> OTHER INFORMATION: Synthetic

<400> SEQUENCE: 127
ctacagcatc ataatttccc gtacact                                  27

<210> SEQ ID NO 128
<211> LENGTH: 9
<212> TYPE: PRT
<213> ORGANISM: Artificial Sequence
<220> FEATURE:
<223> OTHER INFORMATION: Synthetic

<400> SEQUENCE: 128

Leu Gln His His Asn Phe Pro Tyr Thr
 1               5

<210> SEQ ID NO 129
<211> LENGTH: 366
<212> TYPE: DNA
<213> ORGANISM: Artificial Sequence
<220> FEATURE:
<223> OTHER INFORMATION: Synthetic

<400> SEQUENCE: 129
cagctgcagc tgcaggagtc gggcccagga ctggtgaagc cttcggagac cctgtccctc      60
acctgcactg tctctggtgg ttccatcacc agtagcagtt actactgggg ctggatccgc     120
cagcccccag gaaggggct ggagtggatt gggagtatct attatagagg gagcaccaac      180
tacaatccgt ccctcaagag tcgagtcacc atatccgtag actcgtccaa gaaccagttc     240
tacctgaagg tgtcctctgt gaccgccgta gacacggctg tgtattactg tgcgagacag     300
aatggagcag ctcgtccgag ctggttcgac ccctggggcc agggaaccct ggtcaccgtc     360
tcctca                                                                366

<210> SEQ ID NO 130
<211> LENGTH: 122
<212> TYPE: PRT
<213> ORGANISM: Artificial Sequence
<220> FEATURE:
<223> OTHER INFORMATION: Synthetic

<400> SEQUENCE: 130

Gln Leu Gln Leu Gln Glu Ser Gly Pro Gly Leu Val Lys Pro Ser Glu
 1               5                  10                  15

Thr Leu Ser Leu Thr Cys Thr Val Ser Gly Gly Ser Ile Thr Ser Ser
                20                  25                  30

Ser Tyr Tyr Trp Gly Trp Ile Arg Gln Pro Pro Gly Lys Gly Leu Glu
            35                  40                  45

Trp Ile Gly Ser Ile Tyr Tyr Arg Gly Ser Thr Asn Tyr Asn Pro Ser
     50                  55                  60

Leu Lys Ser Arg Val Thr Ile Ser Val Asp Ser Ser Lys Asn Gln Phe
 65                  70                  75                  80

Tyr Leu Lys Val Ser Ser Val Thr Ala Val Asp Thr Ala Val Tyr Tyr
                85                  90                  95

Cys Ala Arg Gln Asn Gly Ala Ala Arg Pro Ser Trp Phe Asp Pro Trp
            100                 105                 110

Gly Gln Gly Thr Leu Val Thr Val Ser Ser
        115                 120

<210> SEQ ID NO 131
<211> LENGTH: 30
<212> TYPE: DNA
<213> ORGANISM: Artificial Sequence
<220> FEATURE:
<223> OTHER INFORMATION: Synthetic

<400> SEQUENCE: 131
ggtggttcca tcaccagtag cagttactac                                          30

<210> SEQ ID NO 132
<211> LENGTH: 10
<212> TYPE: PRT
<213> ORGANISM: Artificial Sequence
<220> FEATURE:
<223> OTHER INFORMATION: Synthetic

<400> SEQUENCE: 132

Gly Gly Ser Ile Thr Ser Ser Ser Tyr Tyr
 1               5                  10

<210> SEQ ID NO 133
<211> LENGTH: 21
<212> TYPE: DNA
<213> ORGANISM: Artificial Sequence
<220> FEATURE:
<223> OTHER INFORMATION: Synthetic

<400> SEQUENCE: 133
atctattata gagggagcac c                                                   21

<210> SEQ ID NO 134
<211> LENGTH: 7
<212> TYPE: PRT
<213> ORGANISM: Artificial Sequence
<220> FEATURE:
<223> OTHER INFORMATION: Synthetic

<400> SEQUENCE: 134

Ile Tyr Tyr Arg Gly Ser Thr
 1               5

<210> SEQ ID NO 135
<211> LENGTH: 42
<212> TYPE: DNA
<213> ORGANISM: Artificial Sequence
<220> FEATURE:
<223> OTHER INFORMATION: Synthetic

<400> SEQUENCE: 135
gcgagacaga atggagcagc tcgtccgagc tggttcgacc cc                             42

<210> SEQ ID NO 136
<211> LENGTH: 14
<212> TYPE: PRT
<213> ORGANISM: Artificial Sequence
<220> FEATURE:
<223> OTHER INFORMATION: Synthetic

<400> SEQUENCE: 136

Ala Arg Gln Asn Gly Ala Ala Arg Pro Ser Trp Phe Asp Pro
 1               5                  10

<210> SEQ ID NO 137
<211> LENGTH: 324
<212> TYPE: DNA
<213> ORGANISM: Artificial Sequence
<220> FEATURE:
<223> OTHER INFORMATION: Synthetic

<400> SEQUENCE: 137
gaaattgtgt tgacgcagtc tccagacacc atatctttgt ctccagggga aagagccacc         60

```
ctctcctgca gggccagtca gagtattagc agcatctact tagcctggta ccagcagaaa    120
cctggccagg ctcccaggct cctcatctat ggtgcatcca gcagggtcac tggcatccca    180
gacaggttca gtgtcagtgg gtctgggaca gacttcactc tcaccatcag cagactggag    240
cctgaagatt ttgcagtgta ttactgtcag cattatggta tttcaccatt cactttcggc    300
cctgggacca aagtggatat caga                                           324
```

<210> SEQ ID NO 138
<211> LENGTH: 108
<212> TYPE: PRT
<213> ORGANISM: Artificial Sequence
<220> FEATURE:
<223> OTHER INFORMATION: Synthetic

<400> SEQUENCE: 138

```
Glu Ile Val Leu Thr Gln Ser Pro Asp Thr Ile Ser Leu Ser Pro Gly
 1               5                  10                  15

Glu Arg Ala Thr Leu Ser Cys Arg Ala Ser Gln Ser Ile Ser Ser Ile
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Val Thr Gly Ile Pro Asp Arg Phe Ser
    50                  55                  60

Val Ser Gly Ser Gly Thr Asp Phe Thr Leu Thr Ile Ser Arg Leu Glu
65                  70                  75                  80

Pro Glu Asp Phe Ala Val Tyr Tyr Cys Gln His Tyr Gly Ile Ser Pro
                85                  90                  95

Phe Thr Phe Gly Pro Gly Thr Lys Val Asp Ile Arg
            100                 105
```

<210> SEQ ID NO 139
<211> LENGTH: 21
<212> TYPE: DNA
<213> ORGANISM: Artificial Sequence
<220> FEATURE:
<223> OTHER INFORMATION: Synthetic

<400> SEQUENCE: 139

```
cagagtatta gcagcatcta c                                               21
```

<210> SEQ ID NO 140
<211> LENGTH: 7
<212> TYPE: PRT
<213> ORGANISM: Artificial Sequence
<220> FEATURE:
<223> OTHER INFORMATION: Synthetic

<400> SEQUENCE: 140

```
Gln Ser Ile Ser Ser Ile Tyr
 1               5
```

<210> SEQ ID NO 141
<211> LENGTH: 9
<212> TYPE: DNA
<213> ORGANISM: Artificial Sequence
<220> FEATURE:
<223> OTHER INFORMATION: Synthetic

<400> SEQUENCE: 141

```
ggtgcatcc                                                              9
```

<210> SEQ ID NO 142
<211> LENGTH: 3
<212> TYPE: PRT
<213> ORGANISM: Artificial Sequence
<220> FEATURE:
<223> OTHER INFORMATION: Synthetic

<400> SEQUENCE: 142

Gly Ala Ser
 1

<210> SEQ ID NO 143
<211> LENGTH: 27
<212> TYPE: DNA
<213> ORGANISM: Artificial Sequence
<220> FEATURE:
<223> OTHER INFORMATION: Synthetic

<400> SEQUENCE: 143
cagcattatg gtatttcacc attcact                                              27

<210> SEQ ID NO 144
<211> LENGTH: 9
<212> TYPE: PRT
<213> ORGANISM: Artificial Sequence
<220> FEATURE:
<223> OTHER INFORMATION: Synthetic

<400> SEQUENCE: 144

Gln His Tyr Gly Ile Ser Pro Phe Thr
 1               5

<210> SEQ ID NO 145
<211> LENGTH: 381
<212> TYPE: DNA
<213> ORGANISM: Artificial Sequence
<220> FEATURE:
<223> OTHER INFORMATION: Synthetic

<400> SEQUENCE: 145
gaggtgcagc tggtggagtc tgggggaggc ttggtccagc cggggggggtc cctgagactc          60 tcctgtgcag cctctggatt caccttcagt agttattgga tgagttgggt ccgccaggct         120
ccaggcaagg ggctagaatg ggtggccaac atgaaccaag atggaagtga cacacactat         180
gtggactctg tgaagggccg actctccatt tccagagaca atgccaagaa atcactgttt         240
ctgcacatga acagcctgag agccgaggac acggctgttt atttctgtgc gagagatctt         300
gttccacctc gtcaggatga ttactactat tatttcggca tggacgtctg gggccatggg         360
accacggtca ccgtctcctc a                                                   381

<210> SEQ ID NO 146
<211> LENGTH: 127
<212> TYPE: PRT
<213> ORGANISM: Artificial Sequence
<220> FEATURE:
<223> OTHER INFORMATION: Synthetic

<400> SEQUENCE: 146

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val

```
                35                  40                  45
Ala Asn Met Asn Gln Asp Gly Ser Glu Thr His Tyr Val Asp Ser Val
        50                  55                  60

Lys Gly Arg Leu Ser Ile Ser Arg Asp Asn Ala Lys Lys Ser Leu Phe
65                  70                  75                  80

Leu His Met Asn Ser Leu Arg Ala Glu Asp Thr Ala Val Tyr Phe Cys
                85                  90                  95

Ala Arg Asp Leu Val Pro Pro Arg Gln Asp Tyr Tyr Tyr Tyr Phe
            100                 105                 110

Gly Met Asp Val Trp Gly His Gly Thr Thr Val Thr Val Ser Ser
        115                 120                 125
```

<210> SEQ ID NO 147
<211> LENGTH: 24
<212> TYPE: DNA
<213> ORGANISM: Artificial Sequence
<220> FEATURE:
<223> OTHER INFORMATION: Synthetic

<400> SEQUENCE: 147
ggattcacct tcagtagtta ttgg       24

<210> SEQ ID NO 148
<211> LENGTH: 8
<212> TYPE: PRT
<213> ORGANISM: Artificial Sequence
<220> FEATURE:
<223> OTHER INFORMATION: Synthetic

<400> SEQUENCE: 148

```
Gly Phe Thr Phe Ser Ser Tyr Trp
1               5
```

<210> SEQ ID NO 149
<211> LENGTH: 24
<212> TYPE: DNA
<213> ORGANISM: Artificial Sequence
<220> FEATURE:
<223> OTHER INFORMATION: Synthetic

<400> SEQUENCE: 149
atgaaccaag atggaagtga gaca       24

<210> SEQ ID NO 150
<211> LENGTH: 8
<212> TYPE: PRT
<213> ORGANISM: Artificial Sequence
<220> FEATURE:
<223> OTHER INFORMATION: Synthetic

<400> SEQUENCE: 150

```
Met Asn Gln Asp Gly Ser Glu Thr
1               5
```

<210> SEQ ID NO 151
<211> LENGTH: 60
<212> TYPE: DNA
<213> ORGANISM: Artificial Sequence
<220> FEATURE:
<223> OTHER INFORMATION: Synthetic

<400> SEQUENCE: 151
gcgagagatc ttgttccacc tcgtcaggat gattactact attatttcgg catggacgtc       60

<210> SEQ ID NO 152
<211> LENGTH: 20
<212> TYPE: PRT
<213> ORGANISM: Artificial Sequence
<220> FEATURE:
<223> OTHER INFORMATION: Synthetic

<400> SEQUENCE: 152

Ala Arg Asp Leu Val Pro Pro Arg Gln Asp Tyr Tyr Tyr Tyr Phe
1               5                   10                  15

Gly Met Asp Val
            20

<210> SEQ ID NO 153
<211> LENGTH: 321
<212> TYPE: DNA
<213> ORGANISM: Artificial Sequence
<220> FEATURE:
<223> OTHER INFORMATION: Synthetic

<400> SEQUENCE: 153
gacatccaga tgacccagtc tccctccacc ctgtctgcat ctgtaggaga cagagtcacc      60
atcacttgcc gggccagtca gagtattagt gactggttgg cctggtatca gcagaaacca    120
gggaaagccc ctaaactcct gatctttaag gcgtctactt tagaaagtgg ggtcccatca    180
aggttcagcg gcagtggatc tgggacagag ttcactctca ccatcagcag cctacagcct    240
gatgattttg caacttatta ctgccaacag tataatagtt attctcggac gttcggccaa    300
gggaccaagg tggaaatcaa a                                              321

<210> SEQ ID NO 154
<211> LENGTH: 107
<212> TYPE: PRT
<213> ORGANISM: Artificial Sequence
<220> FEATURE:
<223> OTHER INFORMATION: Synthetic

<400> SEQUENCE: 154

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Asp Trp
            20                  25                  30

Leu Ala Trp Tyr Gln Gln Lys Pro Gly Lys Ala Pro Lys Leu Leu Ile
        35                  40                  45

Phe Lys Ala Ser Thr Leu Glu Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Ser Arg
                85                  90                  95

Thr Phe Gly Gln Gly Thr Lys Val Glu Ile Lys
            100                 105

<210> SEQ ID NO 155
<211> LENGTH: 18
<212> TYPE: DNA
<213> ORGANISM: Artificial Sequence
<220> FEATURE:
<223> OTHER INFORMATION: Synthetic

<400> SEQUENCE: 155

```
cagagtatta gtgactgg                                                    18
```

<210> SEQ ID NO 156
<211> LENGTH: 6
<212> TYPE: PRT
<213> ORGANISM: Artificial Sequence
<220> FEATURE:
<223> OTHER INFORMATION: Synthetic

<400> SEQUENCE: 156

Gln Ser Ile Ser Asp Trp
 1               5

<210> SEQ ID NO 157
<211> LENGTH: 9
<212> TYPE: DNA
<213> ORGANISM: Artificial Sequence
<220> FEATURE:
<223> OTHER INFORMATION: Synthetic

<400> SEQUENCE: 157

```
aaggcgtct                                                               9
```

<210> SEQ ID NO 158
<211> LENGTH: 3
<212> TYPE: PRT
<213> ORGANISM: Artificial Sequence
<220> FEATURE:
<223> OTHER INFORMATION: Synthetic

<400> SEQUENCE: 158

Lys Ala Ser
 1

<210> SEQ ID NO 159
<211> LENGTH: 27
<212> TYPE: DNA
<213> ORGANISM: Artificial Sequence
<220> FEATURE:
<223> OTHER INFORMATION: Synthetic

<400> SEQUENCE: 159

```
caacagtata atagttattc tcggacg                                          27
```

<210> SEQ ID NO 160
<211> LENGTH: 9
<212> TYPE: PRT
<213> ORGANISM: Artificial Sequence
<220> FEATURE:
<223> OTHER INFORMATION: Synthetic

<400> SEQUENCE: 160

Gln Gln Tyr Asn Ser Tyr Ser Arg Thr
 1               5

<210> SEQ ID NO 161
<211> LENGTH: 383
<212> TYPE: DNA
<213> ORGANISM: Artificial Sequence
<220> FEATURE:
<223> OTHER INFORMATION: Synthetic

<400> SEQUENCE: 161

```
gaggtgcagc tggtggagtc tgggggaggc ttggtccagc ctggggggtc cctgagactc       60
tcctgtggag cctctggatt caccttagt agttattgga tgacctgggt ccgccaggct      120
```

```
ccagggaagg ggctggagtg ggtgggcaac ataaaccaag atggcagtga gaaatactct    180
gtggactctg tgaagggccg attcaccatc tccagagaca acgccaagaa ctcactgtat    240
ctgcaaatga acagggtgag agccgaggac acggctgtat attattgttc gagagatctt    300
gttccacctc gtcaggggga taactactac tacttcggta tggacgtctg gggcctaggg    360
accacggtca ccgtctcctc agc                                           383
```

<210> SEQ ID NO 162
<211> LENGTH: 127
<212> TYPE: PRT
<213> ORGANISM: Artificial Sequence
<220> FEATURE:
<223> OTHER INFORMATION: Synthetic

<400> SEQUENCE: 162

Glu Val Gln Leu Val Glu Ser Gly Gly Gly Leu Val Gln Pro Gly Gly
1               5                   10                  15

Ser Leu Arg Leu Ser Cys Gly Ala Ser Gly Phe Thr Phe Ser Ser Tyr
            20                  25                  30

Trp Met Thr Trp Val Arg Gln Ala Pro Gly Lys Gly Leu Glu Trp Val
        35                  40                  45

Gly Asn Ile Asn Gln Asp Gly Ser Glu Lys Tyr Ser Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Arg Val Arg Ala Glu Asp Thr Ala Val Tyr Tyr Cys
                85                  90                  95

Ser Arg Asp Leu Val Pro Pro Arg Gln Gly Asp Asn Tyr Tyr Tyr Phe
            100                 105                 110

Gly Met Asp Val Trp Gly Leu Gly Thr Thr Val Thr Val Ser Ser
        115                 120                 125

<210> SEQ ID NO 163
<211> LENGTH: 24
<212> TYPE: DNA
<213> ORGANISM: Artificial Sequence
<220> FEATURE:
<223> OTHER INFORMATION: Synthetic

<400> SEQUENCE: 163
ggattcacct ttagtagtta ttgg                                           24

<210> SEQ ID NO 164
<211> LENGTH: 8
<212> TYPE: PRT
<213> ORGANISM: Artificial Sequence
<220> FEATURE:
<223> OTHER INFORMATION: Synthetic

<400> SEQUENCE: 164

Gly Phe Thr Phe Ser Ser Tyr Trp
1               5

<210> SEQ ID NO 165
<211> LENGTH: 24
<212> TYPE: DNA
<213> ORGANISM: Artificial Sequence
<220> FEATURE:
<223> OTHER INFORMATION: Synthetic

<400> SEQUENCE: 165
ataaaccaag atggcagtga gaaa                                            24

<210> SEQ ID NO 166
<211> LENGTH: 8
<212> TYPE: PRT
<213> ORGANISM: Artificial Sequence
<220> FEATURE:
<223> OTHER INFORMATION: Synthetic

<400> SEQUENCE: 166

Ile Asn Gln Asp Gly Ser Glu Lys
1               5

<210> SEQ ID NO 167
<211> LENGTH: 60
<212> TYPE: DNA
<213> ORGANISM: Artificial Sequence
<220> FEATURE:
<223> OTHER INFORMATION: Synthetic

<400> SEQUENCE: 167
tcgagagatc ttgttccacc tcgtcagggg gataactact actacttcgg tatggacgtc     60

<210> SEQ ID NO 168
<211> LENGTH: 20
<212> TYPE: PRT
<213> ORGANISM: Artificial Sequence
<220> FEATURE:
<223> OTHER INFORMATION: Synthetic

<400> SEQUENCE: 168

Ser Arg Asp Leu Val Pro Pro Arg Gln Gly Asp Asn Tyr Tyr Tyr Phe
1               5                   10                  15

Gly Met Asp Val
            20

<210> SEQ ID NO 169
<211> LENGTH: 321
<212> TYPE: DNA
<213> ORGANISM: Artificial Sequence
<220> FEATURE:
<223> OTHER INFORMATION: Synthetic

<400> SEQUENCE: 169
gacatccaga tgacccagtc tccttccacc ctgtctgcat ctgtaggaga cagagtcatt     60
atcacttgcc gggccagtca gaatattaat aattggttgg cctggtatca gcagcaacca    120
gggaaagccc ctaagctcct gatctatgag gcgtcttctt tagaaagtgg ggtcccatca    180
aggttcagcg gcagtggatc tgggacagaa ttcactctca ccatcggcag cctgcagcct    240
gatgattttg caacttatta ctgccaacac tataattctt attctcggac gttcggccaa    300
gggaccaaag tggatatcaa a                                              321

<210> SEQ ID NO 170
<211> LENGTH: 107
<212> TYPE: PRT
<213> ORGANISM: Artificial Sequence
<220> FEATURE:
<223> OTHER INFORMATION: Synthetic

<400> SEQUENCE: 170

Asp Ile Gln Met Thr Gln Ser Pro Ser Thr Leu Ser Ala Ser Val Gly
1               5                   10                  15

Asp Arg Val Ile Ile Thr Cys Arg Ala Ser Gln Asn Ile Asn Asn Trp

```
                20                  25                  30
Leu Ala Trp Tyr Gln Gln Pro Gly Lys Ala Pro Lys Leu Leu Ile
            35                  40                  45

Tyr Glu Ala Ser Ser Leu Glu Ser Gly Val Pro Ser Arg Phe Ser Gly
 50                  55                  60

Ser Gly Ser Gly Thr Glu Phe Thr Leu Thr Ile Gly Ser Leu Gln Pro
 65                  70                  75                  80

Asp Asp Phe Ala Thr Tyr Tyr Cys Gln His Tyr Asn Ser Tyr Ser Arg
                 85                  90                  95

Thr Phe Gly Gln Gly Thr Lys Val Asp Ile Lys
            100                 105

<210> SEQ ID NO 171
<211> LENGTH: 18
<212> TYPE: DNA
<213> ORGANISM: Artificial Sequence
<220> FEATURE:
<223> OTHER INFORMATION: Synthetic

<400> SEQUENCE: 171
cagaatatta ataattgg                                              18

<210> SEQ ID NO 172
<211> LENGTH: 6
<212> TYPE: PRT
<213> ORGANISM: Artificial Sequence
<220> FEATURE:
<223> OTHER INFORMATION: Synthetic

<400> SEQUENCE: 172

Gln Asn Ile Asn Asn Trp
 1               5

<210> SEQ ID NO 173
<211> LENGTH: 9
<212> TYPE: DNA
<213> ORGANISM: Artificial Sequence
<220> FEATURE:
<223> OTHER INFORMATION: Synthetic

<400> SEQUENCE: 173 gaggcgtct                                                         9

<210> SEQ ID NO 174
<211> LENGTH: 3
<212> TYPE: PRT
<213> ORGANISM: Artificial Sequence
<220> FEATURE:
<223> OTHER INFORMATION: Synthetic

<400> SEQUENCE: 174

Glu Ala Ser
 1

<210> SEQ ID NO 175
<211> LENGTH: 27
<212> TYPE: DNA
<213> ORGANISM: Artificial Sequence
<220> FEATURE:
<223> OTHER INFORMATION: Synthetic

<400> SEQUENCE: 175
caacactata attcttattc tcggacg                                    27
```

<210> SEQ ID NO 176
<211> LENGTH: 9
<212> TYPE: PRT
<213> ORGANISM: Artificial Sequence
<220> FEATURE:
<223> OTHER INFORMATION: Synthetic

<400> SEQUENCE: 176

Gln His Tyr Asn Ser Tyr Ser Arg Thr
1               5

<210> SEQ ID NO 177
<211> LENGTH: 383
<212> TYPE: DNA
<213> ORGANISM: Artificial Sequence
<220> FEATURE:
<223> OTHER INFORMATION: Synthetic

<400> SEQUENCE: 177

```
gaggtgcagc tggtgcagtc tgggggaagt tggtccagc cggggggtc cctgagactc      60 tcctgtacag cctctggatt cacctttagt agctattgga tgagctgggt ccgccaggct    120
ccagggaagg ggctggagtg ggtggccaac atacaacaag atgaaagtga aaatactat    180 gtggactctg tgaagggccg attctccatc tccagagaca acgccaagaa gtcactgtat    240
ctgcaaatga acagcctgag agccgaagac acggctgttt atttctgtgc gagagatctt    300
gtaccacctc gtcagggga ttactaccac tatttcggta tggacgtctg gggccaaggg     360
accctggtca ccgtctcctc agc                                            383
```

<210> SEQ ID NO 178
<211> LENGTH: 127
<212> TYPE: PRT
<213> ORGANISM: Artificial Sequence
<220> FEATURE:
<223> OTHER INFORMATION: Synthetic

<400> SEQUENCE: 178

Glu Val Gln Leu Val Gln Ser Gly Gly Ser Leu Val Gln Pro Gly Gly
1               5                   10                  15

Ser Leu Arg Leu Ser Cys Thr Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Gln Gln Asp Glu Ser Glu Lys Tyr Tyr Val Asp Ser Val
    50                  55                  60

Lys Gly Arg Phe Ser Ile Ser Arg Asp Asn Ala Lys Lys Ser Leu Tyr
65                  70                  75                  80

Leu Gln Met Asn Ser Leu Arg Ala Glu Asp Thr Ala Val Tyr Phe Cys
                85                  90                  95

Ala Arg Asp Leu Val Pro Pro Arg Gln Gly Asp Tyr Tyr His Tyr Phe
            100                 105                 110

Gly Met Asp Val Trp Gly Gln Gly Thr Leu Val Thr Val Ser Ser
        115                 120                 125

<210> SEQ ID NO 179
<211> LENGTH: 24
<212> TYPE: DNA
<213> ORGANISM: Artificial Sequence
<220> FEATURE:
<223> OTHER INFORMATION: Synthetic

<400> SEQUENCE: 179
ggattcacct ttagtagcta ttgg                                              24

<210> SEQ ID NO 180
<211> LENGTH: 8
<212> TYPE: PRT
<213> ORGANISM: Artificial Sequence
<220> FEATURE:
<223> OTHER INFORMATION: Synthetic

<400> SEQUENCE: 180

Gly Phe Thr Phe Ser Ser Tyr Trp
1               5

<210> SEQ ID NO 181
<211> LENGTH: 24
<212> TYPE: DNA
<213> ORGANISM: Artificial Sequence
<220> FEATURE:
<223> OTHER INFORMATION: Synthetic

<400> SEQUENCE: 181
atacaacaag atgaaagtga gaaa                                              24

<210> SEQ ID NO 182
<211> LENGTH: 8
<212> TYPE: PRT
<213> ORGANISM: Artificial Sequence
<220> FEATURE:
<223> OTHER INFORMATION: Synthetic

<400> SEQUENCE: 182

Ile Gln Gln Asp Glu Ser Glu Lys
1               5

<210> SEQ ID NO 183
<211> LENGTH: 60
<212> TYPE: DNA
<213> ORGANISM: Artificial Sequence
<220> FEATURE:
<223> OTHER INFORMATION: Synthetic

<400> SEQUENCE: 183
gcgagagatc ttgtaccacc tcgtcagggg gattactacc actatttcgg tatggacgtc      60

<210> SEQ ID NO 184
<211> LENGTH: 20
<212> TYPE: PRT
<213> ORGANISM: Artificial Sequence
<220> FEATURE:
<223> OTHER INFORMATION: Synthetic

<400> SEQUENCE: 184

Ala Arg Asp Leu Val Pro Pro Arg Gln Gly Asp Tyr Tyr His Tyr Phe
1               5                   10                  15

Gly Met Asp Val
            20

<210> SEQ ID NO 185
<211> LENGTH: 324
<212> TYPE: DNA
<213> ORGANISM: Artificial Sequence
<220> FEATURE:
<223> OTHER INFORMATION: Synthetic

<400> SEQUENCE: 185

```
gccatccgga tgacccagtc tccttccacc ctgtctgcat ctgtaggaga cagagtcacc    60
atcacttgcc gggccagtca gagtattagt gactggttgg cctggtatca gcagaaacca   120
gggaaagccc ctaatctcct gatctataag gcgtctagtt tagaaagtgg ggtcccatca   180
aggttcagcg gcagtggatc tgggacagaa ttcactctca ccatcagcgg cctgcagcct   240
gatgattttg caacttatta ctgccaacag tataatagtt attctcggac gttcggccaa   300
gggaccaagc tggagatcaa acga                                          324
```

```
<210> SEQ ID NO 186
<211> LENGTH: 108
<212> TYPE: PRT
<213> ORGANISM: Artificial Sequence
<220> FEATURE:
<223> OTHER INFORMATION: Synthetic

<400> SEQUENCE: 186

Ala Ile Arg Met Thr Gln Ser Pro Ser Thr Leu Ser Ala Ser Val Gly
 1               5                  10                  15

Asp Arg Val Thr Ile Thr Cys Arg Ala Ser Gln Ser Ile Ser Asp Trp
            20                  25                  30

Leu Ala Trp Tyr Gln Gln Lys Pro Gly Lys Ala Pro Asn Leu Leu Ile
        35                  40                  45

Tyr Lys Ala Ser Ser Leu Glu Ser Gly Val Pro Ser Arg Phe Ser Gly
 50                  55                  60

Ser Gly Ser Gly Thr Glu Phe Thr Leu Thr Ile Ser Gly Leu Gln Pro
 65                  70                  75                  80

Asp Asp Phe Ala Thr Tyr Tyr Cys Gln Gln Tyr Asn Ser Tyr Ser Arg
                85                  90                  95

Thr Phe Gly Gln Gly Thr Lys Leu Glu Ile Lys Arg
            100                 105
```

```
<210> SEQ ID NO 187
<211> LENGTH: 18
<212> TYPE: DNA
<213> ORGANISM: Artificial Sequence
<220> FEATURE:
<223> OTHER INFORMATION: Synthetic

<400> SEQUENCE: 187
cagagtatta gtgactgg                                                  18
```

```
<210> SEQ ID NO 188
<211> LENGTH: 6
<212> TYPE: PRT
<213> ORGANISM: Artificial Sequence
<220> FEATURE:
<223> OTHER INFORMATION: Synthetic

<400> SEQUENCE: 188

Gln Ser Ile Ser Asp Trp
 1               5
```

```
<210> SEQ ID NO 189
<211> LENGTH: 9
<212> TYPE: DNA
<213> ORGANISM: Artificial Sequence
<220> FEATURE:
<223> OTHER INFORMATION: Synthetic

<400> SEQUENCE: 189
```

```
aaggcgtct                                                                    9
```

<210> SEQ ID NO 190
<211> LENGTH: 3
<212> TYPE: PRT
<213> ORGANISM: Artificial Sequence
<220> FEATURE:
<223> OTHER INFORMATION: Synthetic

<400> SEQUENCE: 190

Lys Ala Ser
 1

<210> SEQ ID NO 191
<211> LENGTH: 27
<212> TYPE: DNA
<213> ORGANISM: Artificial Sequence
<220> FEATURE:
<223> OTHER INFORMATION: Synthetic

<400> SEQUENCE: 191

```
caacagtata atagttattc tcggacg                                               27
```

<210> SEQ ID NO 192
<211> LENGTH: 9
<212> TYPE: PRT
<213> ORGANISM: Artificial Sequence
<220> FEATURE:
<223> OTHER INFORMATION: Synthetic

<400> SEQUENCE: 192

Gln Gln Tyr Asn Ser Tyr Ser Arg Thr
 1               5

<210> SEQ ID NO 193
<211> LENGTH: 371
<212> TYPE: DNA
<213> ORGANISM: Artificial Sequence
<220> FEATURE:
<223> OTHER INFORMATION: Synthetic

<400> SEQUENCE: 193

```
caggtgcagt tggtggagtc tggagctgaa atgaagaagc ctggggcctc agtgaaggtc           60
tcctgcaagg cttctggtta ccctttacc gactatggta tcaactgggt gcgacaggcc          120
cctggacaag ggcttgagtg gatgggatgg gtcagcggtt acaatggtaa cacagtcttt         180
gcacagaaga tccagggcag agtcaccatg accacagaca catccacgag cacggcctac         240
atggagctga ggagcctgag atctgacgac acggccgtgt atttctgtgc ccgtatctca         300
gttcggggac actcctacta ccacggtatg ggcgtctggg gccaagggac cacggtcacc         360
gtctcctcag c                                                              371
```

<210> SEQ ID NO 194
<211> LENGTH: 123
<212> TYPE: PRT
<213> ORGANISM: Artificial Sequence
<220> FEATURE:
<223> OTHER INFORMATION: Synthetic

<400> SEQUENCE: 194

Gln Val Gln Leu Val Glu Ser Gly Ala Glu Met Lys Lys Pro Gly Ala
 1               5                  10                  15

Ser Val Lys Val Ser Cys Lys Ala Ser Gly Tyr Thr Phe Thr Asp Tyr
            20                  25                  30

```
Gly Ile Asn Trp Val Arg Gln Ala Pro Gly Gln Gly Leu Glu Trp Met
        35                  40                  45

Gly Trp Val Ser Gly Tyr Asn Gly Asn Thr Val Phe Ala Gln Lys Ile
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Phe Cys
                85                  90                  95

Ala Arg Ile Ser Val Arg Gly His Ser Tyr Tyr His Gly Met Gly Val
            100                 105                 110

Trp Gly Gln Gly Thr Thr Val Thr Val Ser Ser
        115                 120
```

```
<210> SEQ ID NO 195
<211> LENGTH: 24
<212> TYPE: DNA
<213> ORGANISM: Artificial Sequence
<220> FEATURE:
<223> OTHER INFORMATION: Synthetic

<400> SEQUENCE: 195
ggttacacct ttaccgacta tggt                                          24

<210> SEQ ID NO 196
<211> LENGTH: 8
<212> TYPE: PRT
<213> ORGANISM: Artificial Sequence
<220> FEATURE:
<223> OTHER INFORMATION: Synthetic

<400> SEQUENCE: 196

Gly Tyr Thr Phe Thr Asp Tyr Gly
1               5

<210> SEQ ID NO 197
<211> LENGTH: 24
<212> TYPE: DNA
<213> ORGANISM: Artificial Sequence
<220> FEATURE:
<223> OTHER INFORMATION: Synthetic

<400> SEQUENCE: 197
gtcagcggtt acaatggtaa caca                                          24

<210> SEQ ID NO 198
<211> LENGTH: 8
<212> TYPE: PRT
<213> ORGANISM: Artificial Sequence
<220> FEATURE:
<223> OTHER INFORMATION: Synthetic

<400> SEQUENCE: 198

Val Ser Gly Tyr Asn Gly Asn Thr
1               5

<210> SEQ ID NO 199
<211> LENGTH: 48
<212> TYPE: DNA
<213> ORGANISM: Artificial Sequence
<220> FEATURE:
<223> OTHER INFORMATION: Synthetic

<400> SEQUENCE: 199
```

```
gcccgtatct cagttcgggg acactcctac taccacggta tgggcgtc                  48
```

<210> SEQ ID NO 200
<211> LENGTH: 16
<212> TYPE: PRT
<213> ORGANISM: Artificial Sequence
<220> FEATURE:
<223> OTHER INFORMATION: Synthetic

<400> SEQUENCE: 200

```
Ala Arg Ile Ser Val Arg Gly His Ser Tyr Tyr His Gly Met Gly Val
 1               5                  10                  15
```

<210> SEQ ID NO 201
<211> LENGTH: 321
<212> TYPE: DNA
<213> ORGANISM: Artificial Sequence
<220> FEATURE:
<223> OTHER INFORMATION: Synthetic

<400> SEQUENCE: 201

```
gccatccgga tgacccagtc tccatcctca ctgtctgcat ctgtaggaga cagagtcacc      60
atcacttgtc gggcgagtca ggacattaac agttatttag cctggtttca gcagaaacca    120
gggaaagccc ctaagtccct gatctatact gcatccagtt tgcaaagtgg ggtcccatca    180
aagttcagcg gcagtggatc tgggacagat ttcactctca ccatcagcag cctgcagcct    240
gaagattttg caacttatta ctgccaacag tataatactt acccgtacac ttttggccag    300
gggaccaagg tggagagcaa a                                               321
```

<210> SEQ ID NO 202
<211> LENGTH: 107
<212> TYPE: PRT
<213> ORGANISM: Artificial Sequence
<220> FEATURE:
<223> OTHER INFORMATION: Synthetic

<400> SEQUENCE: 202

```
Ala Ile Arg Met Thr Gln Ser Pro Ser Ser Leu Ser Ala Ser Val Gly
 1               5                  10                  15

Asp Arg Val Thr Ile Thr Cys Arg Ala Ser Gln Asp Ile Asn Ser Tyr
            20                  25                  30

Leu Ala Trp Phe Gln Gln Lys Pro Gly Lys Ala Pro Lys Ser Leu Ile
        35                  40                  45

Tyr Thr Ala Ser Ser Leu Gln Ser Gly Val Pro Ser Lys Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Thr Tyr Pro Tyr
                85                  90                  95

Thr Phe Gly Gln Gly Thr Lys Val Glu Ser Lys
            100                 105
```

<210> SEQ ID NO 203
<211> LENGTH: 18
<212> TYPE: DNA
<213> ORGANISM: Artificial Sequence
<220> FEATURE:
<223> OTHER INFORMATION: Synthetic

<400> SEQUENCE: 203

```
caggacatta acagttat                                                    18
```

<210> SEQ ID NO 204
<211> LENGTH: 6
<212> TYPE: PRT
<213> ORGANISM: Artificial Sequence
<220> FEATURE:
<223> OTHER INFORMATION: Synthetic

<400> SEQUENCE: 204

Gln Asp Ile Asn Ser Tyr
 1               5

<210> SEQ ID NO 205
<211> LENGTH: 9
<212> TYPE: DNA
<213> ORGANISM: Artificial Sequence
<220> FEATURE:
<223> OTHER INFORMATION: Synthetic

<400> SEQUENCE: 205 actgcatcc                                                                  9

<210> SEQ ID NO 206
<211> LENGTH: 3
<212> TYPE: PRT
<213> ORGANISM: Artificial Sequence
<220> FEATURE:
<223> OTHER INFORMATION: Synthetic

<400> SEQUENCE: 206

Thr Ala Ser
 1

<210> SEQ ID NO 207
<211> LENGTH: 27
<212> TYPE: DNA
<213> ORGANISM: Artificial Sequence
<220> FEATURE:
<223> OTHER INFORMATION: Synthetic

<400> SEQUENCE: 207
caacagtata atacttaccc gtacact                                             27

<210> SEQ ID NO 208
<211> LENGTH: 9
<212> TYPE: PRT
<213> ORGANISM: Artificial Sequence
<220> FEATURE:
<223> OTHER INFORMATION: Synthetic

<400> SEQUENCE: 208

Gln Gln Tyr Asn Thr Tyr Pro Tyr Thr
 1               5

<210> SEQ ID NO 209
<211> LENGTH: 354
<212> TYPE: DNA
<213> ORGANISM: Artificial Sequence
<220> FEATURE:
<223> OTHER INFORMATION: Synthetic

<400> SEQUENCE: 209
gaagtgcagc tggtggagtc tgggggaggc gtggtccagc ctggagggtc cctgagactc         60
tcctgtgcag cgtctggatt caccttcagt aattatggca tgcactgggt ccgccaggct        120
ccaggcaagg ggctggagtg ggtgacagtt atatggtatg atggaagtta taaatattat        180

```
gcagactccg tgaagggccg attcaccatc tccagagaca attccaagaa tagattgtat      240
ctgcaaatga atagcctgag agccgaggac acggctgtgt attactgtgc gagaggagag      300
ctcggggatg cttttgatat ctggggccaa gggacaatgg tcaccgtctc ttca            354
```

```
<210> SEQ ID NO 210
<211> LENGTH: 118
<212> TYPE: PRT
<213> ORGANISM: Artificial Sequence
<220> FEATURE:
<223> OTHER INFORMATION: Synthetic

<400> SEQUENCE: 210
```

```
Glu Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Asn Tyr
            20                  25                  30

Gly Met His Trp Val Arg Gln Ala Pro Gly Lys Gly Leu Glu Trp Val
        35                  40                  45

Thr Val Ile Trp Tyr Asp Gly Ser Tyr Lys Tyr Tyr Ala Asp Ser Val
    50                  55                  60

Lys Gly Arg Phe Thr Ile Ser Arg Asp Asn Ser Lys Asn Arg Leu Tyr
65                  70                  75                  80

Leu Gln Met Asn Ser Leu Arg Ala Glu Asp Thr Ala Val Tyr Tyr Cys
                85                  90                  95

Ala Arg Gly Glu Leu Gly Asp Ala Phe Asp Ile Trp Gly Gln Gly Thr
            100                 105                 110

Met Val Thr Val Ser Ser
        115
```

```
<210> SEQ ID NO 211
<211> LENGTH: 24
<212> TYPE: DNA
<213> ORGANISM: Artificial Sequence
<220> FEATURE:
<223> OTHER INFORMATION: Synthetic

<400> SEQUENCE: 211
ggattcacct tcagtaatta tggc                                              24
```

```
<210> SEQ ID NO 212
<211> LENGTH: 8
<212> TYPE: PRT
<213> ORGANISM: Artificial Sequence
<220> FEATURE:
<223> OTHER INFORMATION: Synthetic

<400> SEQUENCE: 212

Gly Phe Thr Phe Ser Asn Tyr Gly
 1               5
```

```
<210> SEQ ID NO 213
<211> LENGTH: 24
<212> TYPE: DNA
<213> ORGANISM: Artificial Sequence
<220> FEATURE:
<223> OTHER INFORMATION: Synthetic

<400> SEQUENCE: 213
atatggtatg atggaagtta taaa                                              24
```

```
<210> SEQ ID NO 214
<211> LENGTH: 8
<212> TYPE: PRT
<213> ORGANISM: Artificial Sequence
<220> FEATURE:
<223> OTHER INFORMATION: Synthetic

<400> SEQUENCE: 214

Ile Trp Tyr Asp Gly Ser Tyr Lys
 1               5

<210> SEQ ID NO 215
<211> LENGTH: 33
<212> TYPE: DNA
<213> ORGANISM: Artificial Sequence
<220> FEATURE:
<223> OTHER INFORMATION: Synthetic

<400> SEQUENCE: 215
gcgagaggag agctcgggga tgcttttgat atc                                   33

<210> SEQ ID NO 216
<211> LENGTH: 11
<212> TYPE: PRT
<213> ORGANISM: Artificial Sequence
<220> FEATURE:
<223> OTHER INFORMATION: Synthetic

<400> SEQUENCE: 216

Ala Arg Gly Glu Leu Gly Asp Ala Phe Asp Ile
 1               5                  10

<210> SEQ ID NO 217
<211> LENGTH: 321
<212> TYPE: DNA
<213> ORGANISM: Artificial Sequence
<220> FEATURE:
<223> OTHER INFORMATION: Synthetic

<400> SEQUENCE: 217
gacatccaga tgacccagtc tccttccacc ctgtctgcat ctgtaggaga cagacttacc       60
atcacttgcc gggccagtca gagtattagt acctggttgg cctggtatca gcagaaacca      120
gggaaagccc ctaccctcct gatctataag gcgtctagtt tagagagtgg ggtcccatca      180
aggttcagcg gcagtggatc tgggacagat ttcactctca ccatcagcag cctgcagcct      240
gatgattttg caacttatta ctgccaacag tataagactt cttggacatt cggccaaggg      300
accaagctgg agatcaaacg a                                                321

<210> SEQ ID NO 218
<211> LENGTH: 107
<212> TYPE: PRT
<213> ORGANISM: Artificial Sequence
<220> FEATURE:
<223> OTHER INFORMATION: Synthetic

<400> SEQUENCE: 218

Asp Ile Gln Met Thr Gln Ser Pro Ser Thr Leu Ser Ala Ser Val Gly
 1               5                  10                  15

Asp Arg Leu Thr Ile Thr Cys Arg Ala Ser Gln Ser Ile Ser Thr Trp
            20                  25                  30

Leu Ala Trp Tyr Gln Gln Lys Pro Gly Lys Ala Pro Thr Leu Leu Ile
        35                  40                  45

Tyr Lys Ala Ser Ser Leu Glu Ser Gly Val Pro Ser Arg Phe Ser Gly
```

```
                50                  55                  60
Ser Gly Ser Gly Thr Asp Phe Thr Leu Thr Ile Ser Ser Leu Gln Pro
 65                  70                  75                  80

Asp Asp Phe Ala Thr Tyr Tyr Cys Gln Gln Tyr Lys Thr Ser Trp Thr
                 85                  90                  95

Phe Gly Gln Gly Thr Lys Leu Glu Ile Lys Arg
            100                 105
```

<210> SEQ ID NO 219
<211> LENGTH: 18
<212> TYPE: DNA
<213> ORGANISM: Artificial Sequence
<220> FEATURE:
<223> OTHER INFORMATION: Synthetic

<400> SEQUENCE: 219
cagagtatta gtacctgg                                              18

<210> SEQ ID NO 220
<211> LENGTH: 6
<212> TYPE: PRT
<213> ORGANISM: Artificial Sequence
<220> FEATURE:
<223> OTHER INFORMATION: Synthetic

<400> SEQUENCE: 220

```
Gln Ser Ile Ser Thr Trp
 1               5
```

<210> SEQ ID NO 221
<211> LENGTH: 9
<212> TYPE: DNA
<213> ORGANISM: Artificial Sequence
<220> FEATURE:
<223> OTHER INFORMATION: Synthetic

<400> SEQUENCE: 221 aaggcgtct                                                         9

<210> SEQ ID NO 222
<211> LENGTH: 3
<212> TYPE: PRT
<213> ORGANISM: Artificial Sequence
<220> FEATURE:
<223> OTHER INFORMATION: Synthetic

<400> SEQUENCE: 222

```
Lys Ala Ser
 1
```

<210> SEQ ID NO 223
<211> LENGTH: 24
<212> TYPE: DNA
<213> ORGANISM: Artificial Sequence
<220> FEATURE:
<223> OTHER INFORMATION: Synthetic

<400> SEQUENCE: 223
caacagtata agacttcttg gaca                                       24

<210> SEQ ID NO 224
<211> LENGTH: 8
<212> TYPE: PRT
<213> ORGANISM: Artificial Sequence
<220> FEATURE:

<223> OTHER INFORMATION: Synthetic

<400> SEQUENCE: 224

Gln Gln Tyr Lys Thr Ser Trp Thr
 1               5

<210> SEQ ID NO 225
<211> LENGTH: 372
<212> TYPE: DNA
<213> ORGANISM: Artificial Sequence
<220> FEATURE:
<223> OTHER INFORMATION: Synthetic

<400> SEQUENCE: 225

```
cagatcacct tgaaggagtc tggtcctacg ctggtgaaac ccacacagac cctcacgctg     60
acctgcacct tctctggatt ctcactcact actactgggg tgggtgtggg ctggatccgt    120
cagcccccag gaaaggccct ggaatggctt gcactcattt attggaatga tcttaagcgc    180
tacagcccat ctctgaagaa caggctcacc atcaccaagg acacctccag acaccaggtg    240
gtccttacaa tgaccaacat ggaccctatg gacacagcca catattactg tgcacacaga    300
ccccttact atggttcggg gagtggctgg ttcgacccct ggggcccggg aaccacggtc    360
accgtctcct ca                                                        372
```

<210> SEQ ID NO 226
<211> LENGTH: 124
<212> TYPE: PRT
<213> ORGANISM: Artificial Sequence
<220> FEATURE:
<223> OTHER INFORMATION: Synthetic

<400> SEQUENCE: 226

Gln Ile Thr Leu Lys Glu Ser Gly Pro Thr Leu Val Lys Pro Thr Gln
 1               5                  10                  15
Thr Leu Thr Leu Thr Cys Thr Phe Ser Gly Phe Ser Leu Thr Thr Thr
                20                  25                  30
Gly Val Gly Val Gly Trp Ile Arg Gln Pro Pro Gly Lys Ala Leu Glu
            35                  40                  45
Trp Leu Ala Leu Ile Tyr Trp Asn Asp Leu Lys Arg Tyr Ser Pro Ser
        50                  55                  60
Leu Lys Asn Arg Leu Thr Ile Thr Lys Asp Thr Ser Arg His Gln Val
 65                 70                  75                  80
Val Leu Thr Met Thr Asn Met Asp Pro Met Asp Thr Ala Thr Tyr Tyr
                85                  90                  95
Cys Ala His Arg Pro Leu Tyr Tyr Gly Ser Gly Ser Gly Trp Phe Asp
            100                 105                 110
Pro Trp Gly Pro Gly Thr Thr Val Thr Val Ser Ser
        115                 120

<210> SEQ ID NO 227
<211> LENGTH: 30
<212> TYPE: DNA
<213> ORGANISM: Artificial Sequence
<220> FEATURE:
<223> OTHER INFORMATION: Synthetic

<400> SEQUENCE: 227
ggattctcac tcactactac tggggtgggt     30

<210> SEQ ID NO 228

<210> SEQ ID NO 228
<211> LENGTH: 10
<212> TYPE: PRT
<213> ORGANISM: Artificial Sequence
<220> FEATURE:
<223> OTHER INFORMATION: Synthetic

<400> SEQUENCE: 228

Gly Phe Ser Leu Thr Thr Thr Gly Val Gly
1               5                   10

<210> SEQ ID NO 229
<211> LENGTH: 21
<212> TYPE: DNA
<213> ORGANISM: Artificial Sequence
<220> FEATURE:
<223> OTHER INFORMATION: Synthetic

<400> SEQUENCE: 229
atttattgga atgatcttaa g                                              21

<210> SEQ ID NO 230
<211> LENGTH: 7
<212> TYPE: PRT
<213> ORGANISM: Artificial Sequence
<220> FEATURE:
<223> OTHER INFORMATION: Synthetic

<400> SEQUENCE: 230

Ile Tyr Trp Asn Asp Leu Lys
1               5

<210> SEQ ID NO 231
<211> LENGTH: 48
<212> TYPE: DNA
<213> ORGANISM: Artificial Sequence
<220> FEATURE:
<223> OTHER INFORMATION: Synthetic

<400> SEQUENCE: 231
gcacacagac cctttacta tggttcgggg agtggctggt tcgacccc                  48

<210> SEQ ID NO 232
<211> LENGTH: 16
<212> TYPE: PRT
<213> ORGANISM: Artificial Sequence
<220> FEATURE:
<223> OTHER INFORMATION: Synthetic

<400> SEQUENCE: 232

Ala His Arg Pro Leu Tyr Tyr Gly Ser Gly Ser Gly Trp Phe Asp Pro
1               5                   10                  15

<210> SEQ ID NO 233
<211> LENGTH: 339
<212> TYPE: DNA
<213> ORGANISM: Artificial Sequence
<220> FEATURE:
<223> OTHER INFORMATION: Synthetic

<400> SEQUENCE: 233
gccatccagt tgacccagtc tccagactcc ctggctctgt ctctgggcga gagggccacc    60
atcaactgca agtccagcca gagtgtttta tacagttcca acaataagaa ctacttagct   120
tggtaccagc agaaaccagg acagcctcct aaactactca tttactgggc atcttcccgg   180
gaatccgggg tccctgaccg attcagtggc agcgggtctg ggacagattt cactctcacc   240
atcagcagcc tgcaggctga ggatgtggca gtttattact gtcagcaatt ttatggtact    300
ccgtacactt ttggccaggg gaccaaagtg gatatcaaa    339

<210> SEQ ID NO 234
<211> LENGTH: 113
<212> TYPE: PRT
<213> ORGANISM: Artificial Sequence
<220> FEATURE:
<223> OTHER INFORMATION: Synthetic

<400> SEQUENCE: 234

Ala Ile Gln Leu Thr Gln Ser Pro Asp Ser Leu Ala Leu Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Lys Pro Gly Gln
        35                  40                  45

Pro Pro Lys Leu Leu Ile Tyr Trp Ala Ser Ser Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Phe Tyr Gly Thr Pro Tyr Thr Phe Gly Gln Gly Thr Lys Val Asp Ile
            100                 105                 110

Lys

<210> SEQ ID NO 235
<211> LENGTH: 36
<212> TYPE: DNA
<213> ORGANISM: Artificial Sequence
<220> FEATURE:
<223> OTHER INFORMATION: Synthetic

<400> SEQUENCE: 235
cagagtgttt tatacagttc caacaataag aactac    36

<210> SEQ ID NO 236
<211> LENGTH: 12
<212> TYPE: PRT
<213> ORGANISM: Artificial Sequence
<220> FEATURE:
<223> OTHER INFORMATION: Synthetic

<400> SEQUENCE: 236

Gln Ser Val Leu Tyr Ser Ser Asn Asn Lys Asn Tyr
1               5                   10

<210> SEQ ID NO 237
<211> LENGTH: 9
<212> TYPE: DNA
<213> ORGANISM: Artificial Sequence
<220> FEATURE:
<223> OTHER INFORMATION: Synthetic

<400> SEQUENCE: 237 tgggcatct    9

<210> SEQ ID NO 238
<211> LENGTH: 3
<212> TYPE: PRT
<213> ORGANISM: Artificial Sequence

```
<220> FEATURE:
<223> OTHER INFORMATION: Synthetic

<400> SEQUENCE: 238

Trp Ala Ser
 1

<210> SEQ ID NO 239
<211> LENGTH: 27
<212> TYPE: DNA
<213> ORGANISM: Artificial Sequence
<220> FEATURE:
<223> OTHER INFORMATION: Synthetic

<400> SEQUENCE: 239
cagcaatttt atggtactcc gtacact                                           27

<210> SEQ ID NO 240
<211> LENGTH: 9
<212> TYPE: PRT
<213> ORGANISM: Artificial Sequence
<220> FEATURE:
<223> OTHER INFORMATION: Synthetic

<400> SEQUENCE: 240

Gln Gln Phe Tyr Gly Thr Pro Tyr Thr
 1               5

<210> SEQ ID NO 241
<211> LENGTH: 357
<212> TYPE: DNA
<213> ORGANISM: Artificial Sequence
<220> FEATURE:
<223> OTHER INFORMATION: Synthetic

<400> SEQUENCE: 241
gaggtgcagc tggtggagtc tgggggagac ttggtacatc ctggcaggtc cctgagactc        60
tcctgtgtag cctctggatt cacctttgat gattatacca tgcactgggt ccggcaagct       120
ccagggaagg gcctggagtg gtctcagct attagttgga atggtgataa cataaactat       180
gcgggctctg tgaagggccg attcaccatc tccagagaca cgccaagaa ctccctgtat       240 ctggaaatga acagtctgcg agttgaggac acggccttct attattgtgc aaaagggcgt       300
ggattcagtt ttggctttaa ctacttgggc cagggaacca tggtcaccgt ctcctca        357

<210> SEQ ID NO 242
<211> LENGTH: 119
<212> TYPE: PRT
<213> ORGANISM: Artificial Sequence
<220> FEATURE:
<223> OTHER INFORMATION: Synthetic

<400> SEQUENCE: 242

Glu Val Gln Leu Val Glu Ser Gly Gly Asp Leu Val His Pro Gly Arg
 1               5                  10                  15

Ser Leu Arg Leu Ser Cys Val Ala Ser Gly Phe Thr Phe Asp Asp Tyr
                20                  25                  30

Thr Met His Trp Val Arg Gln Ala Pro Gly Lys Gly Leu Glu Trp Val
            35                  40                  45

Ser Ala Ile Ser Trp Asn Gly Asp Asn Ile Asn Tyr Ala Gly Ser Val
        50                  55                  60

Lys Gly Arg Phe Thr Ile Ser Arg Asp Asn Ala Lys Asn Ser Leu Tyr
 65                  70                  75                  80
```

```
Leu Glu Met Asn Ser Leu Arg Val Glu Asp Thr Ala Phe Tyr Tyr Cys
                 85                  90                  95

Ala Lys Gly Arg Gly Phe Ser Phe Gly Phe Asn Tyr Leu Gly Gln Gly
            100                 105                 110

Thr Met Val Thr Val Ser Ser
        115

<210> SEQ ID NO 243
<211> LENGTH: 24
<212> TYPE: DNA
<213> ORGANISM: Artificial Sequence
<220> FEATURE:
<223> OTHER INFORMATION: Synthetic

<400> SEQUENCE: 243
ggattcacct ttgatgatta tacc                                          24

<210> SEQ ID NO 244
<211> LENGTH: 8
<212> TYPE: PRT
<213> ORGANISM: Artificial Sequence
<220> FEATURE:
<223> OTHER INFORMATION: Synthetic

<400> SEQUENCE: 244

Gly Phe Thr Phe Asp Asp Tyr Thr
1               5

<210> SEQ ID NO 245
<211> LENGTH: 24
<212> TYPE: DNA
<213> ORGANISM: Artificial Sequence
<220> FEATURE:
<223> OTHER INFORMATION: Synthetic

<400> SEQUENCE: 245
attagttgga atggtgataa cata                                          24

<210> SEQ ID NO 246
<211> LENGTH: 8
<212> TYPE: PRT
<213> ORGANISM: Artificial Sequence
<220> FEATURE:
<223> OTHER INFORMATION: Synthetic

<400> SEQUENCE: 246

Ile Ser Trp Asn Gly Asp Asn Ile
1               5

<210> SEQ ID NO 247
<211> LENGTH: 36
<212> TYPE: DNA
<213> ORGANISM: Artificial Sequence
<220> FEATURE:
<223> OTHER INFORMATION: Synthetic

<400> SEQUENCE: 247
gcaaaagggc gtggattcag ttttggcttt aactac                             36

<210> SEQ ID NO 248
<211> LENGTH: 12
<212> TYPE: PRT
<213> ORGANISM: Artificial Sequence
<220> FEATURE:
<223> OTHER INFORMATION: Synthetic
```

<400> SEQUENCE: 248

Ala Lys Gly Arg Gly Phe Ser Phe Gly Phe Asn Tyr
1               5                   10

<210> SEQ ID NO 249
<211> LENGTH: 321
<212> TYPE: DNA
<213> ORGANISM: Artificial Sequence
<220> FEATURE:
<223> OTHER INFORMATION: Synthetic

<400> SEQUENCE: 249
gccatccgga tgacccagtc tccatcctca ctgtctgcat ctgtgggaga cagagttacc    60
atcacttgtc gggcgagtca ggacattagc aattatttag cctggtttca gcagcaacca   120
ggaaaagccc ctaagtccct gatctatgct acatccagtt tgaacagtgg ggtcccatca   180
aagttcagcg gcagtggatc tgggacagac ttcactctca ccatcagcag cctgcagcct   240
gaagattttg caacttatta ctgccaacaa tataagtcct accctctcac tttcggcgga   300
gggaccaagg tggaaatcaa a                                             321

<210> SEQ ID NO 250
<211> LENGTH: 107
<212> TYPE: PRT
<213> ORGANISM: Artificial Sequence
<220> FEATURE:
<223> OTHER INFORMATION: Synthetic

<400> SEQUENCE: 250

Ala Ile Arg Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Ala Trp Phe Gln Gln Gln Pro Gly Lys Ala Pro Lys Ser Leu Ile
        35                  40                  45

Tyr Ala Thr Ser Ser Leu Asn Ser Gly Val Pro Ser Lys Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Lys Ser Tyr Pro Leu
                85                  90                  95

Thr Phe Gly Gly Gly Thr Lys Val Glu Ile Lys
            100                 105

<210> SEQ ID NO 251
<211> LENGTH: 18
<212> TYPE: DNA
<213> ORGANISM: Artificial Sequence
<220> FEATURE:
<223> OTHER INFORMATION: Synthetic

<400> SEQUENCE: 251
caggacatta gcaattat                                                  18

<210> SEQ ID NO 252
<211> LENGTH: 6
<212> TYPE: PRT
<213> ORGANISM: Artificial Sequence
<220> FEATURE:
<223> OTHER INFORMATION: Synthetic

<400> SEQUENCE: 252

Gln Asp Ile Ser Asn Tyr
 1               5

<210> SEQ ID NO 253
<211> LENGTH: 9
<212> TYPE: DNA
<213> ORGANISM: Artificial Sequence
<220> FEATURE:
<223> OTHER INFORMATION: Synthetic

<400> SEQUENCE: 253 gctacatcc                                                                9

<210> SEQ ID NO 254
<211> LENGTH: 3
<212> TYPE: PRT
<213> ORGANISM: Artificial Sequence
<220> FEATURE:
<223> OTHER INFORMATION: Synthetic

<400> SEQUENCE: 254

Ala Thr Ser
 1

<210> SEQ ID NO 255
<211> LENGTH: 27
<212> TYPE: DNA
<213> ORGANISM: Artificial Sequence
<220> FEATURE:
<223> OTHER INFORMATION: Synthetic

<400> SEQUENCE: 255
caacaatata agtcctaccc tctcact                                            27

<210> SEQ ID NO 256
<211> LENGTH: 9
<212> TYPE: PRT
<213> ORGANISM: Artificial Sequence
<220> FEATURE:
<223> OTHER INFORMATION: Synthetic

<400> SEQUENCE: 256

Gln Gln Tyr Lys Ser Tyr Pro Leu Thr
 1               5

<210> SEQ ID NO 257
<211> LENGTH: 372
<212> TYPE: DNA
<213> ORGANISM: Artificial Sequence
<220> FEATURE:
<223> OTHER INFORMATION: Synthetic

<400> SEQUENCE: 257
gaggtgcagc tgttgcagtc cggggggaggc ttggtccagc ctgggggtc cctgagactc         60 tcctgtgcag cctctggatt caccttagt cactattgga tgagctgggt ccgccagggt        120
cctgggaagg ggctggagtg ggtggccact attaagaaag atggaagtga gagctactat        180
gtggactctg tgaggggccg attcaccatt tccagagaca cgccaagaa ctcactgtat        240 ttgcaaatga acagcctgcg aaccgaggac acggctgtgt attactgtgc gagagatata        300
gtgactccga atgtgggtta ttacttcgga atggacgtct ggggccaagg gaccacggtc        360
accgtctcct ca                                                           372

<210> SEQ ID NO 258
<211> LENGTH: 124
<212> TYPE: PRT
<213> ORGANISM: Artificial Sequence
<220> FEATURE:
<223> OTHER INFORMATION: Synthetic

<400> SEQUENCE: 258

```
Glu Val Gln Leu Leu Gln Ser Gly Gly Gly Leu Val Gln Pro Gly Gly
 1               5                  10                  15

Ser Leu Arg Leu Ser Cys Ala Ala Ser Gly Phe Thr Phe Ser His Tyr
            20                  25                  30

Trp Met Ser Trp Val Arg Gln Gly Pro Gly Lys Gly Leu Glu Trp Val
        35                  40                  45

Ala Thr Ile Lys Lys Asp Gly Ser Glu Ser Tyr Tyr Val Asp Ser Val
    50                  55                  60

Arg Gly Arg Phe Thr Ile Ser Arg Asp Asn Ala Lys Asn Ser Leu Tyr
65                  70                  75                  80

Leu Gln Met Asn Ser Leu Arg Thr Glu Asp Thr Ala Val Tyr Tyr Cys
                85                  90                  95

Ala Arg Asp Ile Val Thr Pro Asn Val Gly Tyr Tyr Phe Gly Met Asp
            100                 105                 110

Val Trp Gly Gln Gly Thr Thr Val Thr Val Ser Ser
        115                 120
```

<210> SEQ ID NO 259
<211> LENGTH: 24
<212> TYPE: DNA
<213> ORGANISM: Artificial Sequence
<220> FEATURE:
<223> OTHER INFORMATION: Synthetic

<400> SEQUENCE: 259
ggattcacct ttagtcacta ttgg                                            24

<210> SEQ ID NO 260
<211> LENGTH: 8
<212> TYPE: PRT
<213> ORGANISM: Artificial Sequence
<220> FEATURE:
<223> OTHER INFORMATION: Synthetic

<400> SEQUENCE: 260

```
Gly Phe Thr Phe Ser His Tyr Trp
 1               5
```

<210> SEQ ID NO 261
<211> LENGTH: 24
<212> TYPE: DNA
<213> ORGANISM: Artificial Sequence
<220> FEATURE:
<223> OTHER INFORMATION: Synthetic

<400> SEQUENCE: 261
attaagaaag atggaagtga gagc                                            24

<210> SEQ ID NO 262
<211> LENGTH: 8
<212> TYPE: PRT
<213> ORGANISM: Artificial Sequence
<220> FEATURE:
<223> OTHER INFORMATION: Synthetic

<400> SEQUENCE: 262

Ile Lys Lys Asp Gly Ser Glu Ser
1               5

<210> SEQ ID NO 263
<211> LENGTH: 51
<212> TYPE: DNA
<213> ORGANISM: Artificial Sequence
<220> FEATURE:
<223> OTHER INFORMATION: Synthetic

<400> SEQUENCE: 263
gcgagagata tagtgactcc gaatgtgggt tattacttcg gaatggacgt c            51

<210> SEQ ID NO 264
<211> LENGTH: 17
<212> TYPE: PRT
<213> ORGANISM: Artificial Sequence
<220> FEATURE:
<223> OTHER INFORMATION: Synthetic

<400> SEQUENCE: 264

Ala Arg Asp Ile Val Thr Pro Asn Val Gly Tyr Tyr Phe Gly Met Asp
1               5                   10                  15
Val

<210> SEQ ID NO 265
<211> LENGTH: 321
<212> TYPE: DNA
<213> ORGANISM: Artificial Sequence
<220> FEATURE:
<223> OTHER INFORMATION: Synthetic

<400> SEQUENCE: 265
gacatccaga tgacccagtc tccttccacc ctgtctgcat ctgtaggaga cagagtcacc      60
atcacttgcc gggccagtca gagtattagt agttggttgt cctggtatca gcagaaacct    120
gggaaagccc ctaagctcct gatctatatg gcgtctactt tagaaagtgg ggtcccatca    180
aggttcagcg gcagtggatc tgggacagat ttcactctca ccatcaccag cctgcagcct    240
gatgattttg caacttatta ctgccaacag tctaatagtt attctcggac gttcggccac    300
gggaccaagc tggagatcaa a                                              321

<210> SEQ ID NO 266
<211> LENGTH: 107
<212> TYPE: PRT
<213> ORGANISM: Artificial Sequence
<220> FEATURE:
<223> OTHER INFORMATION: Synthetic

<400> SEQUENCE: 266

Asp Ile Gln Met Thr Gln Ser Pro Ser Thr Leu Ser Ala Ser Val Gly
1               5                   10                  15
Asp Arg Val Thr Ile Thr Cys Arg Ala Ser Gln Ser Ile Ser Ser Trp
            20                  25                  30
Leu Ser Trp Tyr Gln Gln Lys Pro Gly Lys Ala Pro Lys Leu Leu Ile
        35                  40                  45
Tyr Met Ala Ser Thr Leu Glu Ser Gly Val Pro Ser Arg Phe Ser Gly
    50                  55                  60
Ser Gly Ser Gly Thr Asp Phe Thr Leu Thr Ile Thr Ser Leu Gln Pro
65                  70                  75                  80

Asp Asp Phe Ala Thr Tyr Tyr Cys Gln Gln Ser Asn Ser Tyr Ser Arg
            85                  90                  95

Thr Phe Gly His Gly Thr Lys Leu Glu Ile Lys
            100                 105

<210> SEQ ID NO 267
<211> LENGTH: 18
<212> TYPE: DNA
<213> ORGANISM: Artificial Sequence
<220> FEATURE:
<223> OTHER INFORMATION: Synthetic

<400> SEQUENCE: 267
cagagtatta gtagttgg                                                 18

<210> SEQ ID NO 268
<211> LENGTH: 6
<212> TYPE: PRT
<213> ORGANISM: Artificial Sequence
<220> FEATURE:
<223> OTHER INFORMATION: Synthetic

<400> SEQUENCE: 268

Gln Ser Ile Ser Ser Trp
 1               5

<210> SEQ ID NO 269
<211> LENGTH: 9
<212> TYPE: DNA
<213> ORGANISM: Artificial Sequence
<220> FEATURE:
<223> OTHER INFORMATION: Synthetic

<400> SEQUENCE: 269 atggcgtct                                                            9

<210> SEQ ID NO 270
<211> LENGTH: 3
<212> TYPE: PRT
<213> ORGANISM: Artificial Sequence
<220> FEATURE:
<223> OTHER INFORMATION: Synthetic

<400> SEQUENCE: 270

Met Ala Ser
 1

<210> SEQ ID NO 271
<211> LENGTH: 27
<212> TYPE: DNA
<213> ORGANISM: Artificial Sequence
<220> FEATURE:
<223> OTHER INFORMATION: Synthetic

<400> SEQUENCE: 271
caacagtcta atagttattc tcggacg                                       27

<210> SEQ ID NO 272
<211> LENGTH: 9
<212> TYPE: PRT
<213> ORGANISM: Artificial Sequence
<220> FEATURE:
<223> OTHER INFORMATION: Synthetic

<400> SEQUENCE: 272

Gln Gln Ser Asn Ser Tyr Ser Arg Thr

<210> SEQ ID NO 273
<211> LENGTH: 372
<212> TYPE: DNA
<213> ORGANISM: Artificial Sequence
<220> FEATURE:
<223> OTHER INFORMATION: Synthetic

<400> SEQUENCE: 273

```
caggtgcagc tggtggagtc cggggggaggc ctggtccagc ctggggggtc cctgagactc    60
tcctgtgcag ccgctggatt cacttttagt cactattgga tgagctgggt ccgccaggct   120
cctgggaagg ggctggagtg ggtggccacc ataaagaaag atggaagtga agatactat   180
gtggactctg tgaagggccg attcaccatt tccagagaca cgccaggaa ctcaatgtat   240
ttggaaatga atagcctgcg aaccgaggac acggctatat attactgtgc gagagatata   300
gtgactccga atacggacta ctacttcggt atggacgtct ggggccaagg gaccacggtc   360
accgtctcct ca                                                       372
```

<210> SEQ ID NO 274
<211> LENGTH: 124
<212> TYPE: PRT
<213> ORGANISM: Artificial Sequence
<220> FEATURE:
<223> OTHER INFORMATION: Synthetic

<400> SEQUENCE: 274

```
Gln Val Gln Leu Val Glu Ser Gly Gly Gly Leu Val Gln Pro Gly Gly
 1               5                  10                  15

Ser Leu Arg Leu Ser Cys Ala Ala Ala Gly Phe Thr Phe Ser His Tyr
            20                  25                  30

Trp Met Ser Trp Val Arg Gln Ala Pro Gly Lys Gly Leu Glu Trp Val
        35                  40                  45

Ala Thr Ile Lys Lys Asp Gly Ser Glu Arg Tyr Tyr Val Asp Ser Val
    50                  55                  60

Lys Gly Arg Phe Thr Ile Ser Arg Asp Asn Ala Arg Asn Ser Met Tyr
65                  70                  75                  80

Leu Glu Met Asn Ser Leu Arg Thr Glu Asp Thr Ala Ile Tyr Tyr Cys
                85                  90                  95

Ala Arg Asp Ile Val Thr Pro Asn Thr Asp Tyr Tyr Phe Gly Met Asp
            100                 105                 110

Val Trp Gly Gln Gly Thr Thr Val Thr Val Ser Ser
        115                 120
```

<210> SEQ ID NO 275
<211> LENGTH: 24
<212> TYPE: DNA
<213> ORGANISM: Artificial Sequence
<220> FEATURE:
<223> OTHER INFORMATION: Synthetic

<400> SEQUENCE: 275

```
ggattcactt ttagtcacta ttgg                                          24
```

<210> SEQ ID NO 276
<211> LENGTH: 8
<212> TYPE: PRT
<213> ORGANISM: Artificial Sequence
<220> FEATURE:
<223> OTHER INFORMATION: Synthetic

<400> SEQUENCE: 276

Gly Phe Thr Phe Ser His Tyr Trp
1               5

<210> SEQ ID NO 277
<211> LENGTH: 24
<212> TYPE: DNA
<213> ORGANISM: Artificial Sequence
<220> FEATURE:
<223> OTHER INFORMATION: Synthetic

<400> SEQUENCE: 277
ataaagaaag atggaagtga gaga                                          24

<210> SEQ ID NO 278
<211> LENGTH: 8
<212> TYPE: PRT
<213> ORGANISM: Artificial Sequence
<220> FEATURE:
<223> OTHER INFORMATION: Synthetic

<400> SEQUENCE: 278

Ile Lys Lys Asp Gly Ser Glu Arg
1               5

<210> SEQ ID NO 279
<211> LENGTH: 51
<212> TYPE: DNA
<213> ORGANISM: Artificial Sequence
<220> FEATURE:
<223> OTHER INFORMATION: Synthetic

<400> SEQUENCE: 279
gcgagagata tagtgactcc gaatacggac tactacttcg gtatggacgt c            51

<210> SEQ ID NO 280
<211> LENGTH: 17
<212> TYPE: PRT
<213> ORGANISM: Artificial Sequence
<220> FEATURE:
<223> OTHER INFORMATION: Synthetic

<400> SEQUENCE: 280

Ala Arg Asp Ile Val Thr Pro Asn Thr Asp Tyr Tyr Phe Gly Met Asp
1               5                   10                  15
Val

<210> SEQ ID NO 281
<211> LENGTH: 321
<212> TYPE: DNA
<213> ORGANISM: Artificial Sequence
<220> FEATURE:
<223> OTHER INFORMATION: Synthetic

<400> SEQUENCE: 281
gacatccagt tgacccagtc tccttccacc ctgtctgcat ctgtaggaga cagagtcacc    60
atcacttgcc gggccagtca gagttttaat aactggttgt cctggtatca gcagaaacct   120
gggaaagccc ctaagctcct gatctatatg gcgtctactt tagaaagtgg ggtcccatca   180
aggttcagcg gcagtggatc tgggacagat ttcactctca ccatcaacag cctgcagcct   240
gatgattttg caacttatta ctgccaacag tctaatagtt attctcggac gttcggccac   300
gggaccaagg tggaaatcaa a                                             321

<210> SEQ ID NO 282
<211> LENGTH: 107
<212> TYPE: PRT
<213> ORGANISM: Artificial Sequence
<220> FEATURE:
<223> OTHER INFORMATION: Synthetic

<400> SEQUENCE: 282

Asp Ile Gln Leu Thr Gln Ser Pro Ser Thr Leu Ser Ala Ser Val Gly
1               5                   10                  15

Asp Arg Val Thr Ile Thr Cys Arg Ala Ser Gln Ser Phe Asn Asn Trp
            20                  25                  30

Leu Ser Trp Tyr Gln Gln Lys Pro Gly Lys Ala Pro Lys Leu Leu Ile
        35                  40                  45

Tyr Met Ala Ser Thr Leu Glu Ser Gly Val Pro Ser Arg Phe Ser Gly
50                  55                  60

Ser Gly Ser Gly Thr Asp Phe Thr Leu Thr Ile Asn Ser Leu Gln Pro
65                  70                  75                  80

Asp Asp Phe Ala Thr Tyr Tyr Cys Gln Gln Ser Asn Ser Tyr Ser Arg
                85                  90                  95

Thr Phe Gly His Gly Thr Lys Val Glu Ile Lys
            100                 105

<210> SEQ ID NO 283
<211> LENGTH: 18
<212> TYPE: DNA
<213> ORGANISM: Artificial Sequence
<220> FEATURE:
<223> OTHER INFORMATION: Synthetic

<400> SEQUENCE: 283 cagagttta ataactgg                                                          18

<210> SEQ ID NO 284
<211> LENGTH: 6
<212> TYPE: PRT
<213> ORGANISM: Artificial Sequence
<220> FEATURE:
<223> OTHER INFORMATION: Synthetic

<400> SEQUENCE: 284

Gln Ser Phe Asn Asn Trp
1               5

<210> SEQ ID NO 285
<211> LENGTH: 9
<212> TYPE: DNA
<213> ORGANISM: Artificial Sequence
<220> FEATURE:
<223> OTHER INFORMATION: Synthetic

<400> SEQUENCE: 285 atggcgtct                                                                   9

<210> SEQ ID NO 286
<211> LENGTH: 3
<212> TYPE: PRT
<213> ORGANISM: Artificial Sequence
<220> FEATURE:
<223> OTHER INFORMATION: Synthetic

<400> SEQUENCE: 286

Met Ala Ser
 1

<210> SEQ ID NO 287
<211> LENGTH: 27
<212> TYPE: DNA
<213> ORGANISM: Artificial Sequence
<220> FEATURE:
<223> OTHER INFORMATION: Synthetic

<400> SEQUENCE: 287
caacagtcta atagttattc tcggacg                                           27

<210> SEQ ID NO 288
<211> LENGTH: 9
<212> TYPE: PRT
<213> ORGANISM: Artificial Sequence
<220> FEATURE:
<223> OTHER INFORMATION: Synthetic

<400> SEQUENCE: 288

Gln Gln Ser Asn Ser Tyr Ser Arg Thr
 1               5

<210> SEQ ID NO 289
<211> LENGTH: 381
<212> TYPE: DNA
<213> ORGANISM: Artificial Sequence
<220> FEATURE:
<223> OTHER INFORMATION: Synthetic

<400> SEQUENCE: 289
caggtgcagc tggtggagtc tgggggaagt tggtccagc cggggggtc cctgagactc          60 gcctgtacag cctctggatt cacctttagt agctattgga tgagctgggt ccgccaggct       120
ccagggaagg gctggagtg gtggccaac atacaacaag atgaaaatga aaatactat         180 gtggactctg tgaagggccg attctccatc tccagagaca cgccaagaa gtcactgtat       240 ctgcaaatga acagcctgag agtcgaagat acggctgtgt atttctgtgc gagagatctt      300
gtgccacctc gtcaggggga ttattaccac tatttcggta tggacgtctg gggccaaggg      360
accacggtca ccgtctcctc a                                                 381

<210> SEQ ID NO 290
<211> LENGTH: 127
<212> TYPE: PRT
<213> ORGANISM: Artificial Sequence
<220> FEATURE:
<223> OTHER INFORMATION: Synthetic

<400> SEQUENCE: 290

Gln Val Gln Leu Val Glu Ser Gly Gly Ser Leu Val Gln Pro Gly Gly
 1               5                  10                  15

Ser Leu Arg Leu Ala Cys Thr Ala Ser Gly Phe Thr Phe Ser Ser Tyr
             20                  25                  30

Trp Met Ser Trp Val Arg Gln Ala Pro Gly Lys Gly Leu Glu Trp Val
         35                  40                  45

Ala Asn Ile Gln Gln Asp Glu Asn Glu Lys Tyr Tyr Val Asp Ser Val
     50                  55                  60

Lys Gly Arg Phe Ser Ile Ser Arg Asp Asn Ala Lys Lys Ser Leu Tyr
 65                  70                  75                  80

Leu Gln Met Asn Ser Leu Arg Val Glu Asp Thr Ala Val Tyr Phe Cys
                 85                  90                  95

Ala Arg Asp Leu Val Pro Pro Arg Gln Gly Asp Tyr Tyr His Tyr Phe
            100                 105                 110

Gly Met Asp Val Trp Gly Gln Gly Thr Thr Val Thr Val Ser Ser
        115                 120                 125

<210> SEQ ID NO 291
<211> LENGTH: 24
<212> TYPE: DNA
<213> ORGANISM: Artificial Sequence
<220> FEATURE:
<223> OTHER INFORMATION: Synthetic

<400> SEQUENCE: 291
ggattcacct ttagtagcta ttgg                                          24

<210> SEQ ID NO 292
<211> LENGTH: 8
<212> TYPE: PRT
<213> ORGANISM: Artificial Sequence
<220> FEATURE:
<223> OTHER INFORMATION: Synthetic

<400> SEQUENCE: 292

Gly Phe Thr Phe Ser Ser Tyr Trp
 1               5

<210> SEQ ID NO 293
<211> LENGTH: 24
<212> TYPE: DNA
<213> ORGANISM: Artificial Sequence
<220> FEATURE:
<223> OTHER INFORMATION: Synthetic

<400> SEQUENCE: 293
atacaacaag atgaaaatga gaaa                                          24

<210> SEQ ID NO 294
<211> LENGTH: 8
<212> TYPE: PRT
<213> ORGANISM: Artificial Sequence
<220> FEATURE:
<223> OTHER INFORMATION: Synthetic

<400> SEQUENCE: 294

Ile Gln Gln Asp Glu Asn Glu Lys
 1               5

<210> SEQ ID NO 295
<211> LENGTH: 60
<212> TYPE: DNA
<213> ORGANISM: Artificial Sequence
<220> FEATURE:
<223> OTHER INFORMATION: Synthetic

<400> SEQUENCE: 295
gcgagagatc ttgtgccacc tcgtcagggg gattattacc actatttcgg tatggacgtc   60

<210> SEQ ID NO 296
<211> LENGTH: 20
<212> TYPE: PRT
<213> ORGANISM: Artificial Sequence
<220> FEATURE:
<223> OTHER INFORMATION: Synthetic

<400> SEQUENCE: 296

Ala Arg Asp Leu Val Pro Pro Arg Gln Gly Asp Tyr Tyr His Tyr Phe
1               5                   10                  15

Gly Met Asp Val
            20

<210> SEQ ID NO 297
<211> LENGTH: 321
<212> TYPE: DNA
<213> ORGANISM: Artificial Sequence
<220> FEATURE:
<223> OTHER INFORMATION: Synthetic

<400> SEQUENCE: 297
gacatccagt tgacccagtc tccttccacc ctgtctgcat ctgtaggaga cagagtcacc    60
atcacttgcc gggccagtca gagtattagt gactggttgg cctggtatca gcagaaacca   120
gggaaagccc ctaatctcct gatctataag gcgtctactt tagaaagtgg ggtcccatca   180
aggttcagcg gcagtggatc tgggacagaa ttcactctca ccatcagcag cctgcagcct   240
gatgattttg caacttatta ctgccaacag tataatagtt attctcggac gttcggccaa   300
gggaccaagg tggaaatcaa a                                             321

<210> SEQ ID NO 298
<211> LENGTH: 107
<212> TYPE: PRT
<213> ORGANISM: Artificial Sequence
<220> FEATURE:
<223> OTHER INFORMATION: Synthetic

<400> SEQUENCE: 298

Asp Ile Gln Leu Thr Gln Ser Pro Ser Thr Leu Ser Ala Ser Val Gly
1               5                   10                  15

Asp Arg Val Thr Ile Thr Cys Arg Ala Ser Gln Ser Ile Ser Asp Trp
            20                  25                  30

Leu Ala Trp Tyr Gln Gln Lys Pro Gly Lys Ala Pro Asn Leu Leu Ile
        35                  40                  45

Tyr Lys Ala Ser Thr Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Ser Arg
                85                  90                  95

Thr Phe Gly Gln Gly Thr Lys Val Glu Ile Lys
            100                 105

<210> SEQ ID NO 299
<211> LENGTH: 18
<212> TYPE: DNA
<213> ORGANISM: Artificial Sequence
<220> FEATURE:
<223> OTHER INFORMATION: Synthetic

<400> SEQUENCE: 299
cagagtatta gtgactgg                                                  18

<210> SEQ ID NO 300
<211> LENGTH: 6
<212> TYPE: PRT
<213> ORGANISM: Artificial Sequence
<220> FEATURE:
<223> OTHER INFORMATION: Synthetic

<400> SEQUENCE: 300

Gln Ser Ile Ser Asp Trp
1               5

<210> SEQ ID NO 301
<211> LENGTH: 9
<212> TYPE: DNA
<213> ORGANISM: Artificial Sequence
<220> FEATURE:
<223> OTHER INFORMATION: Synthetic

<400> SEQUENCE: 301 aaggcgtct                                                                  9

<210> SEQ ID NO 302
<211> LENGTH: 3
<212> TYPE: PRT
<213> ORGANISM: Artificial Sequence
<220> FEATURE:
<223> OTHER INFORMATION: Synthetic

<400> SEQUENCE: 302

Lys Ala Ser
1

<210> SEQ ID NO 303
<211> LENGTH: 27
<212> TYPE: DNA
<213> ORGANISM: Artificial Sequence
<220> FEATURE:
<223> OTHER INFORMATION: Synthetic

<400> SEQUENCE: 303
caacagtata atagttattc tcggacg                                             27

<210> SEQ ID NO 304
<211> LENGTH: 9
<212> TYPE: PRT
<213> ORGANISM: Artificial Sequence
<220> FEATURE:
<223> OTHER INFORMATION: Synthetic

<400> SEQUENCE: 304

Gln Gln Tyr Asn Ser Tyr Ser Arg Thr
1               5

<210> SEQ ID NO 305
<211> LENGTH: 381
<212> TYPE: DNA
<213> ORGANISM: Artificial Sequence
<220> FEATURE:
<223> OTHER INFORMATION: Synthetic

<400> SEQUENCE: 305
caggtgcagc tggtggagtc tgggggaggc ttggtccagc ctgggggtc cctgagactc           60 tcctgtgcag cctctggatt caccttcagt agttattgga tgagttgggt ccgccaggtt         120
ccagggaagg ggctggagtg ggtggccaac atgaaccaag atggaactga gaaatactat         180
gtggactctg tgaagggccg actcaccata tccagagaaa atgtcaagaa ttcattgtat         240
ctgcaaatga acggcctgag agccgaagac acggctgtgt attactgtgc gagagatctt         300
gttccacctc gtcaggggga ttactactac tacttcggta tggacgtctg gggccatggg         360
acaatggtca ccgtctcttc a                                                  381

<210> SEQ ID NO 306
<211> LENGTH: 127
<212> TYPE: PRT
<213> ORGANISM: Artificial Sequence
<220> FEATURE:
<223> OTHER INFORMATION: Synthetic

<400> SEQUENCE: 306

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Val Pro Gly Lys Gly Leu Glu Trp Val
        35                  40                  45

Ala Asn Met Asn Gln Asp Gly Thr Glu Lys Tyr Tyr Val Asp Ser Val
    50                  55                  60

Lys Gly Arg Leu Thr Ile Ser Arg Glu Asn Val Lys Asn Ser Leu Tyr
65                  70                  75                  80

Leu Gln Met Asn Gly Leu Arg Ala Glu Asp Thr Ala Val Tyr Tyr Cys
                85                  90                  95

Ala Arg Asp Leu Val Pro Pro Arg Gln Gly Asp Tyr Tyr Tyr Tyr Phe
            100                 105                 110

Gly Met Asp Val Trp Gly His Gly Thr Met Val Thr Val Ser Ser
        115                 120                 125

<210> SEQ ID NO 307
<211> LENGTH: 24
<212> TYPE: DNA
<213> ORGANISM: Artificial Sequence
<220> FEATURE:
<223> OTHER INFORMATION: Synthetic

<400> SEQUENCE: 307
ggattcacct tcagtagtta ttgg                                          24

<210> SEQ ID NO 308
<211> LENGTH: 8
<212> TYPE: PRT
<213> ORGANISM: Artificial Sequence
<220> FEATURE:
<223> OTHER INFORMATION: Synthetic

<400> SEQUENCE: 308

Gly Phe Thr Phe Ser Ser Tyr Trp
1               5

<210> SEQ ID NO 309
<211> LENGTH: 24
<212> TYPE: DNA
<213> ORGANISM: Artificial Sequence
<220> FEATURE:
<223> OTHER INFORMATION: Synthetic

<400> SEQUENCE: 309
atgaaccaag atggaactga gaaa                                          24

<210> SEQ ID NO 310
<211> LENGTH: 8
<212> TYPE: PRT
<213> ORGANISM: Artificial Sequence
<220> FEATURE:
<223> OTHER INFORMATION: Synthetic

<400> SEQUENCE: 310

Met Asn Gln Asp Gly Thr Glu Lys
1               5

<210> SEQ ID NO 311
<211> LENGTH: 60
<212> TYPE: DNA
<213> ORGANISM: Artificial Sequence
<220> FEATURE:
<223> OTHER INFORMATION: Synthetic

<400> SEQUENCE: 311
gcgagagatc ttgttccacc tcgtcagggg gattactact actacttcgg tatggacgtc    60

<210> SEQ ID NO 312
<211> LENGTH: 20
<212> TYPE: PRT
<213> ORGANISM: Artificial Sequence
<220> FEATURE:
<223> OTHER INFORMATION: Synthetic

<400> SEQUENCE: 312

Ala Arg Asp Leu Val Pro Pro Arg Gln Gly Asp Tyr Tyr Tyr Phe
1               5                   10                  15

Gly Met Asp Val
            20

<210> SEQ ID NO 313
<211> LENGTH: 321
<212> TYPE: DNA
<213> ORGANISM: Artificial Sequence
<220> FEATURE:
<223> OTHER INFORMATION: Synthetic

<400> SEQUENCE: 313
gccatccaga tgacccagtc tccttccacc ctgtctgcat ctgtaggaga catcgtcacc    60
atcacttgcc gggccagtca gagtattagt gactggttgg cctggtatca gcagaaacca   120
gggaaagccc ctaaactcct gatttttaag gcgtctagtt tagaaagtgg ggtcccatca   180
aggttcagcg gcagtggatc tgggacagat ttcactctca ccatcagcag cctgcagcct   240
gatgattttg caacttacta ctgccaacag tataatagct attctcggac gttcggccaa   300
gggaccaaag tggatatcaa a                                              321

<210> SEQ ID NO 314
<211> LENGTH: 107
<212> TYPE: PRT
<213> ORGANISM: Artificial Sequence
<220> FEATURE:
<223> OTHER INFORMATION: Synthetic

<400> SEQUENCE: 314

Ala Ile Gln Met Thr Gln Ser Pro Ser Thr Leu Ser Ala Ser Val Gly
1               5                   10                  15

Asp Ile Val Thr Ile Thr Cys Arg Ala Ser Gln Ser Ile Ser Asp Trp
            20                  25                  30

Leu Ala Trp Tyr Gln Gln Lys Pro Gly Lys Ala Pro Lys Leu Leu Ile
        35                  40                  45

Phe Lys Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Asp Asp Phe Ala Thr Tyr Tyr Cys Gln Gln Tyr Asn Ser Tyr Ser Arg
            85                  90                  95

Thr Phe Gly Gln Gly Thr Lys Val Asp Ile Lys
            100                 105

<210> SEQ ID NO 315
<211> LENGTH: 18
<212> TYPE: DNA
<213> ORGANISM: Artificial Sequence
<220> FEATURE:
<223> OTHER INFORMATION: Synthetic

<400> SEQUENCE: 315
cagagtatta gtgactgg                                                 18

<210> SEQ ID NO 316
<211> LENGTH: 6
<212> TYPE: PRT
<213> ORGANISM: Artificial Sequence
<220> FEATURE:
<223> OTHER INFORMATION: Synthetic

<400> SEQUENCE: 316

Gln Ser Ile Ser Asp Trp
 1               5

<210> SEQ ID NO 317
<211> LENGTH: 9
<212> TYPE: DNA
<213> ORGANISM: Artificial Sequence
<220> FEATURE:
<223> OTHER INFORMATION: Synthetic

<400> SEQUENCE: 317 aaggcgtct                                                            9

<210> SEQ ID NO 318
<211> LENGTH: 3
<212> TYPE: PRT
<213> ORGANISM: Artificial Sequence
<220> FEATURE:
<223> OTHER INFORMATION: Synthetic

<400> SEQUENCE: 318

Lys Ala Ser
 1

<210> SEQ ID NO 319
<211> LENGTH: 27
<212> TYPE: DNA
<213> ORGANISM: Artificial Sequence
<220> FEATURE:
<223> OTHER INFORMATION: Synthetic

<400> SEQUENCE: 319
caacagtata atagctattc tcggacg                                       27

<210> SEQ ID NO 320
<211> LENGTH: 9
<212> TYPE: PRT
<213> ORGANISM: Artificial Sequence
<220> FEATURE:
<223> OTHER INFORMATION: Synthetic

<400> SEQUENCE: 320

Gln Gln Tyr Asn Ser Tyr Ser Arg Thr
 1               5

<210> SEQ ID NO 321
<211> LENGTH: 354
<212> TYPE: DNA
<213> ORGANISM: Artificial Sequence
<220> FEATURE:
<223> OTHER INFORMATION: Synthetic

<400> SEQUENCE: 321

```
caggtgcagc tggtggagtc tgggggaggc ttcgtccagc ctggggggtc cctgagactc    60
tcctgtgcag cctctggatt cacctttacc aactatgcca tgagctgggt ccgccaggct   120
ccagggaagg ggctggagtg ggtctcagct attagtggtg ttggtggtag cacatactac   180
gcagactccg tgaagggccg gttcaccatc tccagagaca cttccaagaa tatgctgtat   240
ctgcaaatga acagcctgag agccgaggac acggccgtat attactgtgc gaaagccccg   300
cactggggcc cctttggctc ctggggccag ggaaccctgg tcaccgtctc ctca         354
```

<210> SEQ ID NO 322
<211> LENGTH: 118
<212> TYPE: PRT
<213> ORGANISM: Artificial Sequence
<220> FEATURE:
<223> OTHER INFORMATION: Synthetic

<400> SEQUENCE: 322

Gln Val Gln Leu Val Glu Ser Gly Gly Gly Phe Val Gln Pro Gly Gly
 1               5                  10                  15
Ser Leu Arg Leu Ser Cys Ala Ala Ser Gly Phe Thr Phe Thr Asn Tyr
            20                  25                  30
Ala Met Ser Trp Val Arg Gln Ala Pro Gly Lys Gly Leu Glu Trp Val
        35                  40                  45
Ser Ala Ile Ser Gly Val Gly Gly Ser Thr Tyr Tyr Ala Asp Ser Val
    50                  55                  60
Lys Gly Arg Phe Thr Ile Ser Arg Asp Thr Ser Lys Asn Met Leu Tyr
65                  70                  75                  80
Leu Gln Met Asn Ser Leu Arg Ala Glu Asp Thr Ala Val Tyr Tyr Cys
                85                  90                  95
Ala Lys Ala Pro His Trp Gly Pro Phe Gly Ser Trp Gly Gln Gly Thr
            100                 105                 110
Leu Val Thr Val Ser Ser
        115

<210> SEQ ID NO 323
<211> LENGTH: 24
<212> TYPE: DNA
<213> ORGANISM: Artificial Sequence
<220> FEATURE:
<223> OTHER INFORMATION: Synthetic

<400> SEQUENCE: 323
ggattcacct ttaccaacta tgcc    24

<210> SEQ ID NO 324
<211> LENGTH: 8
<212> TYPE: PRT
<213> ORGANISM: Artificial Sequence
<220> FEATURE:
<223> OTHER INFORMATION: Synthetic

<400> SEQUENCE: 324

Gly Phe Thr Phe Thr Asn Tyr Ala
1               5

<210> SEQ ID NO 325
<211> LENGTH: 24
<212> TYPE: DNA
<213> ORGANISM: Artificial Sequence
<220> FEATURE:
<223> OTHER INFORMATION: Synthetic

<400> SEQUENCE: 325
attagtggtg ttggtggtag caca                                    24

<210> SEQ ID NO 326
<211> LENGTH: 8
<212> TYPE: PRT
<213> ORGANISM: Artificial Sequence
<220> FEATURE:
<223> OTHER INFORMATION: Synthetic

<400> SEQUENCE: 326

Ile Ser Gly Val Gly Gly Ser Thr
1               5

<210> SEQ ID NO 327
<211> LENGTH: 33
<212> TYPE: DNA
<213> ORGANISM: Artificial Sequence
<220> FEATURE:
<223> OTHER INFORMATION: Synthetic

<400> SEQUENCE: 327
gcgaaagccc cgcactgggg cccctttggc tcc                          33

<210> SEQ ID NO 328
<211> LENGTH: 11
<212> TYPE: PRT
<213> ORGANISM: Artificial Sequence
<220> FEATURE:
<223> OTHER INFORMATION: Synthetic

<400> SEQUENCE: 328

Ala Lys Ala Pro His Trp Gly Pro Phe Gly Ser
1               5                   10

<210> SEQ ID NO 329
<211> LENGTH: 339
<212> TYPE: DNA
<213> ORGANISM: Artificial Sequence
<220> FEATURE:
<223> OTHER INFORMATION: Synthetic

<400> SEQUENCE: 329
gacatccagt tgacccagtc tccagactcc ctggctgtgt ctctgggcga gagggccacc    60
atcaactgca agtccagcca gagtgtttta tacaggtcca acaataagaa gttcttagtt   120
tggtaccagc agaaaccagg acagcctcct aagccgctca tttactgggc atctacccgg   180
gaatccgggg tccctgaccg attcagtggc agcgggtctg ggacagattt cactctcacc   240
atcaacagcc tgcaggctga agatgtggca gtttattact gtcaacaata ttatagtact   300
ccgtacactt ttggccaggg gaccaaggtg gagatcaaa                         339

<210> SEQ ID NO 330

```
<211> LENGTH: 113
<212> TYPE: PRT
<213> ORGANISM: Artificial Sequence
<220> FEATURE:
<223> OTHER INFORMATION: Synthetic

<400> SEQUENCE: 330
```

Asp Ile Gln Leu Thr Gln Ser Pro Asp Ser Leu Ala Val Ser Leu Gly
 1               5                  10                  15

Glu Arg Ala Thr Ile Asn Cys Lys Ser Ser Gln Ser Val Leu Tyr Arg
            20                  25                  30

Ser Asn Asn Lys Lys Phe Leu Val Trp Tyr Gln Gln Lys Pro Gly Gln
        35                  40                  45

Pro Pro Lys Pro Leu Ile Tyr Trp Ala Ser Thr Arg Glu Ser Gly Val
50                  55                  60

Pro Asp Arg Phe Ser Gly Ser Gly Ser Gly Thr Asp Phe Thr Leu Thr
65                  70                  75                  80

Ile Asn Ser Leu Gln Ala Glu Asp Val Ala Val Tyr Tyr Cys Gln Gln
                85                  90                  95

Tyr Tyr Ser Thr Pro Tyr Thr Phe Gly Gln Gly Thr Lys Val Glu Ile
            100                 105                 110

Lys

```
<210> SEQ ID NO 331
<211> LENGTH: 36
<212> TYPE: DNA
<213> ORGANISM: Artificial Sequence
<220> FEATURE:
<223> OTHER INFORMATION: Synthetic

<400> SEQUENCE: 331
cagagtgttt tatacaggtc caacaataag aagttc                             36

<210> SEQ ID NO 332
<211> LENGTH: 12
<212> TYPE: PRT
<213> ORGANISM: Artificial Sequence
<220> FEATURE:
<223> OTHER INFORMATION: Synthetic

<400> SEQUENCE: 332
```

Gln Ser Val Leu Tyr Arg Ser Asn Asn Lys Lys Phe
 1               5                  10

```
<210> SEQ ID NO 333
<211> LENGTH: 9
<212> TYPE: DNA
<213> ORGANISM: Artificial Sequence
<220> FEATURE:
<223> OTHER INFORMATION: Synthetic

<400> SEQUENCE: 333 tgggcatct                                                            9

<210> SEQ ID NO 334
<211> LENGTH: 3
<212> TYPE: PRT
<213> ORGANISM: Artificial Sequence
<220> FEATURE:
<223> OTHER INFORMATION: Synthetic

<400> SEQUENCE: 334
```

Trp Ala Ser

<210> SEQ ID NO 335
<211> LENGTH: 27
<212> TYPE: DNA
<213> ORGANISM: Artificial Sequence
<220> FEATURE:
<223> OTHER INFORMATION: Synthetic

<400> SEQUENCE: 335
caacaatatt atagtactcc gtacact                                    27

<210> SEQ ID NO 336
<211> LENGTH: 9
<212> TYPE: PRT
<213> ORGANISM: Artificial Sequence
<220> FEATURE:
<223> OTHER INFORMATION: Synthetic

<400> SEQUENCE: 336

Gln Gln Tyr Tyr Ser Thr Pro Tyr Thr
 1               5

<210> SEQ ID NO 337
<211> LENGTH: 527
<212> TYPE: PRT
<213> ORGANISM: Artificial Sequence
<220> FEATURE:
<223> OTHER INFORMATION: Synthetic

<400> SEQUENCE: 337

Leu Val Val Thr Pro Pro Gly Pro Glu Leu Val Leu Asn Val Ser Ser
 1               5                  10                  15

Thr Phe Val Leu Thr Cys Ser Gly Ser Ala Pro Val Val Trp Glu Arg
            20                  25                  30

Met Ser Gln Glu Pro Pro Gln Glu Met Ala Lys Ala Gln Asp Gly Thr
        35                  40                  45

Phe Ser Ser Val Leu Thr Leu Thr Asn Leu Thr Gly Leu Asp Thr Gly
    50                  55                  60

Glu Tyr Phe Cys Thr His Asn Asp Ser Arg Gly Leu Glu Thr Asp Glu
65                  70                  75                  80

Arg Lys Arg Leu Tyr Ile Phe Val Pro Asp Pro Thr Val Gly Phe Leu
                85                  90                  95

Pro Asn Asp Ala Glu Glu Leu Phe Ile Phe Leu Thr Glu Ile Thr Glu
            100                 105                 110

Ile Thr Ile Pro Cys Arg Val Thr Asp Pro Gln Leu Val Val Thr Leu
        115                 120                 125

His Glu Lys Lys Gly Asp Val Ala Leu Pro Val Pro Tyr Asp His Gln
    130                 135                 140

Arg Gly Phe Phe Gly Ile Phe Glu Asp Arg Ser Tyr Ile Cys Lys Thr
145                 150                 155                 160

Thr Ile Gly Asp Arg Glu Val Asp Ser Asp Ala Tyr Tyr Val Tyr Arg
                165                 170                 175

Leu Gln Val Ser Ser Ile Asn Val Ser Val Asn Ala Val Gln Thr Val
            180                 185                 190

Val Arg Gln Gly Glu Asn Ile Thr Leu Met Cys Ile Val Ile Gly Asn
        195                 200                 205

Glu Val Val Asn Phe Glu Trp Thr Tyr Pro Arg Lys Glu Ser Gly Arg
    210                 215                 220

```
Leu Val Glu Pro Val Thr Asp Phe Leu Leu Asp Met Pro Tyr His Ile
225                 230                 235                 240

Arg Ser Ile Leu His Ile Pro Ser Ala Glu Leu Glu Asp Ser Gly Thr
            245                 250                 255

Tyr Thr Cys Asn Val Thr Glu Ser Val Asn Asp His Gln Asp Glu Lys
            260                 265                 270

Ala Ile Asn Ile Thr Val Val Glu Ser Gly Tyr Val Arg Leu Leu Gly
            275                 280                 285

Glu Val Gly Thr Leu Gln Phe Ala Glu Leu His Arg Ser Arg Thr Leu
            290                 295                 300

Gln Val Val Phe Glu Ala Tyr Pro Pro Thr Val Leu Trp Phe Lys
305                 310                 315                 320

Asp Asn Arg Thr Leu Gly Asp Ser Ser Ala Gly Glu Ile Ala Leu Ser
            325                 330                 335

Thr Arg Asn Val Ser Glu Thr Arg Tyr Val Ser Glu Leu Thr Leu Val
            340                 345                 350

Arg Val Lys Val Ala Glu Ala Gly His Tyr Thr Met Arg Ala Phe His
            355                 360                 365

Glu Asp Ala Glu Val Gln Leu Ser Phe Gln Leu Gln Ile Asn Val Pro
370                 375                 380

Val Arg Val Leu Glu Leu Ser Glu Ser His Pro Asp Ser Gly Glu Gln
385                 390                 395                 400

Thr Val Arg Cys Arg Gly Arg Gly Met Pro Gln Pro Asn Ile Ile Trp
            405                 410                 415

Ser Ala Cys Arg Asp Leu Lys Arg Cys Pro Arg Glu Leu Pro Pro Thr
            420                 425                 430

Leu Leu Gly Asn Ser Ser Glu Glu Ser Gln Leu Glu Thr Asn Val
            435                 440                 445

Thr Tyr Trp Glu Glu Glu Gln Glu Phe Glu Val Val Ser Thr Leu Arg
450                 455                 460

Leu Gln His Val Asp Arg Pro Leu Ser Val Arg Cys Thr Leu Arg Asn
465                 470                 475                 480

Ala Val Gly Gln Asp Thr Gln Glu Val Ile Val Pro His Ser Leu
            485                 490                 495

Pro Phe Lys Glu Gln Lys Leu Ile Ser Glu Glu Asp Leu Gly Gly Glu
            500                 505                 510

Gln Lys Leu Ile Ser Glu Glu Asp Leu His His His His His His
            515                 520                 525

<210> SEQ ID NO 338
<211> LENGTH: 732
<212> TYPE: PRT
<213> ORGANISM: Artificial Sequence
<220> FEATURE:
<223> OTHER INFORMATION: Synthetic

<400> SEQUENCE: 338

Leu Val Val Thr Pro Pro Gly Pro Glu Leu Val Leu Asn Val Ser Ser
1               5                   10                  15

Thr Phe Val Leu Thr Cys Ser Gly Ser Ala Pro Val Val Trp Glu Arg
            20                  25                  30

Met Ser Gln Glu Pro Pro Gln Glu Met Ala Lys Ala Gln Asp Gly Thr
            35                  40                  45

Phe Ser Ser Val Leu Thr Leu Thr Asn Leu Thr Gly Leu Asp Thr Gly
        50                  55                  60
```

```
Glu Tyr Phe Cys Thr His Asn Asp Ser Arg Gly Leu Glu Thr Asp Glu
 65                  70                  75                  80

Arg Lys Arg Leu Tyr Ile Phe Val Pro Asp Pro Thr Val Gly Phe Leu
                 85                  90                  95

Pro Asn Asp Ala Glu Glu Leu Phe Ile Phe Leu Thr Glu Ile Thr Glu
            100                 105                 110

Ile Thr Ile Pro Cys Arg Val Thr Asp Pro Gln Leu Val Thr Leu
            115                 120                 125

His Glu Lys Lys Gly Asp Val Ala Leu Pro Val Pro Tyr Asp His Gln
        130                 135                 140

Arg Gly Phe Phe Gly Ile Phe Glu Asp Arg Ser Tyr Ile Cys Lys Thr
145                 150                 155                 160

Thr Ile Gly Asp Arg Glu Val Asp Ser Asp Ala Tyr Tyr Val Tyr Arg
                165                 170                 175

Leu Gln Val Ser Ser Ile Asn Val Ser Val Asn Ala Val Gln Thr Val
                180                 185                 190

Val Arg Gln Gly Glu Asn Ile Thr Leu Met Cys Ile Val Ile Gly Asn
        195                 200                 205

Glu Val Val Asn Phe Glu Trp Thr Tyr Pro Arg Lys Glu Ser Gly Arg
210                 215                 220

Leu Val Glu Pro Val Thr Asp Phe Leu Leu Asp Met Pro Tyr His Ile
225                 230                 235                 240

Arg Ser Ile Leu His Ile Pro Ser Ala Glu Leu Glu Asp Ser Gly Thr
                245                 250                 255

Tyr Thr Cys Asn Val Thr Glu Ser Val Asn Asp His Gln Asp Glu Lys
                260                 265                 270

Ala Ile Asn Ile Thr Val Val Glu Ser Gly Tyr Val Arg Leu Leu Gly
                275                 280                 285

Glu Val Gly Thr Leu Gln Phe Ala Glu Leu His Arg Ser Arg Thr Leu
        290                 295                 300

Gln Val Val Phe Glu Ala Tyr Pro Pro Pro Thr Val Leu Trp Phe Lys
305                 310                 315                 320

Asp Asn Arg Thr Leu Gly Asp Ser Ser Ala Gly Glu Ile Ala Leu Ser
                325                 330                 335

Thr Arg Asn Val Ser Glu Thr Arg Tyr Val Ser Glu Leu Thr Leu Val
                340                 345                 350

Arg Val Lys Val Ala Glu Ala Gly His Tyr Thr Met Arg Ala Phe His
                355                 360                 365

Glu Asp Ala Glu Val Gln Leu Ser Phe Gln Leu Gln Ile Asn Val Pro
        370                 375                 380

Val Arg Val Leu Glu Leu Ser Glu Ser His Pro Asp Ser Gly Glu Gln
385                 390                 395                 400

Thr Val Arg Cys Arg Gly Arg Gly Met Pro Gln Pro Asn Ile Ile Trp
                405                 410                 415

Ser Ala Cys Arg Asp Leu Lys Arg Cys Pro Arg Glu Leu Pro Pro Thr
                420                 425                 430

Leu Leu Gly Asn Ser Ser Glu Glu Glu Ser Gln Leu Glu Thr Asn Val
            435                 440                 445

Thr Tyr Trp Glu Glu Glu Gln Glu Phe Glu Val Val Ser Thr Leu Arg
            450                 455                 460

Leu Gln His Val Asp Arg Pro Leu Ser Val Arg Cys Thr Leu Arg Asn
465                 470                 475                 480

Ala Val Gly Gln Asp Thr Gln Glu Val Ile Val Val Pro His Ser Leu
```

```
                        485                 490                 495
Pro Phe Lys Glu Pro Arg Gly Pro Thr Ile Lys Pro Cys Pro Pro Cys
                    500                 505                 510

Lys Cys Pro Ala Pro Asn Leu Leu Gly Gly Pro Ser Val Phe Ile Phe
                515                 520                 525

Pro Pro Lys Ile Lys Asp Val Leu Met Ile Ser Leu Ser Pro Ile Val
            530                 535                 540

Thr Cys Val Val Val Asp Val Ser Glu Asp Asp Pro Asp Val Gln Ile
545                 550                 555                 560

Ser Trp Phe Val Asn Asn Val Glu Val His Thr Ala Gln Thr Gln Thr
                565                 570                 575

His Arg Glu Asp Tyr Asn Ser Thr Leu Arg Val Val Ser Ala Leu Pro
                580                 585                 590

Ile Gln His Gln Asp Trp Met Ser Gly Lys Glu Phe Lys Cys Lys Val
                595                 600                 605

Asn Asn Lys Asp Leu Pro Ala Pro Ile Glu Arg Thr Ile Ser Lys Pro
            610                 615                 620

Lys Gly Ser Val Arg Ala Pro Gln Val Tyr Val Leu Pro Pro Pro Glu
625                 630                 635                 640

Glu Glu Met Thr Lys Lys Gln Val Thr Leu Thr Cys Met Val Thr Asp
                    645                 650                 655

Phe Met Pro Glu Asp Ile Tyr Val Glu Trp Thr Asn Asn Gly Lys Thr
                660                 665                 670

Glu Leu Asn Tyr Lys Asn Thr Glu Pro Val Leu Asp Ser Asp Gly Ser
            675                 680                 685

Tyr Phe Met Tyr Ser Lys Leu Arg Val Glu Lys Lys Asn Trp Val Glu
        690                 695                 700

Arg Asn Ser Tyr Ser Cys Ser Val Val His Glu Gly Leu His Asn His
705                 710                 715                 720

His Thr Thr Lys Ser Phe Ser Arg Thr Pro Gly Lys
                725                 730

<210> SEQ ID NO 339
<211> LENGTH: 726
<212> TYPE: PRT
<213> ORGANISM: Artificial Sequence
<220> FEATURE:
<223> OTHER INFORMATION: Synthetic

<400> SEQUENCE: 339

Leu Val Val Thr Pro Gly Pro Glu Leu Val Leu Asn Val Ser Ser
  1               5                  10                  15

Thr Phe Val Leu Thr Cys Ser Gly Ser Ala Pro Val Val Trp Glu Arg
                 20                  25                  30

Met Ser Gln Glu Pro Pro Gln Glu Met Ala Lys Ala Gln Asp Gly Thr
             35                  40                  45

Phe Ser Ser Val Leu Thr Leu Thr Asn Leu Thr Gly Leu Asp Thr Gly
         50                  55                  60

Glu Tyr Phe Cys Thr His Asn Asp Ser Arg Gly Leu Glu Thr Asp Glu
65                   70                  75                  80

Arg Lys Arg Leu Tyr Ile Phe Val Pro Asp Pro Thr Val Gly Phe Leu
                 85                  90                  95

Pro Asn Asp Ala Glu Glu Leu Phe Ile Phe Leu Thr Glu Ile Thr Glu
             100                 105                 110

Ile Thr Ile Pro Cys Arg Val Thr Asp Pro Gln Leu Val Val Thr Leu
```

```
                115                 120                 125
        His Glu Lys Lys Gly Asp Val Ala Leu Pro Val Pro Tyr Asp His Gln
        130                 135                 140

Arg Gly Phe Phe Gly Ile Phe Glu Asp Arg Ser Tyr Ile Cys Lys Thr
        145                 150                 155                 160

Thr Ile Gly Asp Arg Glu Val Asp Ser Asp Ala Tyr Tyr Val Tyr Arg
                        165                 170                 175

Leu Gln Val Ser Ser Ile Asn Val Ser Asn Ala Val Gln Thr Val
                        180                 185                 190

Val Arg Gln Gly Glu Asn Ile Thr Leu Met Cys Ile Val Ile Gly Asn
                195                 200                 205

Glu Val Val Asn Phe Glu Trp Thr Tyr Pro Arg Lys Glu Ser Gly Arg
        210                 215                 220

Leu Val Glu Pro Val Thr Asp Phe Leu Leu Asp Met Pro Tyr His Ile
        225                 230                 235                 240

Arg Ser Ile Leu His Ile Pro Ser Ala Glu Leu Glu Asp Ser Gly Thr
                        245                 250                 255

Tyr Thr Cys Asn Val Thr Glu Ser Val Asn Asp His Gln Asp Glu Lys
                        260                 265                 270

Ala Ile Asn Ile Thr Val Val Glu Ser Gly Tyr Val Arg Leu Leu Gly
                        275                 280                 285

Glu Val Gly Thr Leu Gln Phe Ala Glu Leu His Arg Ser Arg Thr Leu
        290                 295                 300

Gln Val Val Phe Glu Ala Tyr Pro Pro Pro Thr Val Leu Trp Phe Lys
        305                 310                 315                 320

Asp Asn Arg Thr Leu Gly Asp Ser Ser Ala Gly Glu Ile Ala Leu Ser
                        325                 330                 335

Thr Arg Asn Val Ser Glu Thr Arg Tyr Val Ser Glu Leu Thr Leu Val
                        340                 345                 350

Arg Val Lys Val Ala Glu Ala Gly His Tyr Thr Met Arg Ala Phe His
                        355                 360                 365

Glu Asp Ala Glu Val Gln Leu Ser Phe Gln Leu Gln Ile Asn Val Pro
        370                 375                 380

Val Arg Val Leu Glu Leu Ser Glu Ser His Pro Asp Ser Gly Glu Gln
        385                 390                 395                 400

Thr Val Arg Cys Arg Gly Arg Gly Met Pro Gln Pro Asn Ile Ile Trp
                        405                 410                 415

Ser Ala Cys Arg Asp Leu Lys Arg Cys Pro Arg Glu Leu Pro Pro Thr
                        420                 425                 430

Leu Leu Gly Asn Ser Ser Glu Glu Ser Gln Leu Glu Thr Asn Val
                        435                 440                 445

Thr Tyr Trp Glu Glu Glu Gln Glu Phe Glu Val Val Ser Thr Leu Arg
                450                 455                 460

Leu Gln His Val Asp Arg Pro Leu Ser Val Arg Cys Thr Leu Arg Asn
        465                 470                 475                 480

Ala Val Gly Gln Asp Thr Gln Glu Val Ile Val Val Pro His Ser Leu
                        485                 490                 495

Pro Phe Lys Asp Lys Thr His Thr Cys Pro Pro Cys Pro Ala Pro Glu
                        500                 505                 510

Leu Leu Gly Gly Pro Ser Val Phe Leu Phe Pro Pro Lys Pro Lys Asp
                        515                 520                 525

Thr Leu Met Ile Ser Arg Thr Pro Glu Val Thr Cys Val Val Val Asp
                        530                 535                 540
```

```
Val Ser His Glu Asp Pro Glu Val Lys Phe Asn Trp Tyr Val Asp Gly
545                 550                 555                 560

Val Glu Val His Asn Ala Lys Thr Lys Pro Arg Glu Glu Gln Tyr Asn
                565                 570                 575

Ser Thr Tyr Arg Val Val Ser Val Leu Thr Val Leu His Gln Asp Trp
            580                 585                 590

Leu Asn Gly Lys Glu Tyr Lys Cys Lys Val Ser Asn Lys Ala Leu Pro
        595                 600                 605

Ala Pro Ile Glu Lys Thr Ile Ser Lys Ala Lys Gly Gln Pro Arg Glu
610                 615                 620

Pro Gln Val Tyr Thr Leu Pro Pro Ser Arg Asp Glu Leu Thr Lys Asn
625                 630                 635                 640

Gln Val Ser Leu Thr Cys Leu Val Lys Gly Phe Tyr Pro Ser Asp Ile
                645                 650                 655

Ala Val Glu Trp Glu Ser Asn Gly Gln Pro Glu Asn Asn Tyr Lys Thr
            660                 665                 670

Thr Pro Pro Val Leu Asp Ser Asp Gly Ser Phe Phe Leu Tyr Ser Lys
        675                 680                 685

Leu Thr Val Asp Lys Ser Arg Trp Gln Gln Gly Asn Val Phe Ser Cys
690                 695                 700

Ser Val Met His Glu Ala Leu His Asn His Tyr Thr Gln Lys Ser Leu
705                 710                 715                 720

Ser Leu Ser Pro Gly Lys
            725

<210> SEQ ID NO 340
<211> LENGTH: 527
<212> TYPE: PRT
<213> ORGANISM: Artificial Sequence
<220> FEATURE:
<223> OTHER INFORMATION: Synthetic

<400> SEQUENCE: 340

Leu Val Ile Thr Pro Pro Gly Pro Glu Leu Ile Leu Asn Val Ser Ser
1               5                   10                  15

Thr Phe Val Leu Thr Cys Ser Gly Ser Ala Pro Val Val Trp Glu Arg
            20                  25                  30

Met Ser Gln Glu Leu Pro Gln Glu Met Ala Lys Ala Gln Asp Asn Thr
        35                  40                  45

Phe Ser Ser Val Leu Thr Leu Thr Asn Leu Thr Gly Leu Asp Thr Gly
    50                  55                  60

Glu Tyr Phe Cys Thr Tyr Asn Asp Ser Arg Gly Leu Glu Pro Asp Glu
65                  70                  75                  80

Arg Lys Arg Leu Tyr Ile Phe Val Pro Asp Pro Thr Val Gly Phe Leu
                85                  90                  95

Pro Asn Asp Ala Glu Glu Leu Phe Ile Phe Leu Thr Glu Ile Thr Glu
            100                 105                 110

Ile Thr Ile Pro Cys Arg Val Thr Asp Pro Gln Leu Val Val Thr Leu
        115                 120                 125

His Glu Lys Lys Gly Asp Ile Ala Leu Pro Val Pro Tyr Asp His Gln
    130                 135                 140

Arg Gly Phe Ser Gly Ile Phe Glu Asp Arg Ser Tyr Ile Cys Lys Thr
145                 150                 155                 160

Thr Ile Gly Asp Arg Glu Val Asp Ser Asp Ala Tyr Tyr Val Tyr Arg
                165                 170                 175
```

```
Leu Gln Val Ser Ser Ile Asn Val Ser Val Asn Ala Val Gln Thr Val
                180                 185                 190

Val Arg Gln Gly Glu Asn Ile Thr Leu Met Cys Ile Val Ile Gly Asn
            195                 200                 205

Glu Val Val Asn Phe Glu Trp Met Tyr Pro Arg Lys Glu Ser Gly Arg
    210                 215                 220

Leu Val Glu Pro Val Thr Asp Phe Leu Leu Asp Met Pro Tyr His Ile
225                 230                 235                 240

Arg Ser Ile Leu His Ile Pro Ser Ala Glu Leu Asp Ser Gly Thr
                245                 250                 255

Tyr Thr Cys Asn Val Thr Glu Ser Val Asn Asp His Gln Asp Glu Lys
            260                 265                 270

Ala Ile Asn Ile Thr Val Val Glu Ser Gly Tyr Val Arg Leu Leu Gly
            275                 280                 285

Glu Val Gly Ala Leu Gln Phe Ala Glu Leu His Arg Ser Arg Thr Leu
            290                 295                 300

Gln Val Val Phe Glu Ala Tyr Pro Pro Pro Thr Val Leu Trp Phe Lys
305                 310                 315                 320

Asp Asn Arg Thr Leu Gly Asp Ser Ser Ala Gly Glu Ile Ala Leu Ser
                325                 330                 335

Thr Arg Asn Val Ser Glu Thr Arg Tyr Val Ser Glu Leu Thr Leu Val
            340                 345                 350

Arg Val Lys Val Ala Glu Ala Gly His Tyr Thr Met Arg Ala Phe His
            355                 360                 365

Glu Asp Ala Glu Val Gln Leu Ser Phe Gln Leu Gln Ile Asn Val Pro
            370                 375                 380

Val Arg Val Leu Glu Leu Ser Glu Ser His Pro Asp Ser Gly Glu Gln
385                 390                 395                 400

Thr Val Arg Cys Arg Gly Arg Gly Met Pro Gln Pro Asn Ile Ile Trp
            405                 410                 415

Ser Ala Cys Arg Asp Leu Lys Arg Cys Pro Arg Glu Leu Pro Pro Met
            420                 425                 430

Leu Leu Gly Asn Ser Ser Glu Glu Glu Ser Gln Leu Glu Thr Asn Val
            435                 440                 445

Thr Tyr Trp Glu Glu Glu Gln Glu Phe Glu Val Val Ser Thr Leu Arg
450                 455                 460

Leu Gln His Val Asp Arg Pro Leu Ser Val Arg Cys Thr Leu Arg Asn
465                 470                 475                 480

Ala Val Gly Gln Asp Met Gln Glu Val Ile Val Val Pro His Ser Leu
            485                 490                 495

Pro Phe Lys Glu Gln Lys Leu Ile Ser Glu Glu Asp Leu Gly Gly Glu
            500                 505                 510

Gln Lys Leu Ile Ser Glu Glu Asp Leu His His His His His His
            515                 520                 525

<210> SEQ ID NO 341
<211> LENGTH: 1106
<212> TYPE: PRT
<213> ORGANISM: Homo sapiens

<400> SEQUENCE: 341

Met Arg Leu Pro Gly Ala Met Pro Ala Leu Ala Leu Lys Gly Glu Leu
1               5                   10                  15

Leu Leu Leu Ser Leu Leu Leu Leu Leu Glu Pro Gln Ile Ser Gln Gly
```

-continued

```
            20                  25                  30
Leu Val Val Thr Pro Gly Pro Glu Leu Val Leu Asn Val Ser Ser
            35                  40                  45
Thr Phe Val Leu Thr Cys Ser Gly Ser Ala Pro Val Val Trp Glu Arg
50                  55                  60
Met Ser Gln Glu Pro Pro Gln Glu Met Ala Lys Ala Gln Asp Gly Thr
65                  70                  75                  80
Phe Ser Ser Val Leu Thr Leu Thr Asn Leu Thr Gly Leu Asp Thr Gly
                    85                  90                  95
Glu Tyr Phe Cys Thr His Asn Asp Ser Arg Gly Leu Glu Thr Asp Glu
                100                 105                 110
Arg Lys Arg Leu Tyr Ile Phe Val Pro Asp Pro Thr Val Gly Phe Leu
            115                 120                 125
Pro Asn Asp Ala Glu Glu Leu Phe Ile Phe Leu Thr Glu Ile Thr Glu
        130                 135                 140
Ile Thr Ile Pro Cys Arg Val Thr Asp Pro Gln Leu Val Val Thr Leu
145                 150                 155                 160
His Glu Lys Lys Gly Asp Val Ala Leu Pro Val Pro Tyr Asp His Gln
                165                 170                 175
Arg Gly Phe Ser Gly Ile Phe Glu Asp Arg Ser Tyr Ile Cys Lys Thr
                180                 185                 190
Thr Ile Gly Asp Arg Glu Val Asp Ser Asp Ala Tyr Tyr Val Tyr Arg
            195                 200                 205
Leu Gln Val Ser Ser Ile Asn Val Ser Val Asn Ala Val Gln Thr Val
        210                 215                 220
Val Arg Gln Gly Glu Asn Ile Thr Leu Met Cys Ile Val Ile Gly Asn
225                 230                 235                 240
Glu Val Val Asn Phe Glu Trp Thr Tyr Pro Arg Lys Glu Ser Gly Arg
                245                 250                 255
Leu Val Glu Pro Val Thr Asp Phe Leu Leu Asp Met Pro Tyr His Ile
                260                 265                 270
Arg Ser Ile Leu His Ile Pro Ser Ala Glu Leu Glu Asp Ser Gly Thr
            275                 280                 285
Tyr Thr Cys Asn Val Thr Glu Ser Val Asn Asp His Gln Asp Glu Lys
        290                 295                 300
Ala Ile Asn Ile Thr Val Val Glu Ser Gly Tyr Val Arg Leu Leu Gly
305                 310                 315                 320
Glu Val Gly Thr Leu Gln Phe Ala Glu Leu His Arg Ser Arg Thr Leu
                325                 330                 335
Gln Val Val Phe Glu Ala Tyr Pro Pro Pro Thr Val Leu Trp Phe Lys
                340                 345                 350
Asp Asn Arg Thr Leu Gly Asp Ser Ser Ala Gly Glu Ile Ala Leu Ser
            355                 360                 365
Thr Arg Asn Val Ser Glu Thr Arg Tyr Val Ser Glu Leu Thr Leu Val
        370                 375                 380
Arg Val Lys Val Ala Glu Ala Gly His Tyr Thr Met Arg Ala Phe His
385                 390                 395                 400
Glu Asp Ala Glu Val Gln Leu Ser Phe Gln Leu Gln Ile Asn Val Pro
                405                 410                 415
Val Arg Val Leu Glu Leu Ser Glu Ser His Pro Asp Ser Gly Glu Gln
            420                 425                 430
Thr Val Arg Cys Arg Gly Arg Gly Met Pro Gln Pro Asn Ile Ile Trp
        435                 440                 445
```

```
Ser Ala Cys Arg Asp Leu Lys Arg Cys Pro Arg Glu Leu Pro Pro Thr
    450                 455                 460

Leu Leu Gly Asn Ser Ser Glu Glu Glu Ser Gln Leu Glu Thr Asn Val
465                 470                 475                 480

Thr Tyr Trp Glu Glu Glu Gln Glu Phe Glu Val Val Ser Thr Leu Arg
                485                 490                 495

Leu Gln His Val Asp Arg Pro Leu Ser Val Arg Cys Thr Leu Arg Asn
                500                 505                 510

Ala Val Gly Gln Asp Thr Gln Glu Val Ile Val Val Pro His Ser Leu
            515                 520                 525

Pro Phe Lys Val Val Val Ile Ser Ala Ile Leu Ala Leu Val Val Leu
    530                 535                 540

Thr Ile Ile Ser Leu Ile Ile Leu Ile Met Leu Trp Gln Lys Lys Pro
545                 550                 555                 560

Arg Tyr Glu Ile Arg Trp Lys Val Ile Glu Ser Val Ser Ser Asp Gly
                565                 570                 575

His Glu Tyr Ile Tyr Val Asp Pro Met Gln Leu Pro Tyr Asp Ser Thr
                580                 585                 590

Trp Glu Leu Pro Arg Asp Gln Leu Val Leu Gly Arg Thr Leu Gly Ser
            595                 600                 605

Gly Ala Phe Gly Gln Val Val Glu Ala Thr Ala His Gly Leu Ser His
            610                 615                 620

Ser Gln Ala Thr Met Lys Val Ala Val Lys Met Leu Lys Ser Thr Ala
625                 630                 635                 640

Arg Ser Ser Glu Lys Gln Ala Leu Met Ser Glu Leu Lys Ile Met Ser
                645                 650                 655

His Leu Gly Pro His Leu Asn Val Val Asn Leu Leu Gly Ala Cys Thr
            660                 665                 670

Lys Gly Gly Pro Ile Tyr Ile Ile Thr Glu Tyr Cys Arg Tyr Gly Asp
            675                 680                 685

Leu Val Asp Tyr Leu His Arg Asn Lys His Thr Phe Leu Gln His His
    690                 695                 700

Ser Asp Lys Arg Arg Pro Pro Ser Ala Glu Leu Tyr Ser Asn Ala Leu
705                 710                 715                 720

Pro Val Gly Leu Pro Leu Pro Ser His Val Ser Leu Thr Gly Glu Ser
                725                 730                 735

Asp Gly Gly Tyr Met Asp Met Ser Lys Asp Glu Ser Val Asp Tyr Val
                740                 745                 750

Pro Met Leu Asp Met Lys Gly Asp Val Lys Tyr Ala Asp Ile Glu Ser
            755                 760                 765

Ser Asn Tyr Met Ala Pro Tyr Asp Asn Tyr Val Pro Ser Ala Pro Glu
    770                 775                 780

Arg Thr Cys Arg Ala Thr Leu Ile Asn Glu Ser Pro Val Leu Ser Tyr
785                 790                 795                 800

Met Asp Leu Val Gly Phe Ser Tyr Gln Val Ala Asn Gly Met Glu Phe
                805                 810                 815

Leu Ala Ser Lys Asn Cys Val His Arg Asp Leu Ala Ala Arg Asn Val
            820                 825                 830

Leu Ile Cys Glu Gly Lys Leu Val Lys Ile Cys Asp Phe Gly Leu Ala
        835                 840                 845

Arg Asp Ile Met Arg Asp Ser Asn Tyr Ile Ser Lys Gly Ser Thr Phe
    850                 855                 860
```

Leu Pro Leu Lys Trp Met Ala Pro Glu Ser Ile Phe Asn Ser Leu Tyr
865                 870                 875                 880

Thr Thr Leu Ser Asp Val Trp Ser Phe Gly Ile Leu Leu Trp Glu Ile
                885                 890                 895

Phe Thr Leu Gly Gly Thr Pro Tyr Pro Glu Leu Pro Met Asn Glu Gln
                900                 905                 910

Phe Tyr Asn Ala Ile Lys Arg Gly Tyr Arg Met Ala Gln Pro Ala His
                915                 920                 925

Ala Ser Asp Glu Ile Tyr Glu Ile Met Gln Lys Cys Trp Glu Glu Lys
                930                 935                 940

Phe Glu Ile Arg Pro Pro Phe Ser Gln Leu Val Leu Leu Leu Glu Arg
945                 950                 955                 960

Leu Leu Gly Glu Gly Tyr Lys Lys Tyr Gln Gln Val Asp Glu Glu
                965                 970                 975

Phe Leu Arg Ser Asp His Pro Ala Ile Leu Arg Ser Gln Ala Arg Leu
                980                 985                 990

Pro Gly Phe His Gly Leu Arg Ser Pro Leu Asp Thr Ser Ser Val Leu
                995                 1000                1005

Tyr Thr Ala Val Gln Pro Asn Glu Gly Asp Asn Asp Tyr Ile Ile Pro
        1010                1015                1020

Leu Pro Asp Pro Lys Pro Glu Val Ala Asp Glu Gly Pro Leu Glu Gly
1025                1030                1035                1040

Ser Pro Ser Leu Ala Ser Ser Thr Leu Asn Glu Val Asn Thr Ser Ser
                1045                1050                1055

Thr Ile Ser Cys Asp Ser Pro Leu Glu Pro Gln Asp Glu Pro Glu Pro
                1060                1065                1070

Glu Pro Gln Leu Glu Leu Gln Val Glu Pro Glu Pro Glu Leu Glu Gln
        1075                1080                1085

Leu Pro Asp Ser Gly Cys Pro Ala Pro Arg Ala Glu Ala Glu Asp Ser
        1090                1095                1100

Phe Leu
1105

<210> SEQ ID NO 342
<211> LENGTH: 145
<212> TYPE: PRT
<213> ORGANISM: Artificial Sequence
<220> FEATURE:
<223> OTHER INFORMATION: hPDGFR-beta D1.mmH

<400> SEQUENCE: 342

Met His Arg Pro Arg Arg Gly Thr Arg Pro Pro Leu Ala Leu
 1               5                   10                  15

Leu Ala Leu Leu Leu Ala Ala Arg Gly Ala Asp Ala Leu Val Val
                20                  25                  30

Thr Pro Pro Gly Pro Glu Leu Val Leu Asn Val Ser Ser Thr Phe Val
                35                  40                  45

Leu Thr Cys Ser Gly Ser Ala Pro Val Val Trp Glu Arg Met Ser Gln
        50                  55                  60

Glu Pro Pro Gln Glu Met Ala Lys Ala Gln Asp Gly Thr Phe Ser Ser
65                  70                  75                  80

Val Leu Thr Leu Thr Asn Leu Thr Gly Leu Asp Thr Gly Glu Tyr Phe
                85                  90                  95

Cys Thr His Asn Asp Ser Arg Gly Leu Glu Thr Asp Glu Arg Lys Arg
                100                 105                 110

```
Leu Tyr Ile Phe Val Glu Gln Lys Leu Ile Ser Glu Glu Asp Leu Gly
            115                 120                 125

Gly Glu Gln Lys Leu Ile Ser Glu Glu Asp Leu His His His His
    130                 135                 140

His
145

<210> SEQ ID NO 343
<211> LENGTH: 227
<212> TYPE: PRT
<213> ORGANISM: Artificial Sequence
<220> FEATURE:
<223> OTHER INFORMATION: hPDGFR-beta D1-D2.mmH

<400> SEQUENCE: 343

Met His Arg Pro Arg Arg Gly Thr Arg Pro Pro Leu Ala Leu
 1               5                  10                  15

Leu Ala Ala Leu Leu Ala Ala Arg Gly Ala Asp Ala Leu Val Val
            20                  25                  30

Thr Pro Pro Gly Pro Glu Leu Val Leu Asn Val Ser Ser Thr Phe Val
        35                  40                  45

Leu Thr Cys Ser Gly Ser Ala Pro Val Val Trp Glu Arg Met Ser Gln
    50                  55                  60

Glu Pro Pro Gln Glu Met Ala Lys Ala Gln Asp Gly Thr Phe Ser Ser
65                  70                  75                  80

Val Leu Thr Leu Thr Asn Leu Thr Gly Leu Asp Thr Gly Glu Tyr Phe
                85                  90                  95

Cys Thr His Asn Asp Ser Arg Gly Leu Glu Thr Asp Glu Arg Lys Arg
            100                 105                 110

Leu Tyr Ile Phe Val Pro Asn Asp Ala Glu Glu Leu Phe Ile Phe Leu
        115                 120                 125

Thr Glu Ile Thr Glu Ile Thr Ile Pro Cys Arg Val Thr Asp Pro Gln
    130                 135                 140

Leu Val Val Thr Leu His Glu Lys Lys Gly Asp Val Ala Leu Pro Val
145                 150                 155                 160

Pro Tyr Asp His Gln Arg Gly Phe Phe Gly Ile Phe Glu Asp Arg Ser
                165                 170                 175

Tyr Ile Cys Lys Thr Thr Ile Gly Asp Arg Glu Val Asp Ser Asp Ala
            180                 185                 190

Tyr Tyr Val Tyr Arg Leu Gln Glu Gln Lys Leu Ile Ser Glu Glu Asp
        195                 200                 205

Leu Gly Gly Glu Gln Lys Leu Ile Ser Glu Glu Asp Leu His His His
    210                 215                 220

His His His
225

<210> SEQ ID NO 344
<211> LENGTH: 323
<212> TYPE: PRT
<213> ORGANISM: Artificial Sequence
<220> FEATURE:
<223> OTHER INFORMATION: hPDGFR-beta D1-D3.mmH

<400> SEQUENCE: 344

Met His Arg Pro Arg Arg Gly Thr Arg Pro Pro Leu Ala Leu
 1               5                  10                  15

Leu Ala Ala Leu Leu Ala Ala Arg Gly Ala Asp Ala Leu Val Val
            20                  25                  30
```

```
Thr Pro Pro Gly Pro Glu Leu Val Leu Asn Val Ser Ser Thr Phe Val
            35                  40                  45

Leu Thr Cys Ser Gly Ser Ala Pro Val Val Trp Glu Arg Met Ser Gln
 50                  55                  60

Glu Pro Pro Gln Glu Met Ala Lys Ala Gln Asp Gly Thr Phe Ser Ser
 65                  70                  75                  80

Val Leu Thr Leu Thr Asn Leu Thr Gly Leu Asp Thr Gly Glu Tyr Phe
                 85                  90                  95

Cys Thr His Asn Asp Ser Arg Gly Leu Glu Thr Asp Glu Arg Lys Arg
            100                 105                 110

Leu Tyr Ile Phe Val Pro Asn Asp Ala Glu Glu Leu Phe Ile Phe Leu
            115                 120                 125

Thr Glu Ile Thr Glu Ile Thr Ile Pro Cys Arg Val Thr Asp Pro Gln
            130                 135                 140

Leu Val Val Thr Leu His Glu Lys Lys Gly Asp Val Ala Leu Pro Val
145                 150                 155                 160

Pro Tyr Asp His Gln Arg Gly Phe Phe Gly Ile Phe Glu Asp Arg Ser
                165                 170                 175

Tyr Ile Cys Lys Thr Thr Ile Gly Asp Arg Glu Val Asp Ser Asp Ala
            180                 185                 190

Tyr Tyr Val Tyr Arg Leu Gln Ile Asn Val Ser Val Asn Ala Val Gln
            195                 200                 205

Thr Val Val Arg Gln Gly Glu Asn Ile Thr Leu Met Cys Ile Val Ile
            210                 215                 220

Gly Asn Glu Val Val Asn Phe Glu Trp Thr Tyr Pro Arg Lys Glu Ser
225                 230                 235                 240

Gly Arg Leu Val Glu Pro Val Thr Asp Phe Leu Leu Asp Met Pro Tyr
                245                 250                 255

His Ile Arg Ser Ile Leu His Ile Pro Ser Ala Glu Leu Glu Asp Ser
            260                 265                 270

Gly Thr Tyr Thr Cys Asn Val Thr Glu Ser Val Asn Asp His Gln Asp
            275                 280                 285

Glu Lys Ala Ile Asn Ile Thr Glu Gln Lys Leu Ile Ser Glu Glu Asp
            290                 295                 300

Leu Gly Gly Glu Gln Lys Leu Ile Ser Glu Glu Asp Leu His His His
305                 310                 315                 320

His His His
```

<210> SEQ ID NO 345
<211> LENGTH: 396
<212> TYPE: PRT
<213> ORGANISM: Artificial Sequence
<220> FEATURE:
<223> OTHER INFORMATION: hPDGFR-beta D1-D4.mmH

<400> SEQUENCE: 345

```
Met His Arg Pro Arg Arg Arg Gly Thr Arg Pro Pro Leu Ala Leu
  1               5                  10                  15

Leu Ala Ala Leu Leu Leu Ala Ala Arg Gly Ala Asp Ala Leu Val Val
                 20                  25                  30

Thr Pro Pro Gly Pro Glu Leu Val Leu Asn Val Ser Ser Thr Phe Val
            35                  40                  45

Leu Thr Cys Ser Gly Ser Ala Pro Val Val Trp Glu Arg Met Ser Gln
 50                  55                  60
```

-continued

```
Glu Pro Pro Gln Glu Met Ala Lys Ala Gln Asp Gly Thr Phe Ser Ser
 65                  70                  75                  80

Val Leu Thr Leu Thr Asn Leu Thr Gly Leu Asp Thr Gly Glu Tyr Phe
                 85                  90                  95

Cys Thr His Asn Asp Ser Arg Gly Leu Glu Thr Asp Glu Arg Lys Arg
            100                 105                 110

Leu Tyr Ile Phe Val Pro Asn Asp Ala Glu Glu Leu Phe Ile Phe Leu
            115                 120                 125

Thr Glu Ile Thr Glu Ile Thr Ile Pro Cys Arg Val Thr Asp Pro Gln
    130                 135                 140

Leu Val Val Thr Leu His Glu Lys Lys Gly Asp Val Ala Leu Pro Val
145                 150                 155                 160

Pro Tyr Asp His Gln Arg Gly Phe Phe Gly Ile Phe Glu Asp Arg Ser
                165                 170                 175

Tyr Ile Cys Lys Thr Thr Ile Gly Asp Arg Glu Val Asp Ser Asp Ala
            180                 185                 190

Tyr Tyr Val Tyr Arg Leu Gln Ile Asn Val Ser Val Asn Ala Val Gln
        195                 200                 205

Thr Val Val Arg Gln Gly Glu Asn Ile Thr Leu Met Cys Ile Val Ile
    210                 215                 220

Gly Asn Glu Val Val Asn Phe Glu Trp Thr Tyr Pro Arg Lys Glu Ser
225                 230                 235                 240

Gly Arg Leu Val Glu Pro Val Thr Asp Phe Leu Leu Asp Met Pro Tyr
                245                 250                 255

His Ile Arg Ser Ile Leu His Ile Pro Ser Ala Glu Leu Glu Asp Ser
            260                 265                 270

Gly Thr Tyr Thr Cys Asn Val Thr Glu Ser Val Asn Asp His Gln Asp
        275                 280                 285

Glu Lys Ala Ile Asn Ile Thr His Arg Ser Arg Thr Leu Gln Val Val
    290                 295                 300

Phe Glu Ala Tyr Pro Pro Pro Thr Val Leu Trp Phe Lys Asp Asn Arg
305                 310                 315                 320

Thr Leu Gly Asp Ser Ser Ala Gly Glu Ile Ala Leu Ser Thr Arg Asn
                325                 330                 335

Val Ser Glu Thr Arg Tyr Val Ser Glu Leu Thr Leu Val Arg Val Lys
            340                 345                 350

Val Ala Glu Ala Gly His Tyr Thr Met Arg Ala Phe His Glu Asp Ala
        355                 360                 365

Glu Gln Lys Leu Ile Ser Glu Glu Asp Leu Gly Gly Leu Gln Lys Leu
    370                 375                 380

Ile Ser Glu Glu Asp Leu His His His His His His
385                 390                 395
```